United States Patent
Willson et al.

(10) Patent No.: US 6,294,580 B1
(45) Date of Patent: *Sep. 25, 2001

(54) SUBSTITUTED 4-HYDROXY-PHENYLALCANOIC ACID DERIVATIVES WITH AGONIST ACTIVITY TO PPAR-GAMMA

(75) Inventors: Timothy Mark Willson, Durham; Robert Anthony Mook, Chapel Hill; Istvan Kaldor, Durham; Brad Richard Henke; David Norman Deaton, both of Cary; Jon Loren Collins, Durham; Jeffrey Edmond Cobb, Chapel Hill; Marcus Brackeen, Durham; Matthew Jude Sharp, Apex, all of NC (US); John Mark O'Callaghan, Kent (GB); Greg Alan Erickson; Grady Evan Boswell, both of Cary, NC (US)

(73) Assignee: Glaxo Wellcome Inc., Research Triangle Park, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 104 days.

(21) Appl. No.: 09/125,750
(22) PCT Filed: Feb. 26, 1997
(86) PCT No.: PCT/EP97/00916
 § 371 Date: Feb. 24, 1999
 § 102(e) Date: Feb. 24, 1999
(87) PCT Pub. No.: WO97/31907
 PCT Pub. Date: Sep. 4, 1997

(30) Foreign Application Priority Data

Feb. 28, 1996 (GB) .................................. 9604242

(51) Int. Cl.[7] ........................ A61K 31/19; A61K 31/135; C07C 221/00; C07D 333/32; C07D 211/72
(52) U.S. Cl. ........................ 514/570; 514/561; 514/649; 514/445; 514/351; 514/352; 514/375; 560/61; 562/471; 564/344; 549/65; 546/290; 546/312; 548/225; 548/230
(58) Field of Search ................. 560/61; 514/570, 514/561, 649, 445, 351, 352, 375; 562/471; 564/344; 549/65; 546/290, 312; 548/225, 230

(56) References Cited

U.S. PATENT DOCUMENTS

| | | |
|---|---|---|
| 4,340,605 | 7/1982 | Kawamatsu et al. . |
| 4,342,771 | 8/1982 | Schnur . |
| 4,367,234 | 1/1983 | Schnur . |
| 5,089,514 | 2/1992 | Hulin . |
| 5,220,023 | 6/1993 | Freyne et al. . |
| 5,232,945 | 8/1993 | Bernard . |
| 5,306,726 | 4/1994 | Hulin . |

FOREIGN PATENT DOCUMENTS

| | | |
|---|---|---|
| 08 325 564 A | 12/1996 | (JP) . |
| 08325264A | 12/1997 | (JP) . |
| 2017739 | 8/1994 | (RU) . |
| 1473300 | 2/1995 | (RU) . |
| 2124011 | 12/1998 | (RU) . |
| WO91/19702 A | 12/1991 | (WO) . |

(List continued on next page.)

OTHER PUBLICATIONS

"Chemical Abstracts", vol. 126, no. 9, 3 Mar. 1997, Columbus, Ohio, US; abstract no. 117964d. XP002032261.

*Primary Examiner*—Deborah C. Lambkin
(74) *Attorney, Agent, or Firm*—Robert H. Brink

(57) ABSTRACT

A compound having formula (I), wherein A is selected from the group consisting of: (i) phenyl, wherein said phenyl is optionally substituted by one or more halogen atoms, $C_{1-6}$alkyl, $C_{1-3}$alkoxy, $C_{1-3}$fluoroalkoxy, nitrile, or —$NR^7R^8$ where $R^7$ and $R^8$ are independently hydrogen or $C_{1-3}$alkyl; (ii) a 5- or 6-membered hetrocyclic group containing at least one heteroatom selected from oxygen, nitrogen and sulfur; and (iii) a fused bicyclic ring (a), wherein ring C represents a heterocyclic group as defined in point (ii) above, which bicyclic ring is attached to group B via a ring atom of ring C; B is selected from the group consisting of: (iv) $C_{1-6}$alkylene; (v) —$MC_{1-6}$alkylene or $C_{1-6}$alkyleneM$C_{1-6}$alkylene, wherein M is O, S, or —$NR^2$ wherein $R^2$ represents hydrogen or $C_{1-3}$alkyl; (vi) a 5- or 6-membered heterocyclic group containing at least one nitrogen heteroatom and optionally at least one further heteroatom selected from oxygen, nitrogen and sulfur and optionally substituted by $C_{1-3}$alkyl; and (vii) Het-$C_{1-6}$alkylene, wherein Het represents a heterocyclic group as defined in point (vi) above; Alk represents $C_{1-3}$alkylene; $R^1$ represents hydrogen or $C_{1-3}$alkyl; Z is selected from the group consisting of: (viii) —($C_{1-3}$alkylene) phenyl, which phenyl is optionally substituted by one or more halogen atoms; and (ix) —$NR^3R^4$, wherein $R^3$ represents hydrogen or $C_{1-3}$alkyl, and $R^4$ represents —Y—(C=O)—T—$R^5$, or —Y—(CH(OH))—T—$R^5$.

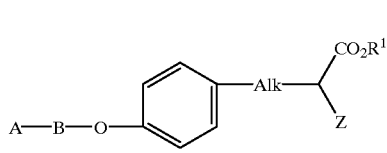

(I)

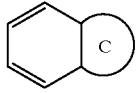

(a)

33 Claims, No Drawings

FOREIGN PATENT DOCUMENTS

| | | |
|---|---|---|
| WO93/21166 | 10/1993 | (WO) . |
| WO94/01420 | 1/1994 | (WO) . |
| WO94/13650 | 6/1994 | (WO) . |
| WO94/29285 A | 12/1994 | (WO) . |
| WO94/29302 | 12/1994 | (WO) . |
| WO95/03288 | 2/1995 | (WO) . |
| WO96/38415 A | 5/1996 | (WO) . |
| 98/00137 * | 1/1998 | (WO) . |

* cited by examiner

SUBSTITUTED 4-HYDROXY-PHENYLALCANOIC ACID DERIVATIVES WITH AGONIST ACTIVITY TO PPAR-GAMMA

This application is a 371 of PCT/EP97/00916 Feb. 26, 1997.

The present invention relates to certain novel compounds, to processes for their preparation, to pharmaceutical compositions containing them and to their use in medicine. More particularly, it relates to compounds which exhibit activation, including agonist activity, to peroxisome proliferator-activated receptor gamma (PPAR-gamma) thereby enabling them to modulate the blood glucose levels in mammals.

The treatment of Type II or Non-insulin Dependent Diabetes Mellitus (NIDDM) remains unsatisfactory despite the widespread use of insulin, sulfonylureas (e.g. chlorpropamide, tolbutamide, tolazamide), and biguanides (e.g, phenformin, metformin) as oral hypoglycaemic agents. Treatment of NIDDM usually begins with a combination of diet and exercise, with progression to oral hypoglycaemics (e.g. sulfonylureas) and in more severe cases, insulin. Unfortunately the available hypoglycaemics suffer from a wide range of undesirable toxic effects which limits their usefulness in treatment of NIDDM. There is thus a clear need for the development of novel hypoglycaemic agents which may be less toxic or which suceed where others are ineffective.

In the last decade a class of compounds known as thiazolidinediones (e.g. U.S. Pat. Nos. 5,089,514, 4,342,771, 4,367,234, 4,340,605, 5,306,726) have emerged as effective antidiabetic agents that enhance the insulin sensitivity of target tissues (skeletal muscle, liver, adipose) in animal models of NIDDM and also reduce lipid and insulin levels in these animal models. Recently, the thiazolidinedione troglitazone was shown to have these same beneficial effects in human patients suffering from impaired glucose tolerance, a metabolic condition that precedes the development of NIDDM, as in patients suffering from NIDDM (J. J. Nolan et. al., *N. Eng. J. Med.* 1188–1193, 331 (1994)). While the mechanism of action is unclear, thiazolidinediones do not cause increases in insulin secretion or in the number or affinity of insulin receptor binding sites, suggesting that thiazolidinediones amplify post-receptor events in the insulin signaling cascade (J. R. Colca and D. R. Morton, "Antihyperglycemic thiazolidinediones: ciglitazone and its analogs," in *New Antidiabetic Drugs*, C. J. Bailey and P. R. Flatt, eds., Smith-Gordon, New York, 255–261 (1990)).

Thiazolidinediones also induce the in vitro adipocyte differentiation of preadipocyte cell lines (A. Hiragun, et. al. *J. Cell. Physiol.* 124–130, 134 (1988); R. F. Kleitzen, et. al., *Mol. Pharmacol.* 393–398, 41 (1992)). Treatment of preadipocyte cell lines with the thiazolidinedione pioglitazone results in increased expression of the adipocyte-specific genes aP2 and adipsin as well as the glucose transporter proteins GLUT-1 and GLUT-4, which suggests that the hypoglycaemic effects of thiazolidinediones seen in vivo may be mediated through adipose tissue.

Recently, an orphan member of the steroid/thyroid/retinoid receptor superfamily of ligand-activated transcription factors termed Peroxisome Proliferator-Activated Receptor gamma (PPAR-gamma) has been discovered. PPAR-gamma is one of a subfamily of closely related PPARs encoded by independent genes (C. Dreyer, et. al., *Cell* 879–887, 68 (1992); A. Schmidt, et. al., *Mol. Endocrinol.* 1634–1641, 6, (1992); Y. Zhu, et. al., *J. Biol. Chem.* 26817–26820, 268 (1993); S. A. Kliewer et. al., *Proc. Nat. Acad. Sci. USA* 7355–7359, 91, (1994)). Three mammalian PPARs have been isolated and termed PPAR-alpha, PPAR-gamma, and NUC-1. These PPARs regulate expression of target genes by binding to DNA sequence elements, termed PPAR response elements (PPRE). To date, PPRE's have been identified in the enhancers of a number of genes encoding proteins that regulate lipid metabolism suggesting that PPARs play a pivotal role in the adipogenic signaling cascade and lipid homeostasis (H. Keller and W. Wahli, *Trends Endocrin. Met.* 291–296, 4 (1993)). It has now been reported that thiazolidinediones are potent and selective activators of PPAR-gamma and bind directly to the PPAR-gamma receptor (J. M. Lehmann et. al., *J. Biol. Chem.* 12953–12956, 270 (1995)), providing evidence that PPAR-gamma is a possible target for the therapeutic actions of the thiazolidinediones.

We have now discovered a novel group of compounds which bind to and activate the PPAR-gamma receptor. These compounds also show good blood-glucose lowering activity and are therefore of use in the treatment and/or prophylaxis of hyperglycaemia, dyslipidemia, and are of particular use in the treatment of Type II diabetes.

These compounds are also indicated to be of use for the treatment and/or prophylaxis of other diseases including Type I diabetes, hypertriglyceridemia, syndrome X, insulin resistance, heart failure, diabetic dyslipidemia, hyperlipidemia, hypercholesteremia, hypertension and cardiovascular disease, especially atherosclerosis. In addition, these compounds are indicated to be useful for the regulation of appetite and food intake in subjects suffering from disorders such as obesity, anorexia bulimia, and anorexia nervosa.

Accordingly, the present invention is directed to compounds having the formula (I):

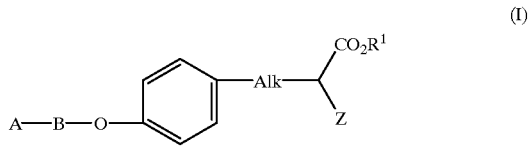

(I)

wherein
A is selected from the group consisting of:
(i) phenyl, wherein said phenyl is optionally substituted by one or more of the following groups; halogen atoms, $C_{1-6}$alkyl, $C_{1-3}$ alkoxy, $C_{1-3}$ fluoroalkoxy, nitrile, or —$NR^7R^8$ where $R^7$ and $R^8$ are independently hydrogen or $C_{1-3}$alkyl;
(ii) a 5- or 6-membered heterocyclic group containing at least one heteroatom selected from oxygen, nitrogen and sulfur; and
(iii) a fused bicyclic ring

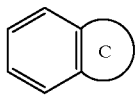

wherein ring C represents a heterocyclic group as defined in point (ii) above, which bicyclic ring is attached to group B via a ring atom of ring C;
B is selected from the group consisting of:
(iv) $C_{1-6}$ alkylene;
(v) —$MC_{1-6}$alkylene or $C_{1-6}$alkyleneM$C_{1-6}$alkylene, wherein M is O, S, or —$NR^2$ wherein $R^2$ represents hydrogen or $C_{1-3}$alkyl;

(vi) a 5- or 6-membered heterocyclic group containing at least one nitrogen heteroatom and optionally at least one further heteroatom selected from oxygen, nitrogen and sulfur and optionally substituted by $C_{1-3}$ alkyl; and (vii) Het-$C_{1-6}$alkylene, wherein Het represents a heterocyclic group as defined in point (vi) above;

Alk represents $C_{1-3}$alkylene;

$R^1$ represents hydrogen or $C_{1-3}$ alkyl;

Z is selected from the group consisting of:

(viii) —($C_{1-3}$alkylene) phenyl, which phenyl is optionally substituted by one or more halogen atoms; and (ix) —$NR^3R^4$, wherein $R^3$ represents hydrogen or $C_{1-3}$ alkyl, and $R^4$ represents —Y—(C=O)—T—$R^5$, or —Y—(CH(OH))—T—$R^5$, wherein:

(a) Y represents a bond, $C_{1-6}$ alkylene, $C_{2-6}$ alkenylene, $C_{4-6}$ cycloalkylene or cycloalkenylene, a heterocyclic group as defined in point (vi) above, or phenyl optionally substituted by one or more $C_{1-3}$ alkyl groups and/or one or more halogen atoms;

(b) T represents a bond, $C_{1-3}$ alkyleneoxy, —O— or —N($R^6$)—, wherein $R^6$ represents hydrogen or $C_{1-3}$ alkyl;

(c) $R^5$ represents $C_{1-6}$ alkyl, $C_{4-6}$ cycloalkyl or cycloalkenyl, phenyl (optionally substituted by one or more of the following groups; halogen atoms, $C_{1-3}$ alkyl, $C_{1-3}$ alkoxy groups, $C_{0-3}$alkyleneNR$^9$R$^{10}$ (where each $R^9$ and $R^{10}$ is independently hydrogen, $C_{1-3}$ alkyl, —SO$_2$C$_{1-3}$alkyl, or —CO$_2$C$_{1-3}$alkyl, —SO$_2$NHC$_{1-3}$alkyl), $C_{0-3}$ alkyleneCO$_2$H, $C_{0-3}$ alkyleneCO$_2$C$_{1-3}$alkyl, or —OCH$_2$C(O)NH$_2$), a 5- or 6-membered heterocyclic group as defined in point (ii) above, a bicylic fused ring

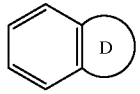

wherein ring D represents a 5- or 6-membered heterocyclic group containing at least one heteroatom selected from oxygen, nitrogen and sulfur and optionally substituted by (=O), which bicyclic ring is attached to T via a ring atom of ring D: or —$C_{1-6}$alkyleneMR$^{11}$ M is O, S, or —NR$^{12}$ wherein $R^{12}$ and $R^{11}$ are independently hydrogen or $C_{1-3}$ alkyl, or a tautomeric form thereof, and/or a pharmaceutically acceptable salt or solvate thereof.

Those skilled in the art will recognize that stereocenters exist in compounds of Formula (I). Accordingly, the present invention includes all possible stereoisomers and geometric isomers of Formula (I) and includes not only racemic compounds but also the optically active isomers as well. When a compound of Formula (I) is desired as a single enantiomer, it may be obtained either by resolution of the final product or by stereospecific synthesis from either isomerically pure starting material or any convenient intermediate. Resolution of the final product, an intermediate or a starting material may be effected by any suitable method known in the art. See, for example, *Stereochemistry of Carbon Compounds* by E. L. Eliel (Mcgraw Hill, 1962) and *Tables of Resolving Agents* by S. H. Wilen. Additionally, in situations where tautomers of the compounds of Formula (I) are possible, the present invention is intended to include all tautomeric forms of the compounds.

It will also be appreciated by those skilled in the art that the compounds of the present invention may also be utilized in the form of a pharmaceutically acceptable salt or solvate thereof. The physiologically acceptable salts of the compounds of Formula (I) include conventional salts formed from pharmaceutically acceptable inorganic or organic acids or bases as well as quaternary ammonium acid addition salts. More specific examples of suitable acid salts include hydrochloric, hydrobromic, sulfuric, phosphoric, nitric, perchloric, fumaric, acetic, propionic, succinic, glycolic, formic, lactic, maleic, tartaric, citric, pamoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, stearic, tannic and the like. Other acids such as oxalic, while not in themselves pharmaceutically acceptable, may be useful in the preparation of salts useful as intermediates in obtaining the compounds of the invention and their pharmaceutically acceptable salts. More specific examples of suitable basic salts include sodium, lithium, potassium, magnesium, aluminium, calcium, zinc, $N,N^1$-dibenzylethylenediamine, chloroprocaine, choline, diethanolamine, ethylenediamine, N-methylglucamine and procaine salts. References hereinafter to a compound according to the invention include both compounds of Formula (I) and their pharmaceutically acceptable salts and solvates.

The terms $C_{1-3}$alkyl or alkylene and $C_{1-6}$alkyl or alkylene as used herein respectively contain 1 to 3 or 1 to 6 carbon atoms and appropriately include straight chained and branched alkyl or alkylene groups, typically methyl, methylene, ethyl and ethylene groups, and straight chained and branched propyl, propylene, butyl and butylene groups. The term $C_{2-6}$alkenyl or alkenylene as used herein contains 2 to 6 carbon atoms and appropriately includes straight chained and branched alkenyl and alkenylene groups, in particular propenylene or the like.

The term $C_{1-3}$ alkyleneoxy as used herein denotes —O—$C_{1-3}$ alkylene-, wherein $C_{1-3}$ alkylene is substantially as defined above, e.g. —O—CH$_2$— etc.

The terms $C_{4-6}$ cycloalkyl, $C_{4-6}$ cycloalkylene, $C_{4-6}$ cycloalkenyl and $C_{4-6}$ cycloalkenylene include cyclic groups containing 4 to 6 carbon atoms, such as cyclopentane, cyclopentylene, cyclohexane, cyclohexylene, cyclohexene and cyclohexenylene.

The term halogen as used herein includes fluorine, chlorine, bromine and iodine.

The term 5- or 6-membered heterocyclic group as used herein includes 5- or 6-membered unsubstituted heterocycloalkyl groups and substituted or unsubstituted heteroaryl groups, e.g. substituted or unsubstituted imidazolidinyl, piperidyl, piperazinyl pyrrolidinyl, morpholinyl, pyridyl, pyridazinyl, pyrimidinyl, pyrazinyl, pyrrolyl, pyrazolyl, imidazolyl, pyranyl, furyl, thienyl, oxazolyl, isoxazolyl, oxadiazolyl, thiazolyl, thiadiazolyl, triazolyl or tetrazolyl.

By substituted heterocyclic group is meant a 5 or 6 membered heteroaryl group substituted by one or more of the following; halogen atoms, $C_{1-3}$ alkyl, $C_{1-3}$ alkoxy groups, $C_{0-3}$ alkylene N $R^9R^{10}$ (where each $R^9$ and $R^{10}$ is idependently hydrogen, $C_{1-3}$ alkyl, —SO$_2$C$_{1-3}$ alkyl or CO$_2$C$_{1-3}$ alkyl, —SO$_2$NHC$_{1-3}$ alkyl), $C_{0-3}$ alkylene CO$_2$H, $C_{0-3}$ alkylene CO$_2$C$_{1-3}$ alkyl, —OCH$_2$C(O)NH$_2$, —C$_{1-3}$ fluoroalkyl, —CN or SC$_{1-6}$ alkyl.

In formula (I) above, in the case where Y represents a bond, the nitrogen atom of —NR$^3$R$^4$ is directly linked to —(C=O) or (CH(OH)) of R$^4$, ie. Z represents —N(R$^3$)—(C=O) —T—R$^5$ or —N(R$^3$)(CH(OH))—T—R$^5$. Similarly, in the case where T represents a bond, —(C=O) or (CH (OH)) of $R^4$ is directly linked to $R^5$, ie. Z represents —N($R^3$)—Y—(C=O)—$R^5$ or —N($R^3$)—Y—(CH(OH))—$R^5$. It may be the case that both Y and T represent a bond, whereby Z represents —N($R^3$)—(C=O)—$R^5$ or —N($R^3$)—(CH(OH))—$R^5$.

Aptly A represents any of phenyl, heteroaryl (e.g. pyridyl) or

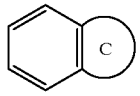

wherein fused ring C represents a 5-membered heteroaryl group containing at least one nitrogen heteroatom and optionally a further heteroatom selected from nitrogen and oxygen (e.g. oxazolyl, imidazolyl). Particularly A represents any of phenyl, pyridyl, piperazinyl, or benzoxazolyl, any of which can optionally be substituted by one or more $C_{1-3}$ alkyl, especially phenyl, piperazinyl, or pyridyl.

B suitably represents any of $C_{1-3}$alkylene (e.g. methylene), —N(CH$_3$)$C_{1-3}$alkylene (e.g. —N(CH$_3$)(CH$_2$)$_2$—) or Het-$C_{1-6}$ alkylene, wherein Het represents a 5-membered heterocyclic group containing at least one nitrogen heteroatom and optionally at least one further heteroatom selected from oxygen and sulfur (e.g. pyrrolidinyl, oxazolyl and thiazolyl) and aptly substituted by $C_{1-3}$alkyl. Particularly B represents —N(CH$_3$)(CH$_2$)$_2$, oxazolyl —$C_{1-6}$ alkylene, which oxazolyl is optionally substituted by $C_{1-3}$ alkyl, or thiazolyl which is optionally substituted by $C_{1-3}$ alkyl.

Appropriately Alk represents methylene.

Appropriately $R^1$ represents hydrogen, methyl or ethyl, especially hydrogen.

Suitably Z may represent —($C_{1-3}$alkylene) phenyl substituted by one or more halogen atoms, such as optionally substituted benzyl. Preferably Z represents —NR$^3$R$^4$ substantially as hereinbefore described. Generally $R^3$ represents hydrogen. As hereinbefore described, $R^4$ represents —Y—(C=O)—T—$R^5$, or —Y—(CH(OH))—T—$R^5$ especially —Y(C=O)—T—$R^5$, and particular groupings represented by $R^4$ include:

Y represents phenyl (optionally substituted by one or more halogen atoms, or one or more $C_{1-3}$alkyl e.g. methyl groups), T represents a bond or an oxygen atom, and $R^5$ represents $C_{1-3}$ alkyl or phenyl (optionally substituted by one or more halogen atoms or one or more $C_{1-3}$ alkyl groups);

Y represents a heterocyclic group substantially as hereinbefore described (e.g. thienyl), T represents a bond and $R^5$ represents phenyl (optionally substituted by one or more halogen atoms or one or more $C_{1-3}$ alkyl groups);

Y represents $C_{2-6}$alkenylene- (e.g. propenylene), T represents a bond and $R^5$ represents phenyl (optionally substituted by one or more halogen atoms);

Y represents $C_{4-6}$cycloalkenylene- (e.g. cyclohexenylene), T represents a bond and $R^5$ represents phenyl;

Y represents phenyl, T represents a bond and $R^5$ represents a heterocyclic group substantially as hereinbefore described (e.g. piperidyl);

Y represents a bond, T represents a bond and $R^5$ represents a bicyclic ring

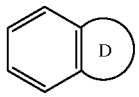

substantially as hereinbefore described (e.g. D represents a 6-membered heterocyclic ring, in particular pyranyl substituted by (C=O));

Y represents phenyl, T represents a bond and $R^5$ represents $C_{4-6}$cycloalkyl (e.g. cyclohexyl);

Y represents phenyl, T represents $C_{1-3}$ alkyleneoxy (e.g. —O—CH$_2$—) or N($R^6$)— (e.g. —NH—) and $R^5$ represents phenyl.

Preferably when Z represents NR$^3$R$^4$ $R^3$ represents H and $R^4$ represents Y—(C=O)—T—$R^5$ the said NH and said (C=O) are positioned ortho to each other on Y (which is phenyl), T is a bond or —O—, $R^5$ is $C_{1-6}$ alkyl, or phenyl (optionally substituted by one or more: halogen atoms, $C_{1-3}$ alkyl, $C_{1-3}$ alkoxy groups, $C_{0-3}$alkyleneNR$^9$R$^{10}$ where each $R^9$ and $R^{10}$ is independently hydrogen, $C_{1-3}$ alkyl, —SO$_2$C$_{1-3}$alkyl, or —CO$_2$C$_{1-3}$alkyl, —SO$_2$NHC$_{1-3}$alkyl, $C_{0-3}$ alkyleneCO$_2$H, $C_{0-3}$ alkyleneCO$_2$C$_{1-3}$alkyl, or —OCH$_2$C(O)NH$_2$).

Particularly suitably Y represents phenyl, T represents a bond or —O— and $R^5$ represents $C_{1-3}$ alkyl or phenyl e.g. $R^4$ represents

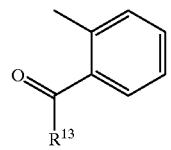

wherein $R^{13}$ represents phenyl or OCH$_3$.

An appropriate subgroup of compounds according to the present invention can be represented by formula (Ia)

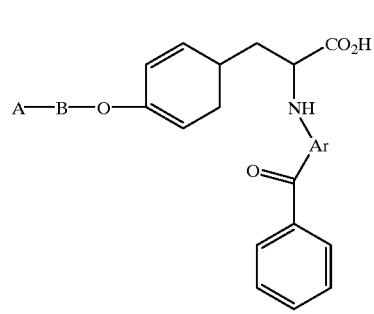

(Ia)

wherein A and B are substantially as hereinbefore described, and Ar represents phenyl or a 5- or 6-membered heteroaryl group containing at least one heteroatom selected from oxygen, nitrogen and sulfur; and salts and solvates thereof.

Suitably in formula (Ia), A is selected from phenyl, pyridyl and benzoxazoyl. In particular, A in Formula (Ia) represents phenyl or pyridyl. Furthermore, B in Formula (Ia) is suitably selected from —NR$^2$C$_{1-6}$alkylene substantially as hereinbefore described and Het-C$_{1-6}$alkylene optionally substituted by C$_{1-3}$alkyl substantially as hereinbefore described. In particular, B in Formula (Ia) represents —N(CH$_3$)(CH$_2$)$_2$— or oxazolyl-C$_{1-6}$alkylene, which oxazolyl is optionally substituted by C$_{1-3}$alkyl, e.g. methyl.

A particular subgroup of the compounds of formula 1 are compounds of formula (I):
wherein;
A is selected from the group consisting of:
(i) phenyl optionally substituted by one or more halogen atoms;
(ii) a 5- or 6-membered heterocyclic group containing at least one heteroatom selected from oxygen, nitrogen and sulfur; and
(iii) a fused bicyclic ring

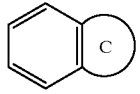

wherein ring C represents a heterocyclic group as defined in point (ii) above, which bicyclic ring is attached to group B via a ring atom of ring C;
B is selected from the group consisting of:
(iv) $C_{1-6}$ alkylene;
(v) —$NR_{1-6}$alkylene, wherein $R^2$ represents hydrogen or $C_{1-3}$ alkyl;
(vi) a 5- or 6-membered heterocyclic group containing at least one nitrogen heteroatom and optionally at least one further heteroatom selected from oxygen, nitrogen and sulfur and optionally substituted by $C_{1-3}$ alkyl; and
(vii) Het-$C_{1-6}$alkylene, wherein Het represents a heterocyclic group as defined in point (vi) above;
Alk represents $C_{1-3}$alkylene;
$R^1$ represents hydrogen or $C_{1-3}$ alkyl;
Z is selected from the group consisting of:
(viii) —($C_{1-3}$alkylene) phenyl, which phenyl is optionally substituted by one or more halogen atoms; and
(ix) —$NR^3R^4$, wherein $R^3$ represents hydrogen or $C_{1-3}$ alkyl, and $R^4$ represents —Y—(C=O)—T—$R^5$, or —Y—(CH(OH))—T—$R^5$, wherein:
(a) Y represents a bond, $C_{1-6}$ alkylene, $C_{2-6}$ alkenylene, $C_{4-6}$ cycloalkylene or cycloalkenylene, a heterocyclic group as defined in point (vi) above, or phenyl optionally substituted by one or more $C_{1-3}$ alkyl groups and/or one or more halogen atoms;
(b) T represents a bond, $C_{1-3}$ alkyleneoxy, —O— or —N($R^6$)—, wherein $R^6$ represents hydrogen or $C_{1-3}$ alkyl;
(c) $R^5$ represents $C_{1-6}$ alkyl, $C_{4-6}$ cycloalkyl or cycloalkenyl, phenyl optionally substituted by one or more halogen atoms or one or more $C_{1-3}$ alkyl groups, a 5- or 6-membered heterocyclic group as defined in point (ii) above, or a bicylic fused ring

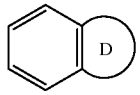

wherein ring D represents a 5- or 6-membered heterocyclic group containing at least one heteroatom selected from oxygen, nitrogen and sulfur and optionally substituted by (=O), which bicyclic ring is attached to T via a ring atom of ring D;
or a tautomeric form thereof, and/or a pharmaceutically acceptable salt or solvate thereof.

Particular compounds according to the present invention include:

3-(4-Benzyloxy-phenyl)-2(S)-(1-methyl-3-oxo-3-phenyl-propenylamino)-propionic acid dicyclohexylamine salt 3-(4-Benzyloxy-phenyl)-2(S)-(1-methyl-3-oxo-3-phenyl-propenylamino)-propionic acid methyl ester 2(S)-(2-Benzoyl-cyclohex-1-enylamino)-3-(4-benzyloxy-phenyl)-propionic acid dicyclohexylamine salt 2-(2-benzoylphenylamino)-3-(4-benzyloxyphenyl) propanoic acid 3-(4-Benzyloxy-phenyl)-2-(2-benzyloxy-phenytamino)-propionic acid methyl ester 3-(4-Benzyloxy-phenyl)-2-(phenylcarbamoyl-phenylamino)-propionic acid methyl ester 3-(4-Benzyloxy-phenyl)-2-[2-(piperidine-1-carbonyl)-phenylamino]-propionic acid methyl ester 2-(3-Benzoyl-thiophen-2-yl-amino)-3-(4-benzyloxy-phenyl)-propionic acid 2-(2-Benzoyl-thiophen-3-yl-amino)-3-(4-benzyloxy-phenyl)-propionic acid 3-(4-Benzyloxy-phenyl)-2(S)-[(4-oxo4H-chromene-3-carbonyl)-amino]-propionic acid methyl ester.

2-(2-Benzoyl-phenylamino)-3-{4-[2-(methyl-pyridin-2-yl-amino)-ethoxy]-phenyl}-propionic acid 2(S)-(2-benzoyl-phenylamino)-3-{4-[2-(methyl-pyridin-2-yl-amino)-ethoxy]-phenyl}-propionic acid 2-(2-Benzoyl-phenylamino)-3-{4-[2-(methyl-pyridin-2-yl-amino)-ethoxy]-phenyl}-propionic acid ethyl ester 2-(1-Methyl-3-oxo-3-phenyl-propenylamino)-3-{4-[2-(methyl-pyridin-2-yl-amino)-ethoxy]-phenyl}-propionic acid dicyclohexylamine salt 3-{4-[2-(benzoxazol-2-yl-methyl-amino)-ethoxy]-phenyl}-2-(2-benzoyl-phenylamino)-propionic acid 3-{4-[2-(benzoxazol-2-yl-methyl-amino)-ethoxy]-phenyl}-2-(2-benzoyl-phenylamino)-propionic acid 3-{4-[2-(Benzoxazol-2yl-methyl-amino)-ethoxy]-phenyl}-2(S)-(1-methyl-3-oxo-3-phenyl-propenylamino)-propionic acid dicyclohexylamine salt 3-{4-[2-(Benzoxazol-2-yl-methyl-amino)-ethoxy]-phenyl}-2(S)-[3-(3-iodo-phenyl)-1-methyl-3-oxo-propenylamino]-propionic acid dicyclohexylamine salt 3-{4-[2-(benzoxazol-2-yl-methyl-amino)-ethoxy]-phenyl}-2-(2-benzoyl-4-methyl-phenylamino)-propionic acid 3-{4-[2-(benzoxazol-2-yl-methyl-amino)-ethoxy]-phenyl}-2-(2-benzoyl4-chloro-phenylamino)-propionic acid 3-[4-(1-Benzoxazol-2-yl-pyrrolidin-3-yloxy)-phenyl]-2-(2-benzoyl-phenylamino)-propionic acid 3-[4-(1-benzoxazol-2-yl)-pyrrolidin-2R-yl-methoxy)-phenyl]-2-(2-benzoyl-phenylamino)-propionic acid 3-[4-(1-benzoxazol-2-yl)-pyrrolidin-2S-yl-methoxy)-phenyl]-2-(2-benzoyl-phenylamino)-propionic acid 3-{4-[2-(Benzoxazol-2-yl-methyl-amino)-ethoxy]-phenyl}-2-(2-cyclohexanecarbonyl-phenylamino)-propionic acid 3-{4-[2-Benzoxazol-2-yl-methyl-amino)-ethoxy]-phenyl}-2-(2-benzoyl-thiophen-3-ylamino)-propionic acid.

3-{4-[2-(Benzoxazol-2-yl-methyl-amino)-ethoxy]-phenyl}-2-benzyl-prop ionic acid trifluoroacetate.

3-{4-[2-(Benzoxazol-2-yl-methyl-amino)-ethoxy]-phenyl}-2-(2-bromo-benzyl)-propionic acid trifluoroacetate.

3-{4-[2-(Benzoxazol-2-yl-methyl-amino)-ethoxy]-phenyl}-2(S)-[(4-oxo4H-chromene-3-carbonyl)-amino]-propionic acid.

2(S)-(2-Benzoyl-phenylamino)-3-{4-[2-(5-methyl-2-phenyl-oxazol-4-yl)-ethoxy]-phenyl}-propionic acid 2(2-Benzoyl-phenylamino)-3-{4-[2-(4-chlorophenyl)-thiazol-4ylmethoxy]-phenyl}-piropionic acid 3-[4-(2-Benzoimidazol-1-yl-ethoxy)-phenyl]-2-(2-benzoyl-phenylamino)-propionic acid 2(S)-(2-benzoyl-phenylamino)-3-{4-[2-(5-methyl-2-(4-methoxy)-phenyl-2-oxazol-4-yl)-ethoxy]-phenyl}-propionic acid 2(S)-(2-benzoyl-phenylamino)-3-{4-[2-(5-methyl-2-(4-fluoro)-phenyl-oxazol-4-yl)-ethoxy]-phenyl}-propionic acid 2(S)-(2-benzoyl-phenylamino)-3-{4-[2-(5-methyl-2-(5-methyl-thien-2-yl)-oxazol-4-yl)-ethoxy]-phenyl}-propionic acid 2(S)-(2-benzoyl-phenylamino)-3-{4-[2-(5-methyl-1-phenyl-1H-pyrazol-3-yl)-ethoxy]-phenyl}-propionic acid 2(S)-(2-benzoyl-phenylamino)-3-{4-[2-(5-methyl-2-piperidin-1-yl-oxazol-4-yl)-ethoxy]-phenyl}-propionic acid 2(S)-(2-benzoyl-phenylamino)-3-{4-[2-(5-methyl-2-morpholin4-yl-thiazol-4-yl)-ethoxy]-phenyl}-propionic acid 2(S)-(2-benzoyl-phenylamino)-3-{4-[2-(5-methyl-2-(4-pyridyl)-thiazol-4-yl)-ethoxy]-phenyl}-propionic acid 2(S)-(2-benzoyl-phenylamino)-3-{4-[2-(2-dimethylamino-5-methyl-thiazol-4-yl)-ethoxy]-phenyl}-propionic acid 2(S)-(2-benzoyl-phenylamino)-3-{4-[2-(5-methyl-2-(5-methyl-isoxazol-3-yl)-thiazol-4-yl)-ethoxy]-phenyl}-propionic acid 2(S)-(2-benzoyl-phenylamino)-3-(4-{2-[5-methyl-2-(4-methyl[1,2,3]thiadiazol-5-yl)-thiazol-4-yl]-ethoxy}-phenyl)-propionic acid 2(S)-(2-benzoyl-phenylamino)-3-(4-{2-[5-methyl-2-(4-methyl-piperazin-1-yl)-thiazol-4-yl]-ethoxy}-phenyl)-propionic acid 2(S)-(2-benzoy-phenylamino)-3-(4-{2-[2-(3-dimethylamino-propylamino)-5-methyl-thiazol-4-yl]-ethoxy}-phenyl)-propionic acid 2(S)-(2-benzoyl-phenylamino)-3-(4-{2-[2-(2-methoxy-ethylamino)-5-methyl-thiazol-4-yl]-ethoxy}-phenyl)-propionic acid 2-(1-Carboxy-2-{4-[2-(5-methyl-2-phenyl-thiazol-4-yl)-ethoxy]-phenyl}-ethylamino)-benzoic acid methyl ester 2-(1-Carboxy-2-{4-[2-(4-clhorophenylsulfanyl)-ethoxy]-phenyl}-ethylamino)-benzoic acid methyl ester 2-{1-Carboxy-2-[4-(1-phenyl-pyrrolidin-2-ylmethoxy)-phenyl]-ethylamino} benzoic acid methyl ester 3-{4-[2-(Benzoxazol-2-yl-methyl-amino)-ethoxy]-phenyl}-2-(2-cyclopentanecarbonyl-phenylamino)-propionic acid 3-{4-[2-(Benzoxazol-2-yl-methyl-amino)-ethoxy]-phenyl}-2-(2-cycloheptanecarbonyl-phenylamino)-propionic acid 3-{4-[2-(Benzoxazol-2-yl-methyl-amino)-ethoxy]-phenyl}-2-(2-cyclohexanecarbonyl-5-fluoro-phenylamino)-propionic acid 3-{4-[2-(Benzoxazol-2-yl-methyl-amino)-ethoxy]-phenyl}-2-(4-cyclohexanecarbonyl-2-methyl-2H-pyrazol-3-ylamino)-propionic acid 3-{4-[2-(Benzoxazol-2-yl-methyl-amino)-ethoxy]-phenyl}-2-(3-benzoyl-thiophene-2-ylamino)-propionic acid 2-(2-Cyclohexanecarbonyl-phenylamino)-3-{4-[2-(5-methyl-2-phenyl-oxazol-4-yl)-ethoxy]-phenyl}-propionic acid 2-(2-Cyclohexanecarbonyl-phenylamino)-3-{4-[2-(5-methyl-2-phenyl-oxazol-4-yl)-ethoxy]-phenyl}-propionic acid 3-[4-(1-Benzoxazol-2-yl-pyrrolidin-3-yloxy)-phenyl]-2-(2-benzoyl-phenylamino)-propionic acid 3-{4-[2-(5-Methyl-2-phenyl-oxazol-4-yl)-ethoxy]-phenyl}-2(S)-[2-(pyridine-4-carbonyl)-phenylamino]-propionic acid 3-{4-[2-(5-methyl-2-phenyl-oxazol-4-yl)-ethoxy]-phenyl}-2(S)-[2-(pyridineN-oxide-4-carbonyl)-phenylamino]-propionic acid 3-{4-[2-(5-Methyl-2-phenyl-oxazol-4-yl)-ethoxy]-phenyl}-2(S)-[2-(pyridine-3-carbonyl)-phenylamino]-propionic acid 3-{4-[2-(5-methyl-2-phenyl-oxazol-4-yl)-ethoxy]-phenyl}-2(S)-[2-(pyridine-N-oxide-3-carbonyl)-phenylamino]-propionic acid 2S-(2-benzoyl-phenylamino)-3-{4-[2-(5-methyl-3-phenyl-pyrazol-1-yl)-ethoxy]-phenyl}-propionic acid 2S-(2-benzoyl-phenylamino)-3-[4-(1-pyridin-2-yl-pyrrolidin-2S-yl-methoxy)-phenyl]-propionic acid 2S-(2-benzoyl-phenylamino)-3-{4-[2-(1-methyl-4-phenyl-1H-imidazol-2-yl)-ethoxy]-phenyl}-propionic acid 2S-(2-benzoyl-phenylamino)-3-{4-[2-(3-furan-2-yl-5-methyl-pyrazol-1-yl)-ethoxy]-phenyl}-propionic acid 2S-(2-benzoyl-phenylamino)-3-{4-[2-(5-methyl-3-phenyl-[1,2,4]triazol-1-yl)-ethoxy]-phenyl}-propionic acid 2S-(2-benzoyl-phenylamino)-3-{4-[2-(3-methoxymethyl-5-methyl-2-phenyl-3H-imidazol-4-yl)-ethoxy]-phenyl}-propionic acid 2S-(2-benzoyl-phenylamino)-3-{4-[2-(5-methyl-2-phenyl-3H-imidazol-4-yl)-ethoxy]-phenyl}propionic acid hydrochloride salt 2S-(2-benzoyl-phenylamino)-3-{4-[2-(5-methyl-2-phenyl-thiazol-4-yl)-ethoxy]-phenyl}-propionic acid 2(S)-(2 -benzoyl-phenylamino)-3-{4-[2-(5-methyl-2-(3-methyl-thien-2-yl)-oxazol-4-yl-ethoxy]-phenyl}-propionic acid 2(S)-(2-{4-[2-(5-nitro-2-pyridyloxy)-ethoxy]-phenyl}-1-methoxycarbonyl-ethylamino)-benzoic acid 2(S)-(2-{4-[2-(5-chloro-2-pyridylsulfanyl)-ethoxy]-phenyl}-1-methoxycarbonyl-ethylamino)-benzoic acid 2(S)-(2-{4-[2-(N-ethyl-2-methyl-toluidino)-ethoxy]-phenyl}-1-methoxycarbonyl-ethylamino)-benzoic acid 3-[4-(3-Benzoxazol-2-yl-thiazolidin4(R)-ylmethoxy)-phenyl]-2(S)-(2-benzoyl-phenylamino)-propionic acid 3-{4-[2-(benzoxazol-2-yl-methyl-amino)-ethoxy]-phenyl}-2-[2-(4-trifluoromethyl-benzoyl)-phenylamino-propionic acid 3-{4-[2-(benzoxazol-2-yl-methyl-amino)-ethoxy]-phenyl}-2-[2-(2-thiophenecarbonyl)-phenylamino-propionic acid 3-{4-[2-(benzoxazol-2-yl-methyl-amino)-ethoxy]-phenyl}-2-[2-(3-thiophenecarbonyl)-phenylamino-propionic acid 3-{4-[2-(benzoxazol-2-yl-methyl-amino)-ethoxy]-phenyl}-2-[2-(3-trifluoromethylbenzoyl)-phenylamino-propionic acid 3-{4-[2-(benzoxazol-2-yl-methyl-amino)-ethoxy]-phenyl}-2-[2-(2-trifluoromethyl-benzoyl)-phenylamino-propionic acid 3-{4-[2-(benzoxazol-2-yl-methyl-amino)-ethoxy]-phenyl}-2-[2-(3-methoxy-benzoyl)-phenylamino-propionic acid 3-{4-[2-(benzoxazol-2-yl-methyl-amino)-ethoxy]-phenyl}-2-[2-(2-methoxy-benzoyl)-phenylamino-propionic acid 3-{4-[2-(benzoxazol-2-yl-methyl-amino)-ethoxy]-phenyl}-2-[2-(3-methyl-benzoyl)-phenylamino-propionic acid 2-[2-(4-dimethylaminomethyl-benzoyl)-phenylamino]-3-{4-[2-(5-methyl-2-phenyl-oxazol-4-yl)-ethoxy]-phenyl}-propionic acid hydrochloride 2-[2-(4-aminomethyl-benzoyl)-phenylamino]-3-{4-[2-(5-methyl-2-phenyl-oxazol-4-yl)-ethoxy]-phenyl}-propionic acid hydrochloride 3-{4-[2-(benzoxazol-2-yl-methyl-amino)-ethoxy]-phenyl}-2-[2-(2,6-dimethylbenzoyl)-phenylamino-propionic acid 3-(2-{1-carboxy-2-[4-(2-{5-methyl-2-phenyl-oxazol-4-yl}-ethoxy)-phenyl]-ethylamino}-benzoyl benzoic acid 2-[2-(3-hydroxymethyl-benzoyl)-phenylamino]-3-{4-[2-(5-methyl-2-phenyl-oxazol-4-yl)-ethoxy]-phenyl}-propionic acid 2-[2-(3-aminomethyl-benzoyl)-phenylamino]-3-{4-[2-(5-methyl-2-phenyl-oxazol-4-yl)-ethoxy]-phenyl}-propionic acid hydrochloride 2-[2-(3-dimethylaminomethyl-benzoyl)-phenylamino]-3-{4-[2-(5-methyl-2-phenyl-oxazol-4-yl)-ethoxy]-phenyl}-propionic acid hydrochloride 2(S)-(1-carboxy-2-{4-{2-(5-methyl-2-phenyl-oxazol-4-yl)-ethoxy]-phenyl}-ethylamino)-benzoic acid methyl ester 2(S)-(1-carboxy-2-{4-{2-(5-methyl-2-phenyl-oxazol-4-yl)-ethoxy]-phenyl}-ethylamino)-benzoic acid 2-aminoethyl amide hydrochloride 2(S)-(1-carboxy-2-{4-{2-(5-methyl-2-phenyl-oxazol-4-yl)-ethoxy]-phenyl}-ethylamino)-benzoic acid 3-aminopropyl amide hydrochloride 2-(1-carboxy-2-{4-{2-(5-methyl-2-phenyl-oxazol-4-yl)-ethoxy]-phenyl}-ethylamino)-benzoic acid methyl amide 3-{4-[2-(benzoxazol-2-yl-methyl-amino)-ethoxy]-phenyl}-2-[2-(3-hydroxy-benzoyl)-phenylamino]-propionic acid 3-{4-[2-(5-methyl-2-phenyl-oxazol-4-yl)-ethoxy]-phenyl}-2-[2-(4-propylsulfamoyl-benzoyl)-phenylamino]-propionic acid 2-[2-(3-amino-benzoyl)-phenylamino]-3-{4-[2-(5-methyl-2-phenyl-oxazol-4-yl)-ethoxy]-phenyl}-propionic acid 2-[2-(3-methanesulfonylamino-benzoyl)-phenylamino]-3-{4-[2-(5-methyl-2-phenyl-oxazol-4-yl)-ethoxy]-phenyl}-propionic acid 2-[2-(3-methoxycarbonylamino-benzoyl)-phenylamino]-3-{4-[2-(5-methyl-2-phenyl-oxazol-4-yl)-ethoxy]-phenyl}-propionic acid 2-[2-(3-hydroxy-benzoyl)-phenylamino]-3-{4-[2-(5-methyl-2-phenyl-oxazol-4-yl)-ethoxy]-phenyl}-propionic acid 2-[2-(3-Carbanoylmethoxy-benzoyl)-phenylamino]-3-{4-[2-(5-methyl-2-phenyl-oxazol-4-yl)-ethoxy]-phenyl}-propionic acid 2(S)-(2-benzoyl-phenylamino)-3-{4-[2-(5-methyl-2-pyridin-4-yl-oxazol-4-yl)-ethoxy]-phenyl}-propionic acid 2(S)-(2-benzoyl-phenylamino)-3-(4-{2-[5-methyl-2-(4-methyl-piperazin-1-yl)-thiazol-4-yl]-ethoxy}-phenyl)-propionic acid hydrochloride 2(S)-(2-benzoyl-phenylamino)-3-(4-{2-[5-methyl-2-(4-tert-butoxycarbonyl-piperazin-1-yl)-thiazol-4-yl]-ethoxy}-phenyl)-propionic acid 2(S)-(2-benzoyl-phenylamino)-3-{4-[2-(5-methyl-2-piperazin-1-yl-thiazol-4-yl)-ethoxy]-phenyl}-propionic acid (S)-(2-benzoyl-phenylamnino)-3-(4-{2-[5-methyl-2-(4-methylsulfonyl-piperazin-1-yl)-thiazol-4-yl]-ethoxy}-phenyl)-propionic acid 2(S)-(1-carboxy-2-{4-[2-(4-dimethylamino-phenyl)-ethoxy]-phenyl}-ethylamino)-benzoic acid methyl ester 2(S)-[1-methoxycarbonyl-2-(4-{2-[5-methyl-2-(4-methyl-piperazin-1-yl)-thiazol-4-yl]-ethoxy}-phenyl)-ethylamino]-benzoic acid 2(S)-(1-carboxy-2-{4-[2-(4-chloro-phenyl)-ethoxy]-phenyl}-ethylamino)-benzoic acid mnethyl ester 2(S)-(1-carboxy-2-{4-[2-(4-trifluoromethoxy-phenyl)-ethoxy]-phenyl}-ethylamino)-benzoic acid methyl ester 3-{4-[2-(Benzoxazol-2-yl-methylamino)-ethoxy]-phenyl}-3-(4-benzoyl-thienylamino)-propionic acid 3-{4-[2-(Benzoxazol-2-yl-methylamino)-ethoxy]-phenyl}-2-(2-(4-biphenylcarbonyl)-phenylamino)-propionic acid.

3-{4-[2-(Benzoxazol-2-yl-methylamino)-ethoxy]-phenyl}-2-(2-(4-methoxy-benzoyl)-phenylamino)-propionic acid 3-{4-[2-(Benzoxazol-2-yl-methylamino)-ethoxy]-phenyl}-2-(2-(4-methyl-benzoyl)-phenylamino)-propionic acid 3-{4-[2-(Benzoxazol-2-yl-methylamino)-ethoxy]-phenyl}-2-(2-(2-methyl-benzoyl)-phenylamino)-propionic acid 2-(2-Benzoyl-phenylamino)-3-{4-[2-(4-chloro-phenyl)-ethoxy]-phenyl}-propionic acid 2-(2-Benzoyl-phenylamino)-3-{4-[2-(4-methyl-thiazol-5-yl)-ethoxy]-phenyl}-propionic acid 2-(2-Benzoy-phenylamino)-3-{4-2[-(4-chloro-phenylsulfanyl)ethoxy]- phenyl}-propionic acid 2-(2-Benzoyl-phenylamino)-3-[4-(4-isopropyl-benzyloxy)-phenyl]-propionic acid 2-(2-Benzoyl-phenylamino)-3-[4-(4-chloro-benzyloxy)-phenyl]-propionic acid 2-(2-Benzoyl-phenylamino)-3-{4-[3-(4-methoxy-phenyl}-propoxyl-phenyl}-propionic acid 2-(2-Benzoyl-phenylamino)-3-{4-[2-(4-dimethylamino-phenyl)-ethoxy]-phenyl}-propionic acid 2-(2-Benzoyl-phenylamino)-3-{4-[2-(4-bromo-phenoxy)-ethoxy]-phenyl}-propionic acid 2-(2-Benzoyl-phenylamino)-3-{4-[2-(5-nitro-pyridin-2-yloxy)-ethoxy]-phenyl}-propionic acid 2-(2-Benzoyl-phenylamino)-3-(-4-{2-[3-(6-methyl-pyridin-2-yl)-propoxy]-ethoxyl}-phenyl)-propionic acid 2-(2-Benzoyl-phenylamino)-3-[4-(2-pyridin-3-yl-ethoxy)-phenyl]-propionic acid 2-(2-Benzoy-phenylamino)-3-{4-[2-(3-methyl-6-oxo-6H-pyridazin-1-yl)-ethoxy]-phenyl}-propionic acid 2-(2-Benzoyl-phenylamino)-3-{4-[2-(4-trifluoromethoxy-phenyl)-ethoxy]-phenyl}-propionic acid 2-(2-Benzoyl-phenylamino)-3-{4-[2-(3-cyano-phenoxy)-ethoxy]-phenyl}-propionic acid 2-(2-Benzoyl-phenylamino)-3-{4-[2-(6-methoxy-pyridin-2-ylsulfanyl)-ethoxy]-phenyl}-propionic acid 2-(2-Benzoyl-phenylamino)-3-{4-[1-(4-nitrophenyl)-pyrrolidin-2-ylmethoxy]-phenyl}-propionic acid A particular subgroup by compounds according to the present invention include:

2(S)-(1-carboxy-2-{4-{2-(5-methyl-2-phenyo-oxazol-4-yl)-ethoxy]-phenyl}-ethylamino)-benzoic acid methyl ester 3-{4-[2-(benzoxazol-2-yl-methyl-amino)-ethoxy]-phenyl}-2(S)-(2-benzoyl-phenylamino)-propionic acid;

3-{4-[2-(Benzoxazol-2-yl-methyl-amino)-ethoxy]-phenyl}-2-(2-cyclohexanecarbonyl-phenylamino)-propionic acid;

3-{4-[2-Benzoxazol-2-yl-methyl-amino)-ethoxy]-phenyl}-2-(2-benzoyl-thiophen-3-ylamino)-propionic acid.

2(S)-[1-methoxycarbonyl-2-(4-{2-[5-methyl-2-(4-methyl-piperazin-1-yl)-thiazol-4-yl]-ethoxy}-phenyl)-ethylamino]-benzoic acid 2(S)-(2-benzoyl-phenylamino)-3-{4-[2-(methyl-pyridin-2-yl-amino)-ethoxy]-phenyl}-propionic acid;

2(S)-(2-Benzoyl-phenylamino)-3-{4-[2-(5-methyl-2-phenyl-oxazol-4-yl)-ethoxy]-phenyl}-propionic acid;

and pharmaceutically acceptable salts and solvates thereof.

The invention further provides a compound of Formula (I), or (Ia), or a pharmaceutically acceptable salt or solvate thereof, for use in therapy, and in particular, in human medicine.

According to another aspect, the present invention provides the use of a compound of Formula (I), or (Ia), or a pharmaceutically acceptable salt or solvate thereof for the manufacture of a medicament for the treatment of conditions where modification of the effects of PPAR-gamma is of therapeutic benefit.

According to a further aspect of the present invention, there is provided herein a method for the treatment of a mammal, including man, in particular in the treatment conditions where modification of the effects of PPAR-gamma is of therapeutic benefit, the method comprising administering to the patient a therapeutically effective amount of a compound of Formula (I), or (Ia), or a pharmaceutically acceptable salt or solvate thereof.

It will be appreciated by those skilled in the art that reference herein to treatment extends to prophylaxis as well as the treatment of established diseases or symptoms. Moreover, it will be appreciated that the amount of a compound of the invention required for use in treatment will vary with the nature of the condition being treated and the age and the condition of the patient and will be ultimately at the discretion of the attendant physician or veterinarian. In general, however, doses employed for adult human treatment will typically be in the range of 0.02–5000 mg per day, e.g., 1–1500 mg per day. The desired dose may conveniently be presented in a single dose or as divided doses administered at appropriate intervals, for example as two, three, four or more sub-doses per day.

While it is possible that compounds of the present invention may be therapeutically administered as the raw chemical, it is preferable to present the active ingredient as a pharmaceutical formulation. Accordingly, the present invention further provides for a pharmaceutical formulation comprising a compound of Formula (I), or (Ia), or a pharmaceutically acceptable salt or solvate thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof. There is further provided by the present invention a process of preparing a pharmaceutical formulation comprising a compound of formula (I), or (Ia), which process comprises admixing a compound of formula (I), or (Ia), or a pharmaceutically acceptable salt thereof, with one or more pharmaceutically acceptable carriers therefor, and optionally other therapeutic and/or prophylactic ingredients.

Formulations of the present invention include those especially formulated for oral, buccal, parenteral, transdermal, inhalation, intranasal, transmucosal, implant, or rectal administration, however, oral administration is preferred. For buccal administration, the formulation may take the form of tablets or lozenges formulated in conventional manner. Tablets and capsules for oral administration may contain conventional excipients such as binding agents, (for example, syrup, acacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium iauryl sulfate. The tablets may be coated according to methods well-known in the art.

Alternatively, the compounds of the present invention may be incorporated into oral liquid preparations such as aqueous or oily suspensions, solutions, emulsions, syrups or elixirs, for example. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid. Such preparations may also be formulated as suppositories, e.g., containing conventional suppository bases such as cocoa butter or other glycerides.

Additionally, formulations of the present invention may be formulated for parenteral administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile, pyrogen-free water) before use.

The formulations according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (as an emulsion in an acceptable oil, for example), ion exchange resins or as sparingly soluble derivatives as a sparingly soluble salt, for example.

The formulations according to the invention may contain between 0.1–99% of the active ingredient, conveniently from 30–95% for tablets and capsules and 3–50% for liquid preparations.

There is further provided by the present invention processes for the preparation of compounds of formula (I). Unless otherwise indicated, A, B, Alk, $R^1$ and Z (and the further substituents represented thereby) are substantially as hereinbefore described.

According to a general process (A), a compound of formula (I) may be prepared from a compound of formula (II)

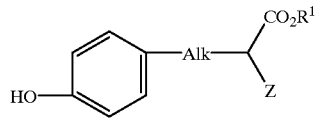

(II)

either directly, or indirectly, via a single or multistep reaction by reacting with a compound of formula A—B—X wherein X is a leaving group or a hydroxyl group, and B represents a group comprising $C_{1-6}$ alkylene, B being such that X is bonded directly to a $C_{1-6}$ alkylene.

Suitable reaction conditions are described below and in the accompanying Examples. See also, for example, Chung et al., Selective Functionalization of (S)-Tyrosine, Tetrahedton, 49(26), pp. 5767–5776, (1993), Solar et al., Selective O-Alkylation of Tyrosine, Journal of Organic Chemistry, 31, pp 1996–1997 (1966), O. Mitsunobu, Synthesis, p 1 (1981), and D. L. Hughes, Org. React. Vol. 42, p 335 (1992).

For example, A is preferably phenyl, pyridyl, benzoxazolyl or piperazinyl, any of which may optionally be substituted by one or more $C_{1-3}$alkyl groups. More preferably, A represents phenyl, pyridyl, benzoxazolyl (piperazinyl).

B is preferably Het-$C_{1-6}$ alkylene as descibed hereinbefore and Z is preferably —NH—Y—(C=O)—T—$R^5$ wherein Y is phenyl, optionally substituted by one or more $C_{1-3}$alkyl groups and/or one or more halogen atoms; T is a bond or —O— and $R^5$ represents $C_{1-6}$alkyl or phenyl (optionally substituted by one or more halogen atoms, $C_{1-3}$ alkyl, $C_{1-3}$ alkoxy groups, $C_{0-3}$alkyleneNR$^9$R$^{10}$ where each $R^9$ and $R^{10}$ is independently hydrogen, $C_{1-3}$ alkyl, —SO$_2$C$_{1-3}$alkyl, SO$_2$NHC$_{1-3}$alkyl, $C_{0-3}$ alkyleneCO$_2$H, CO—$_3$, $C_{0-3}$alkyleneCO$_2$C$_{1-3}$alkyl, or —OCH$_2$C(O)NH$_2$).

More preferably X represents a halide group or an alkyl- or arylsulfonoxyl group and $R^1$ represents hydrogen. Even more preferably, the compounds of formulae ABX and formula (II) are:

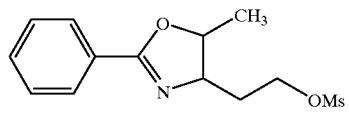

and

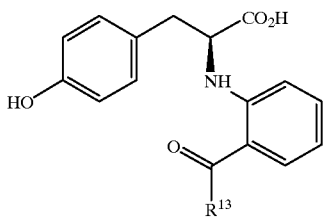

wherein OMs is a mesylate leaving group and $R^{13}$ represents a phenyl or OCH$_3$ group.

In compounds of formula (II) wherein $R^1$ represents a $C_{1-3}$alkyl group, preferably methyl, and X a hydroxyl group the reaction between ABX and the compound of formula (II) comprises a Mitsunobu reaction followed by hydrolysis of the alkyl ester group to the corresponding acid without isolating the ester. Preferably the Mitsunobu reaction mixture comprises toluene.

More preferably the compounds of formulae ABX and (II) are

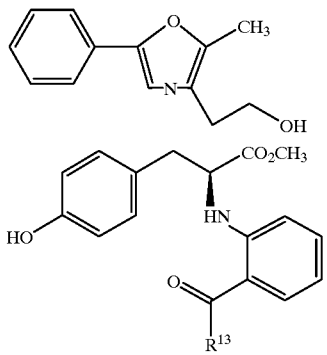

wherein $R^{13}$ is a phenyl or OCH$_3$ group.

When Z represents the following compound:

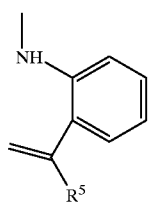

then the compound of formula (II) is prepared by first preparing a compound of formula (II) wherein Z is

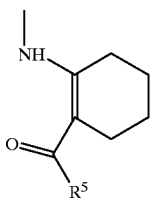

followed by a dehydrogenation with a dehydrogenation catalyst in the presence of a hydrogen acceptor. Preferably this hydrogen acceptor is an aromatic nitro compound.

A compound of formula (I) may be prepared by reaction with A—B—X, B being such that X is bonded directly to a $C_{1-6}$alkylene as described above and wherein X is a hydroxyl group or a suitable leaving group such as a halogen or an alkyl- or arylsulfonyloxy group (e.g. mesylate).

Alternatively, in the case wherein B represents —$NR^2C_{1-6}$alkylene, a compound of formula (I) may be prepared from a compound of formula (II) via a protected intermediate which can appropriately be represented by formula (III)

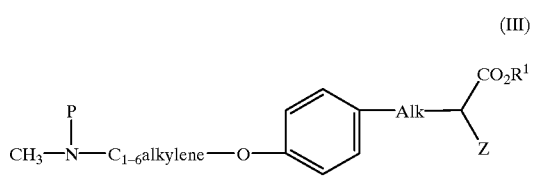

(III)

wherein P represents a protecting group, such as an alkoxycarbonyl e.g. t-butoxycarbonyl or the like, using techniques as hereinafter described in the accompanying Examples and representing protection and deprotection reactions known in the art e.g. as described in T. W. Green & P. G. M. Wuts (1991), Protecting Groups in Organic Chemistry, John Wiley & Sons.

A compound of formula (II) can, for example, be prepared from a compound of formula (IV)

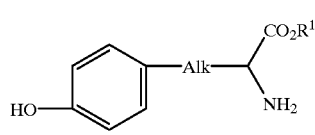

(IV)

suitably by reaction with a diketone e.g. 2-benzoyl-cyclohexanone, appropriately in the presence of a metal catalyst e.g. palladium. Preferably, $R^1$ is alkyl, and the diketone is first reacted with the amine followed by dehydrogenation in the presence of a metal catalyst and a hydrogen acceptor. Preferable hydrogen acceptors are aromatic nitro compounds that are easily reduced, e.g., p-nitrotoluene. If it is desired for $R^1$ to be hydrogen, the compound where $R^1$ is alkyl can be hydrolyzed, for example, in base in a solvent mixture of water and a polar-aprotic solvent. A compound of formula (IV) is commercially available or may be prepared as described in J. Med. Chem 1978, 21(5), 430–7.

According to a further general process (B), a compound of formula (I) may be prepared from a compound of formula (V)

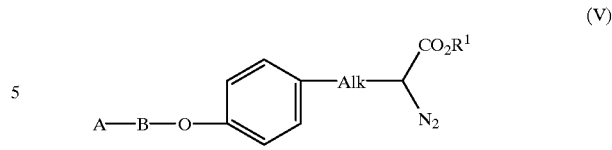

(V)

suitably by reaction with $NR^3R^4H$. For example, the reaction may be carried out suitably by reflux in the presence of a metal catalyst e.g. a rhodium catalyst (rhodium acetate dimer), and appropriately a hydrocarbon solvent e.g. toluene or the like. It will be appreciated that process (B) yields compounds of formula (I) wherein Z represents —$NR^3R^4$.

A compound of formula (V) may be prepared by diazotization of a compound of formula (VI)

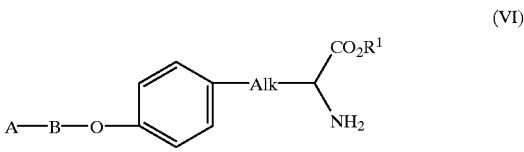

(VI)

Appropriately the diazotization reaction is carried out by reflux in the presence of a nitrite e.g. isoamyl nitrite.

Compounds of formula (VI) may be commercially available e.g. O-benzyl-tyrosine methyl ester. Alternatively compounds of formula (VI) may be prepared from known starting materials e.g. a benzoxazole halide and an aminoalcohol as hereinafter described in the accompanying examples.

A compound of formula (I) may however be prepared directly from a compound of formula (VI) via a general process (C). For example, a compound of formula (VI) may be reacted with a diketone of general formula $CH_3$—$(CH_2)_n$—(C=O)—$CH_2$—(C=O)—T—$R^5$, where n is an integer selected from 0 to 3, so as to yield a compound of formula (I) wherein Z represents —NH—$C_{2-6}$alkenylene-(C=O)—T—$R^5$. In a further embodiment, a compound of formula (VI) may be acylated by reaction with $R^5$—(C=O)—X, where X is a suitable leaving group substantially as hereinbefore described, suitably in the presence of a base e.g. a tertiary amine, such as triethylamine or the like.

According to a further process (D), a compound of formula (I) may be prepared from a compound of formula (VII)

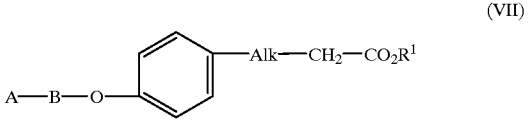

(VII)

by reaction with a strong base, suitably an alkali metal amide, followed by reaction with a compound of formula Z-X, where X is a suitable leaving group as hereinbefore described. In particular, process (D) is employed in the preparation of compounds of formula (I) wherein Z represents-($C_{1-3}$ alkylene)phenyl substantially as hereinbefore described. Suitably, the reaction is carried out in the presence of an ether solvent, e.g. tetrahydrofuran with stirring for several hours.

Appropriately, a compound of formula (VII) may be prepared from compounds of formulae (VIII) and (IX);

A—B—P (VIII)

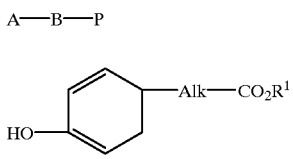
(IX)

wherein P may be a suitable protecting group substantially as hereinbefore described. Compounds of formula (IX) are commercially available. Compounds of formula (VIII) may be prepared from known starting materials, using techniques, for example, as referred to above starting from a benzoxazole halide and an aminoalcohol.

According to a further general process (E), a compound of formula (I) may be prepared by cyclisation of a compound of formula (X)

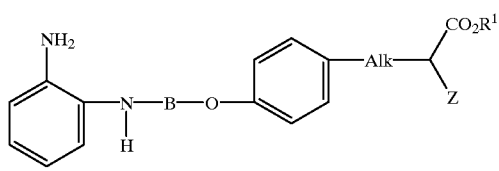
(X)

to yield a compound of formula (I) wherein A represents a bicyclic ring

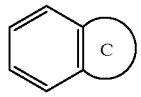

C being a 5- or 6-membered heterocyclic ring containing two nitrogen heteroatoms, the cyclisation conveniently being carried out in an acidic environment.

Suitably a compound of formula (X) may be prepared from a compound of formula (XI)

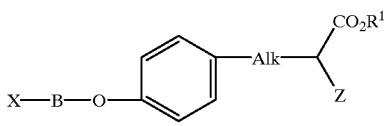
(XI)

by reaction with 1,2-phenylene diamine, suitably in the presence of an alkali metal carbonate e.g. potassium carbonate or the like. X is a leaving group substantially as hereinbefore described, in particular a mesylate group.

A compound of formula (XI) can be prepared from a compound of formula (XII)

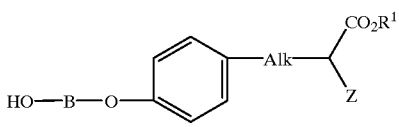
(XII)

suitably by reaction with, for example, an alkyl or aryl sulfonyl halide, e.g. methanesulfonylchloride, appropriately in the presence of an ether solvent e.g. tetrahydrofuran, and a tertiary amine e.g. triethylamine.

A compound of formula (XII) may appropriately be prepared from a compound of formula (II) substantially as hereinbefore described, e.g. by reaction with an alkylene carbonate in the presence of an alkali metal carbonate e.g. potassium carbonate.

According to a further aspect of the present invention a compound of formula (I) can be converted to another compound of formula (I). A particular interconversion reaction involves conversion of a compound of formula (I) wherein $R^1$ represents $C_{1-3}$alkyl, to a compound of formula (I) wherein $R^1$ represents hydrogen, suitably employing hydrolytic techniques e.g. an alkali metal hydroxide, in the presence of an ether solvent e.g. tetrahydrofuran and an alcoholic solvent e.g. methanol or the like.

It will therefore be appreciated by persons skilled in the art that compounds which fall within general formula (I), may in some instances, be hereinafter described in the intermediate section, as they are useful for the preparation of other compounds of formula (I).

For any of the general processes and schemes described above, it may be necessary and/or desirable to protect sensitive or reactive groups. Protecting groups are employed according to standard methods of organic synthesis (T. W. Green and P. G. M. Wuts (1991) *Protecting Groups in Organic Synthesis*, John Wiley & Sons). These groups are removed at a convenient stage of synthesis using methods known from the art. Thus, for example, amino groups may be protected by a group selected from aralkyl (e.g. benzyl), acyl, or sulfonyl, e.g. allylsulfonyl, tert-butoxycarbonyl, phthalimide, or tosyl; subsequent removal of the protecting group being effected when desired by hydrolysis or hydrogenolysis as appropriate using standard conditions. Thus, for example, tert-butoxycarbonyl groups may be removed by hydrolysis under acidic conditions. Hydroxyl and carboxyl groups may be protected using any conventional hydroxyl or carboxyl protecting group. Examples of suitable hydroxyl and carboxyl protecting groups include groups selected from alkyl, e.g. methyl, tert-butyl, or methoxymethyl, aralkyl, e.g. benzyl, diphenylmethyl, or triphenylmethyl, heterocyclic groups such as tetrahydropyranyl, acyl. e.g. acetyl or benzoyl, and silyl groups such as trialkylsilyl, e.g. tert-butyldimethylsilyl. The hydroxyl protecting groups may be removed by conventional techniques. Thus, for example, alkyl, silyl, acyl, and heterocyclic groups may be removed by hydrolysis under acidic or basic conditions. Aralkyl groups such as triphenylmethyl may similiarly be removed by hydrolysis under acidic conditions. Aralkyl groups such as benzyl may be cleaved by hydrogenolysis in the presence of a Noble metal catalyst such as palladium-on-charcoal. Silyl groups may also conveniently be removed using a source of fluoride ions such as tetra-n-butylammonium fluoride.

Many of the above reactions and synthetic routes can be done on solid support. For example, $R^1$ in Formula (II) can represent a suitable solid phase support, for example, $R^1$ can be a 2-chlorotritylchloride polystyrene resin. After performing the appropriate reactions, the desired compound of Formula (I) can be isolated by cleavage from the soid phase support.

The following examples are set forth to illustrate the synthesis of some particular compounds of the present invention and to further exemplify particular applications of general processes described above. Accordingly, the following Example section is in no way intended to limit the scope of the invention contemplated herein.

As used herein the symbols and conventions used in these processes, schemes and examples are consistent with those used in the contemporary scientific literature, for example, the Journal of the American Chemical Society. Unless otherwise noted, all starting materials were obtained from commercial suppliers and used without further purification. Specifically, the following abbreviations may be used in the examples and throughout the specification: g (grams); mg (milligrams); L (liters); mL (milliliters); $\mu$L (microliters); psi (pounds per square inch); M (molar); mM (millimolar); i. v. (intravenous); Hz (Hertz); MHz (megahertz); mol (moles); RT or rt (room temperature); min (minutes); h (hours); mp. (melting point); TLC (thin layer chromatography); HPLC (high pressure liquid chromatography); $t_r$ (retention time); RP (reverse phase); MeOH (methanol); TFA (trifluoroacetic acid); THF (tetrahydrofuran); DMSO (dimethylsulfoxide); EtOAc (ethyl acetate); DCM (dichloromethane); DMF (dimethylformamide); $Et_3N$ (triethylamine); 1,1-carbonyldiimidazole (CDI); isobutylchloroformate (iBuCF); N-hydroxysuccinimide (HOSu); N-hydroxybenztriazole (HOBT); diethyl azodicaboxylate (DEAD); di-tert-butyl dicarbonate (($BOC_2$)O); ethylcarbodiumide hydrochloride (EDC); bis(2-oxo-3-oxazolidinyl) phosphinic chloride (BOP); tert-butyloxycarbonyl (BOC); dicyclohexylcarbodiimide (DCC); benzyloxycarbonyl (Cbz); $NaHCO_3$ (saturated aqueous sodium bicarbonate). All references to ether are to diethyl ether; brine refers to a saturated aqueous solution of NaCl. Unless otherwise indicated, all temperatures are expressed in ° C. (degrees Centigrade). All reactions conducted at room temperature unless otherwise noted.

The $^1$HNMR spectra were recorded on a Varian VXR-300, a Varian Unity-300, or a Varian Unity-400 instrument. Chemical shifts are expressed in parts per million (ppm, $\delta$ units). Coupling constants are in units of hertz (Hz). Splitting patterns are designated as s, singlet; d, doublet; t, triplet; q, quartet; m, multiplet; br, broad.

Low-resolution mass spectra (MS) were recorded on a JOEL JMS-AX505HA, JOEL SX-102 or a SCIEX-APIiii spectrometers. All mass spectra were taken in the positive ion mode under electrospray ionization (ES), chemical ionization (CI), electron impact (EI) or by fast atom bombardment (FAB) methods. Infrared (IR) spectra were obtained on a Nicolet 510 FT-IR spectrometer using a 1-mm NaCl cell. Rotations were recorded on a Perkin-Elmer 241 polarimeter. All reactions were monitored by thin-layer chromatography on 0.25 mm E. Merck silica gel plates (60F-254), visualized with UV light, 7% ethanolic phosphomolybdic acid or p-anisldehyde solution. Flash column chromatography was performed on silica gel (230–400 mesh, Merck).

Products were purified by preparative reversed phase high pressure liquid chromatography (RP-HPLC) using either a Waters Model 3000 Delta Prep equipped with a Delta-pak radial compression cartridge (C18, 300 A, 15 m, 47 mm×300 mm) or a Pharmacia LKB system using Merck Lobar silica or reverse phase C18 columns. Linear gradients were used in all cases and the flow rate was 10–100 mL/minute (t0=5.0 min.). All solvents contained 0.1% TFA. Analytical purity was assessed by RP-HPLC using either a Waters 600E system equipped with a Waters 990 diode array spectrometer (I range 200–400 nM) or a Hewlett Packard series 1050 system equipped with a diode array spectrometer. The stationary phase was either a Dynamax C8 column (25 cm×4.1 mm), a Dynamax 60A C18 column (25 cm×4.6 mm), a Vydac C18 column (5 m, 4.6 mm×250 mm) or a Rainin C18 column (5 m, 4.6 mm×250 mm). The flow rate was 1.0 to 1.5 ml/min. (t0=2.8 or 3.0 min.) and the solvent systems were as described below. Enantiomeric purity was assessed using either a Chiralpak AD column (25 cm×4.6 mm) or a Chiralpak OD column (25cm×4.6 mm) on either a Hewlet Packard series 1050 HPLC system equipped with a diode array spectrometer or on a Supercritical Fluid (SFC) system using $CO_2$/methanol as the mobile phase.

INTERMEDIATES

Intermediate 1

3-(4-benzyloxyphenyl)-2-diazo propionic acid methyl ester

A solution of 2.5 g (8.77 mmol) O-benzyl tyrosine methyl ester, 1.03 g (8.77 mmol) isoamyl nitrite, and 1.57 g (26.2 mmol) glacial acetic acid in chloroform (65 mL) was stirred and refluxed 15 min and then cooled to RT. The solution was concentrated to an oily residue, dissolved in EtOAc (100 mL), and washed with 5% $NaHCO_3$. The organics were then dried ($MgSO_4$), filtered, and concentrated to an oily residue which was chromatographed on silica gel using Hexane/EtOAc (1:1) to yield the title compound. 1H NMR ($CDCl_3$) $\delta$ 7.43–7.31 (m, 5H) 7.14 (d, 2H, J=8.7) 6.90 (m, 2H) 5.03 (s, 2H) 3.76 (s, 3H) 3.56 (s, 2H).

Intermediate 2

2-(4-benzyloxybenzyl)-3-hydroxy-3-phenyl-2,3-dihydro-1H-indole-2-carboxylic acid methyl ester To a refluxing solution of 250 mg (0.84 mmol) of Intermediate 1 and 316 mg (1.59 mmol) 2-aminobenzophenone in toluene (5 mL) was added 1 mg (0.002 mmol, 0.24 equiv) Rhodium(II) acetate dimer. The resulting solution was refluxed for 10 min, cooled to RT, poured into 2N HCl (10 mL), and extracted with EtOAc. The organics were dried ($MgSO_4$), filtered, concentrated, and chromatographed on silica gel using Hexane/EtOAc (3:1) to give the title compound as a yellow oil. 1H NMR ($CDCl_3$) $\delta$ 7.62 (s, 1H) 7.60 (s, 1H) 7.43–7.24 (m, 9H) 7.11–7.09 (d, 1H, J=7.2) 6.9–6.82 (m, 7H) 5.01 (s, 2H) 3.77 (s, 3H) 2.66 (s, 1H) 2.45 (ABq, 2H, J AB=13.5, DnAB=40.2).

Intermediate 3

2-(3-Benzoyl-thiophen-2-yl-amino)-3-(4-benzyloxy-phenyl)-propionic acid methyl ester 3 mg (0.0067 mmol) rhodium(II) acetate dimer was added to stirred solution of 300 mg (1.01 mmol) Intermediate 1 (Kawamatsu, Y. at al. Arzneim.-Forsch. 1980, 30(4), 585–9) and 110 mg (0.57 mmol) (2-amino-thiophen-3-yl)-phenyl-methanone (Robba, M., et al. Bull. Soc. Chim. Fr. 1974, 12(2), 2864–70.) in 10 mL toluene at 80° C. The mixture was warmed to reflux for 5 min, then cooled to room temperature. The solvent was removed under reduced pressure, and the residue was purified by flash chromatography using $CH_2Cl_2$ (neat) as eluent to yield 120 mg of the title compound; TLC($CH_2Cl_2$): Rf=0.40).

Intermediate 4

2-(2-Benzoyl-thiophen-3-yl-amino)-3-(4-benzyloxy-phenyl)-propionic acid methyl ester The title compound (280 mg) was preapred from 600 mg (2.02 mmol) of Intermediate 1 (Kawamatsu, Y. at al. Arzneim.-Forsch. 1980, 30(4), 585–9) and 203 mg (1.0 mmol) (3-Amino-thiophen-2-yl)-phenyl-methanone (Kiehne, H. (Bayer A. G.) Ger. Offen. 1945964 (Mar. 25, Intermediate 5

N-2-(N-methyl amino ethanol)-1,3-benzoxazole

To a stirred solution of 10 g (133 mmol) N-methyl aminoethanol at 0° C. was dropwise added 10 g (65.2 mmol) 2-chlorobenzoxazole. The resulting solution stirred for 1 h and was diluted with water (250 mL) and extracted with EtOAc. The organics were washed with brine, dried (MgSO$_4$), filtered, and concentrated to yield 12.2 g of a tan oil which solidified on standing, m.p. 56–58° C.

Intermediate 6

N-2-[(N-methyl aminoethyl-1-methylsulfonate)-1,3-benzoxazole]

To a stirred solution of 22 g (114.6 mmol) of Intermediate 5, and 14.43 g (126 mmol) rnethanesulfonyl chloride in dichloromethane (100 mL) at 0° C. was dropwise added 17.6 mL (126.3 mmol) TEA. The resulting suspension was stirred for 1 h and diluted with water (200 mL) and 1M H$_3$PO$_4$ solution (100 mL). The organic phase was separated, dried (MgSO$_4$), filtered, and concentrated to yield 20 g of a white solid, m.p. 94–96° C.

Intermediate 7

2-amino-3-{4-[2-(benzoxazol-2-yl-methyl-amino)-ethoxy]-phenyl}-propionic acid methyl ester To a stirred solution of 3.61 g (18.5 mmol) of (S)-tyrosine methyl ester and 0.81 g (20.4 mmol) of sodium hydride (60% suspension in mineral oil) in 50 mL of DMF at RT was added 5.0 g (18.5 mmol) of Intermediate 6. The resulting solution was heated to 100° C. for 2 h. After cooling to RT, the solution was quenched with water and extracted with EtOAc. The combined organics were dried (MgSO$_4$) and solvent removed in vacuo. The residue was purified by silica gel chromatography using hexane/EtOAc (gradient of 3:7 to 0:1) as eluent to give 1.45 g (21% yield) of the title compound: low resolution MS (ES) m/e 370 (MH.

Intermediate 8

2(S)-amino-3-{4-[2-(benzoxazol-2-yl-methyl-amino)-ethoxy]-phenyl}-propionic acid 13.5 mL (13.5 mmol) 1 N sodium hydroxide solution was added to a stirred solution of 5.00 g (13.5 mmol) of Intermediate 7 (Faller, A. et. al. WO 94/29285) in 25 mL MeOH, and the resulting solution was stirred for 12 h at room temperature. The MeOH was removed under reduced pressure, and the residue was diluted with 25 mL water. The solution was extracted with 25 mL ether three times, then the aqueous phase was acidified using 14 mL 1 n hydrochloric acid. The resulting white solid was filtered, washed with 3×25 mL water and dried under reduced pressure to yield 4.02 g of the title compound; low resolution MS (API+) m/e 356 (MH+).

Intermediate 9

2-diazo-3-{4-[2-(benzoxazol-2-yl-methyl-amino)-ethoxy]-phenyl}-propionic acid methyl ester Reaction was performed behind a blast shield. To a stirred solution of 1.45 g of Intermediate 7 and 0.7 mL (11.8 mmol) of glacial acetic acid in 40 mL of chloroform was added 0.5 mL (3.93 mmol) of isoamyl nitrite. The resulting solution was heated to 60° C. for 0.25 h. The solution under went a colour change to orange/brown after heating. The solution was cooled to RT and extracted with water and then washed with a saturated solution of sodium bicarbonate. The organics were then dried (MgSO$_4$) and the solvent removed in vacuo to quantitatively yield the title compound which was used directly without further purification: low resolution MS (ES) m/e 381 (MH+), 353.

Intermediate 10

3-{4-[2-(benzoxazol-2-yl-methyl-amino)ethoxy]-phenyl}-2-(2-benzoyl-phenylamino)-propionic acid methyl ester The title compound (110 mg) was prepared from 0.17 g (0.5 mmol) of Intermediate 9 and 0.11 g (0.5 mmol) of 2-amino benzophenone according to the method of Intermediate 3 followed by purification via silica gel chromatography using EtOAc/hexane (gradient of 3:7 to 1:1): low resolution MS (ES) m/e 550 (MH+).

Intermediate 11

3-{4-[2(benzoxazol-2-yl-methyl-amino)-ethoxy]-phenyl}-2-(2-benzoyl4-methyl-phenylamino)-propionic acid methyl ester The title compound (100 mg) was prepared from 0.13 g (0.3 mmol) of Intermediate 9 and 0.10 g (0.5 mmol) of 2-amino-5-methyl benzophenone according to the method of Intermediate 3 followed by purification via silica gel chromatography using EtOAc/hexane (gradient of 3:7 to 1:1): low resolution MS (ES) m/e 564 (MH+).

Intermediate 12

3-{4-[2-(Benzoxazol-2-yl-methyl-amino)-ethoxy]-phenyl}-2-(2-cyclohexanecarbonyl-phenylamino)-propionic acid methyl ester The title compound (61 mg) was prepared from 125 mg (0.33 mmol) of Intermediate 11 and 87.9 mg (0.46 mmol, 1.4 equiv.) of (2-amino-phenyl)-cyclohexyl-methanone according to the method of Intermediate 3 followed by purification via silica gel flash column chromatography using hexane/EtOAc 3/1 to 1/1 as eluent: low resolution MS (API) m/e 556.3 (MH+).

Intermediate 13

3-{4-[2-Benzoxazol-2-yl-methyl-amino)-ethoxy]-phenyl}-2-(2-benzoyl-thiophen-3-ylamino)-propionic acid methyl ester The title compound (130 mg) was prepared from 200 mg (0.53 mmol) of Intermediate 9 and 149 mg (0.74 mmol, 1.4 equiv.) of (3-amino-thiophen-2-yl)-phenyl-methanone according to the method of Intermediate 3 followed by purification via silica gel flash column chromatography using hexane/EtOAc 3/1 to 1/1 as eluent: low resolution MS (API) m/e 556.2 (MH+).

Intermediate 14

3-{4-[2-(Benzoxazol-2-yl-methyl-amino)-ethoxy]-phenyl}-propionic acid methyl ester To a stirring solution of 1.40 g (7.77 mmol) of methyl 3-(4-hydroxy-phenyl}-propionic acid methyl ester in 15.5 mL of DMF at 0° C. was added 310.7 mg (7.77 mmol, 1.0 equiv) of sodium hydride 60% dispersion in oil. The resulting solution was stirred 5 min, and 2.31 g (8.55 mmol, 1.1 equiv.) of Intermediate 6 was added. The resulting solution was allowed to warm to rt and stirred for 19 h, then quenched with $H_2O$. The reaction mixture was extracted with EtOAc. The organic layer was dried ($MgSO_4$), and the solvents removed in vacuo. Purification by silica gel flash column chromatography using hexane/EtOAc 1/1 as eluent afforded 1.61 g of the title compound as a clear oil: low resolution MS (ES) m/e 355 (MH+).

Intermediate 15

3-{4-[2-(Benzoxazol-2-yl-methyl-amino)-ethoxy]-phenyl}-2-benzyl-propionic acid methyl ester To a stirring solution of 502.2 mg (1.42 mmol) of Intermediate 14 in 10 mL of THF at −78° C. was added 1.70 mL (1.70 mmol, 1.2 equiv) of a 1.0 M solution of NaHMDS in THF. The resulting solution was stirred 15 min, and 315.1 mg (1.84 mmol, 1.3 equiv.) of benzyl bromide in 4.0 mL of THF was added. The resulting solution was allowed to warm to rt in the bath and stirred for 4 h, then quenched with $H_2O$. The reaction mixture was extracted with EtOAc. The organic layer was dried ($MgSO_4$), and the solvents removed in vacuo. Purification by silica gel flash column chromatography using hexane/EtOAc 3/2 as eluent afforded 90.8 mg of the title compound as a clear oil: low resolution MS (ES) m/e 445 (MH+).

Intermediate 16

3-{4-[2-Benzoxazol-2-yl-methylamino)ethoxy]-phenyl}-2-(2-bromo-benzyl)-propionic acid methyl ester To a stirring solution of 1.00 g (2.82 mmol) of Intermediate 15 in 10 mL of THF at −78° C. was added 2.26 mL (3.39 mmol, 1.2 equiv) of a 1.5 M solution of LDA in cyclohexane. The resulting solution was stirred 15 min, and 846.3 mg (3.39 mmol, 1.2 equiv.) of 2-bromo-benzyl bromide in 4.0 mL of THF was added. The resulting solution was allowed to warm to rt in the bath and stirred for 4 h, then quenched with $H_2O$. The reaction mixture was extracted with EtOAc. The organic layer was dried ($MgSO_4$), and the solvents removed in vacuo. Purification by silica gel flash column chromatography using hexane/EtOAc 3/2 as eluent afforded 318.5 mg of the title compound as a clear oil: low resolution MS (ES) m/e 523 (MH+).

Intermediate 17

{4-[2-(methyl-pyridin-2-yl-amino)-ethoxy]-phenyl}-MeOH

Sodium borohydride (0.5 g, 13.2 mmol) was added to stirred solution of 5.12 g (20 mmol) 4-[2-(methyl-pyridin-2-yl-amino)-ethoxy]-benzaldehyde (Cantello, B. C. C. et al. J. Med. Chem. 1994, 37, 3977–85) in 50 mL anhydrous ethyl alcohol. The mixture was stirred at 20° C. for 2 h. 10 mL water was added to the mixture, and it was stirred for 30 min. The ethyl alcohol was removed under reduced pressure, 50 mL water and 100 mL diethyl ether was added to the residue. The mixture was stirred for 30 min, then an additional amount of 100 mL ether was added. The phases were separated, the organic phase was extracted with 100 mL water three times, dried with anhydrous magnesium sulfate, then filtered. The filtrate was concentrated under reduced pressure to provide 5.06 g of the title compound: TLC (Hexane/EtOAc(1:1)): Rf=0.50).

Intermediate 18

[2-(4-Bromomethyl-phenoxy)-ethyl]-methyl-pyridin-2-yl-amine

Triphenyl phosphine dibromide (422 mg, 1.0 mmol) was added to a stirred solution of 258 mg (1 mmol) of Intermediate 17 in 10 mL methylene chloride at 5° C. The mixture was stirred for 30 min, and it was allowed to warm up to 20° C., then an additional 422 mg (1 mmol) triphenyl phosphine dibromide was added in one portion. The mixture was stirred for an additional 30 min, then 20 mL methylene chloride was added, and the solution was cooled to 0° C. 30 mL saturated sodium bicarbonate aq. solution was added to the mixture, and then it was stirred for 30 min. The phases were separated, the aqueous phase was extracted with 20 mL methylene chloride twice, then the organic phases were combined, dried with anhydrous magnesium sulfate and filtered. The filtrate was concentrated under reduced pressure while the temperature was kept below 20° C. The residue was purified by flash chromatography using hexane/EtOAc(4:1) as eluent. The fractions were concentrated under reduced pressure at 15–20° C. to yield 260 mg of the title compound: TLC (Hexane/EtOAc(1:1)): Rf=0.90).

Intermediate 19

2-Benzhydrylideneamino-3-{4-[2-(methyl-pyridin-2-yl-amino)-ethoxy]-phenyl}-propionic acid ethyl ester A solution of 4.0 g (71.4 mmol) potassium hydroxide in 4 mL water was added to a cooled (0° C.) solution of 3.50 g (10.9 mmol) of Intermediate 18, 3.70 g (13.8 mmol) N-(Diphenylmethylene)-glycine ethyl ester and 4.3 g (16.1 mmol) tetrabutylammonium hydrogen sulfate over 5 min. The resulting yellow mixture was stirred for 1 hour at 5–10° C., then 10 g anhydrous magnesium sulfate was added, and the suspension was filtered. The filtrate was concentrated under reduced pressure without using external heat. The residue was transferred to a silica gel packed column which was prewashed with a solvent mixture containing Hexane/EtOAc/$NEt_3$(40:10:1). Purification by flash chromatography using hexane/EtOAc (4:1) then hexane/EtOAc (2:1) resulted in 5.66 g of the title compound: TLC (Hexane/EtOAc(5:1)): Rf=0.30).

Intermediate 20

2-Amino-3-{4-[2-(methyl-pyridin-2-yl-amino)-ethoxy]-phenyl}-propionic acid ethyl ester To a stirred solution of 5.66 g (11.1 mmol) of Intermediate 19 in 200 mL ethanol, 20 mL conc. hydrochloric acid was added at 20° C. over 15 min, and the mixture was stirred at room temperature for one hour. 400 mL saturated sodium bicarbonate solution was added dropwise to the solution, and when the carbon dioxide evolution stopped 200 mL methylene chloride was added. The phases were separated, and the aqueous phase was extracted with 100 mL methylene chloride three times. The organic phases were combined, dried with magnesium sulfate, and filtered. The filtrate was concentrated under reduced pressure, and the residue was purified by flash chromatography using hexane/EtOAc(1:1), EtOAc(neat), then EtOAc/EtOH (9:1) solvent mixtures as eluent to yield 3.19 g of the title compound: TLC (Hexane/EtOAc(1:1)): Rf=0.10).

Intermediate 21

3-Hydroxy-2-{4-[2-(methyl-pyridin-2-yl-amino)-ethoxy]-benzyl}-3-phenyl-2,3-dihydro-1H-indole-2-carboxylic acid ethyl ester The title compound (310 mg) was prepared from 291 mg (0.85 mmol) of Intermediate 20 according to the method of Intermediate 1 followed by reaction with 197 mg (1 mmol) 2-aminobenzophenone according to the method of Intermediate 3 followed by purification via silica gel flash chromatography using hexane-EtOAc(4:1) then hexane:EtOAc(1:1) as eluent: low resolution MS (ESP+) m/e 524 (MH+).

Intermediate 22

2-Amino-3-{4-[-(methyl-pyridin-2-yl-amino)-ethoxy]-phenyl}-propionic acid

To a stirred solution of 160 mg (0.46 mmol) of Intermediate 20 in 3.2 mL MeOH, 112 mg (2 mmol) potassium hydroxide was added in 1 mL water. The mixture was stirred 5 h at 20° C., the n the MeOH was removed under reduced pressure. 240 mg (2 mmol) sodium bisulfate was added to the mixture in 5 mL water and the slurry was stirred at 20° C. for 30 min. The precipitate was filtered, and washed with 5 mL water three times. The filtrate was adjusted to pH=5 using saturated sodium bicarbonate solution, and the precipitate was filtered, and washed with 5 mL water three times. The solids were combined and dried under reduced pressure to yield 115 mg of the title compound: TLC (EtOH(neat)): Rf=0.05).

Intermediate 23

(S)-2-(2-Benzoyl-phenylamino)-3-(4-hydroxy-phenyl)-propionic acid methyl ester

A stirred mixture of 92 g (0.45 mol) 2-benzoyl-cyclohexanone, (Denny, W. A. et. al. J. Med. Chem. 1978, 21(5), 430–7) 78 g (0.40 mol) L-Tyrosine methyl ester, 17.0 g Palladium on activated carbon (10%) was refluxed for 2 h in 1 L anisole while the resulting water was removed by a Dean-Stark apparatus. The mixture was cooled to 80° C. and the Pd/C was filtered, and washed with 50 mL anisole three times. The mixture was cooled to 40° C., 1 L hexane was added and kept at −20° C. for 48 h. The solid was filtered, washed with 200 mL hexane five times to yield 89.0 g crude (S)-2-(2-Benzoyl-phenylamino)-3-(4-hydroxy-phenyl)-propionic acid methyl ester. This solid was mixed with 220 mL of MeOH, and the slurry was refluxed for 30 min. The mixture was cooled to 0° C., the product was filtered and washed with 50 mL cold (−20° C.) MeOH twice, then dried under reduced pressure to yield 67.4 g the of the title compound. mp 185–6° C.; low resolution MS (ESP+) m/e 376 (MH+).

Intermediate 24

2-(N-tert-butoxycarbonyl-N-methyl-amino)ethanol

A solution of 10 g (0.133 mol) of 2-(methylamino)ethanol in 266 mL of $CH_2Cl_2$ at 25° C. was treated with 29.1 g (0.133 mol) of $BOC_2O$. After stirring for 3 h, the reaction was concentrated in vacuo. Purification by silica gel chromatography eluting with hexanes/EtOAc (1:1Æ 1:2Æ 1:4) gave rise to 23.3 g (100%) of title compound as a clear oil: low resolution MS (ES) m/e 198 (MNa+).

Intermediate 25

2(S)-(2-benzoyl-phenylamino)-3-{4-[2-(tert-butoxycarbonyl-methyl-amino)-ethoxy]-phenyl}-propionic acid methyl ester A solution of 1.5 g (3.99 mmol) of Intermediate 23, 770 mg (4.39 mmol, 1.1 equiv) of Intermediate 24 and 1.57 g (5.99 mmol, 1.5 equiv) of triphenylphosphine in 40 mL of THF at 25° C. was treated dropwise with 0.944 mL (5.99 mmol, 1.5 equiv) of DEAD. The reaction was stirred at 25° C. for 48 h then concentrated in vacuo. The residue was purified by silica gel flash column chromatography using hexanes/EtOAc (2:1) as eluent to give 1.37 g (65%) of title compound as a viscous yellow oil: low resolution MS (ES) m/e 555 (MNa+), 533 (MH+).

Intermediate 26

2(S)-(2-benzoyl-phenylamino)-3-{4-[2-(methyl-pyridin-2-yl-amino)-ethoxy]-phenyl}-propionic acid methyl ester A solution of 2.56 g (4.81 mmol) of Intermediate 25 in 56 mL of $CH_2Cl_2$ at 25° C. was treated with 56 mL (0.73 mol, 152 equiv) of TFA. After stirring for 30 min, the solution was neutralized with saturated $NaHCO_3$ followed by solid $NaHCO_3$ and extracted with $CH_2Cl_2$. The combined organics were dried ($Na_2SO_4$), filtered, and concentrated in vacuo. The crude amine was used immediately in the next reaction. A solution of 2.08 g (4.81 mmol) of the crude amine from above in 480 mL of 2-fluoropyridine was allowed to reflux for 16 h then concentrated in vacuo. Purification by silica gel flash column chromatography using hexanes/EtOAc (2:1) as eluent provided 1.85 g (76%) of the title compound as a yellow oil: low resolution MS (Cl) m/e 511 (MH+), 510 (M+).

Intermediate 27

3-{4-[2-(benzoxazol-2-yl-methyl-amino)-ethoxy]-phenyl}-2(S)-(2-benzoyl-phenylamino)-propionic acid methyl ester A solution of 319 mg (0.60 mmol) of Intermediate 25 in 7 mL of $CH_2Cl_2$ at 25° C. was treated with 7 mL (90.9 mmol, 152 equiv) of TFA. After stirring for 30 min, the solution was neutralized with saturated $NaHCO_3$ and extracted with $CH_2Cl_2$. The combined organics were dried ($Na_2SO_4$), filtered, and concentrated in vacuo. To a solution of 259 mg (0.60 mmol) of the above amine in 6 mL of THF at 25° C. was added 0.250 mL (1.80 mmol, 3 equiv) of $Et_3N$ followed by 0.103 mL (0.90 mmol, 1.5 equiv) of 2-chlorobenzoxazole. After stirring fro 24 h, the reaction was diluted with EtOAc, poured into saturated $NaHCO_3$, and extracted with EtOAc. The combined organics were dried ($Na_2SO_4$), filtered, and concentrated in vacuo. Purification by silica gel flash column chromatography eluting with hexanes/EtOAc (2:1Æ 1:1) provided 244 mg (74%) of title compound as a yellow solid: low resolution MS (ES) m/e 572 (MNa+), 550 (MH+).

Intermediate 28

Toluene-4-sulfonic acid 1-benzoxazol-2-yl-pyrrolidin-2S-ylmethyl ester

To a solution of 1.0 g (9.89 mmol) of L-prolinol in 19.8 mL of THF at 0° C. was added 3.0 mL (21.8 mmol, 2.2 equiv) of $Et_3N$ followed by 1.24 mL (10.9 mmol, 1.1 equiv) of 2-chlorobenzoxazole. The reaction was filtered washing with THF, and the filtrate was concentrated in vacuo. The residue was dissolved in 10 mL of pyridine and treated with 1.9 g (9.89 mmol, 1 equiv) of p-toluenesulfonyl chloride. After stirring for 24 h, the reaction was poured into $H_2O$, and the product was extracted with EtOAc. The combined organics were dried ($MgSO_4$), filtered, and concentrated in vacuo.

Purification by silica gel flash column chromatography eluting with hexanes/EtOAc (2:1) gave rise to 2.76 g (75%) of title compound as a white solid: 1H NMR (CDCl$_3$, 300 MHz) d 7.67 (d, 2H, J=12.3), 7.33–6.94 (m, 6H), 4.46 (dd, 1H, J=7.8, 16.2), 4.30–4.10 (m, 2H), 3.60 (m, 2H), 2.16 (s, 3H), 2.25–1.90 (m, 4H); low resolution MS (ES) m/e 395 (MNa+), 373 (MH+); Anal. (C$_{19}$H$_{20}$N$_2$O$_4$S) Calcd. C, 61.27; H, 5.41; N, 7.52; S, 8.61 Found C, 61.20; H, 5.46; N, 7.46; S, 8.55; TLC (hexanes/EtOAc (2:1)): Rf=0.28.

Intermediate 29

Toluene-4-sulfonic acid 1-benzoxazol-2-yl-pyrrolidin-2R-ylmethyl ester

The title compound (1.6 g) was prepared from 1.0 g (9.89 mmol) of D-prolinol according to the method of Intermediate 28 followed by purification via trituration of the solid with hexanes/EtOAc (1:1): low resolution MS (ES) m/e 395 (MNa+), 373 (MH+).

Intermediate 30

3-[4-(1-benzoxazol-2-yl)-pyrrolidin-2S-yl-methoxy)-phenyl]-2-(2-benzoyl-phenylamino)-propionic acid methyl ester A solution of 2.0 g (5.33 mmol) of Intermediate 23 and 1.98 g (5.33 mmol, 1 equiv) of Intermediate 28 in 21.3 mL of DMF at 25° C. under nitrogen was treated with 2.08 g (6.4 mmol, 1.2 equiv) of Cs$_2$CO$_3$. The reaction was heated to 80° C. and stirred 24 h. Upon cooling to 25° C., the reaction was poured into H$_2$O and hexanes/EtOAc (1:1) and extracted with hexanes/EtOAc (1:1). The combined organics were dried (Na$_2$SO$_4$), filtered, and concentrated in vacuo. Purification by silica gel flash column chromatography eluting with hexanes/EtOAc (1.5:1) gave rise to 2.26 g (74%) of the title compound as a yellow solid: low resolution MS (ES) m/e 598 (MNa+), 576 (MH+).

Intermediate 31

3-[4-(1-benzoxazol-2-yl)-pyrrolidin-2R-yl-methoxy)-phenyl]-2-(2-benzoyl-phenylamino)-propionic acid methyl ester The title compound (285 mg) was prepared from 0.25 g (0.67 mmol) of Intermediate 23 and 0.248 g (0.67 mmol, 1 equiv) of Intermediate 29 according to the method of Intermediate 30 followed by purification via silica gel flash column chromatography eluting with hexanes/EtOAc (1.5:1): low resolution MS (ES) m/e 598 (MNa+), 577 (MH+).

Intermediate 32

1-Benzoxazol-2-yl-pyrrolidin-3-ol

To a stirring solution of 5.1 mL (44.6 mmol) of 2-chlorobenzoxazole in 35 mL of THF at 0° C. was added 4.28 g (49.0 mmol, 1.1 equiv.) of (R)-3-hydroxypyrrolidine and 4.42 mL (32 mmol, 0.72 equiv.) of triethylamine. The resulting solution was stirred 12 h at RT, the precipitate was filtered, washed with THF (3×5 mL), and the filtrate concentrated in vacuo. Purification by silica gel flash column chromatography using hexane/EtOAc 1/1 to EtOAc as eluent afforded 3.74 g of the title compound: low resolution MS (ESP) m/e 205 (MH+).

Intermediate 33

Methanesulfonic acid 1-benzoxazol-2-yl-pyrrolidin-3-yl ester

To a stirring solution of 3.74 g (18.3 mmol) of Intermediate 32 in 30 mL of pyridine was added 1.37 mL (17.8 mmol, 0.93 equiv.) of methanesulfonyl chloride. The resulting solution was stirred 3 h at RT then quenched into ice water (100 mL). The reaction mixture was extracted with DCM (3×50 mL). The combined organic extracts were washed successively with saturated NaHCO$_3$, brine, dried (MgSO$_4$), and the solvents removed in vacuo. Purification by trituration with isopropyl alcohol afforded 3.71 g of the title compound: low resolution MS (ESP) m/e 283 (MH+).

Intermediate 34

3-[4-(1-Benzoxazol-2-yl-pyrrolidin-3-yloxy)-phenyl]-2-(2-benzoyl-phenylamino)-propionic acid methyl ester The title compound (156 mg) was prepared from 188 mg (0.50 mmol) of Intermediate 23 and 155 mg. (0.55 mmol, 1.1 equiv.) of Intermediate 33 according to the method of Intermediate 30 followed by purification via silica gel flash column chromatography using hexane/EtOAc 3/1 to 1/1 as eluent: low resolution MS (ESP) m/e 562 (MH+).

Intermediate 35

2(S)-(2-Benzoyl-phenylamino)-3-{4-[2-(5-methyl-2-phenyl-oxazol-4-yl)-ethoxy]-phenyl}-propionic acid methyl ester A solution of 0.25 g of Intermediate 23 (0.67 mmol), 0.20 g of 2-(5-methyl-2-phenyloxazol-4-yl)ethanol (0.98 mmol, 1.5 equiv, Maybridge), and 0.35 g of triphenylphosphine (1.33 mmol, 2.0 equiv) in 10 mL of anhydrous THF was cooled to 0° C. and treated with 0.21 mL of diethyl azodicarboxylate (1.33 mmol, 2.0 equiv). The reaction was allowed to warm to RT for 18 h, concentrated in vacuo purified by flash chromatography on silica gel (7:3 hexane:EtOAc). This afforded 0.26 g (70%) of the title compound as a yellow foam: mp 55–60° C.; low resolution MS (ES) m/e 561 (MH+).

Intermediate 36

2-(2-Benzoyl-phenylamino)-3-{4-[2-(4-chorophenyl)-thiazol-4ylmethoxy]-phenyl}-propionic acid methyl ester The title compound (210 mg) was prepared from 150 mg (0.40 mmol) of Intermediate 23 and 107 mg (0.44 mmol, 1.1 equiv) of 4-chloromethyl-2-(4-chlorophenyl)thiazole according to the method of Intermediate 30 followed by purification via silica gel flash column chromatography using hexane/EtOAc 8/1 as eluent: low resolution MS (FAB)m/e 584 (MH+), 583 (M+).

Intermediate 37

2-(2-Benzoyl-phenylamino)-3-[4-(2-hydroxy-ethoxy)-phenyl]-propionic acid methyl ester A suspension of 400 mg (1.06 mmol) of Intermediate 23, 930 mg (10.60 mmol, 10.0 equiv) of ethylene carbonate, and 175 mg (1.28 mmol, 1.2 equiv) of K$_2$CO$_3$ in 10 mL of DMF was heated to 95° C. for 3 h with stirring. The reaction mixture was cooled to RT, poured into 100 mL of Et$_2$O and extracted with H$_2$O (2×50 mL). The organic layer was separated, dried (MgSO$_4$), and the solvents removed in vacuo. Purification of the yellow solid by silica gel flash column chromatography using hexane/EtOAc 2/1 as eluent afforded 440 mg of the title compound as a clear yellow oil: 1H NMR (CDCl$_3$, 300 MHz) δ 8.90 (d, 1H, J=7.5), 7.60 (m, 2H), 7.52–7.31 (m, 5H), 7.20 (dd, 2H, J=2.2, 6.5), 6.83 (dd, 2H, J=2.2, 6.5), 6.60 (m, 2H), 4.51 (s, 1H), 4.38 (dd, 1H, J=5.9, 5.9), 4.04 (m, 2H), 3.94 (m, 2H), 3.70 (s, 3H), 3.17 (m, 2H).

Intermediate 38

2-(2-Benzoyl-phenylamino)-3-[4-(2-methanesulfonyloxy-ethoxy)-phenyl]-propionic acid methyl ester To a stirring solution of 350 mg (0.83 mmol) of Intermediate 37 in 8 mL of THF at RT was added 0.23 mL (1.67 mmol, 2.0 equiv) of $Et_3N$, followed by 0.13 mL (1.67 mmol, 2.0 equiv) of methanesulfonyl chloride. The resulting mixture was stirred 90 min at RT then heated to 45° C. for 1 h. The reaction mixture was cooled to RT, poured into 50 mL of $Et_2O$ and extracted with $H_2O$ (2×50 mL). The organic layer was separated, dried ($K_2CO_3$), and the solvents removed in vacuo to afford 430 mg of the title compound as a clear yellow oil, which was used without further purification: low resolution MS (Cl)m/e 499 (MH+), 498 (M+).

Intermediate 39

3-{4-[2-(2-Amino-phenylamino-ethoxy]-phenyl}-2-(2-benzoyl-phenylamino)-propionic acid methyl ester To a stirring solution of 425 mg (0.85 mmol) of Intermediate 38 in 5 mL dry DMF at RT was added 590 mg (4.27 mmol, 5.0 equiv) of $K_2CO_3$ and 462 mg (4.27 mmol, 5.0 equiv) of 1,2-phenylenediamine. The resulting solution was heated to 80° C. for 17 h. The reaction mixture was cooled to RT, poured into 50 mL of $Et_2O$ and extracted sequentially with 1 N HCl (1×20 mL), $NaHCO_3$ (1×20 mL), and $H_2O$ (2×50 mL). The organic layer was separated, dried ($K_2CO_3$), and the solvents removed in vacuo. Purification of the crude material by silica gel flash column chromatography using hexane/EtOAc 2/1 as eluent afforded 90 mg of the title compound as a clear yellow oil which discolored upon standing and should be used immediately after purification: low resolution MS (Cl)m/e 511 (MH+), 510 (M+).

Intermediate 40

3-[4-(2-Benzoimidazol-1-yl-ethoxy)-phenyl]-2-(2-benzoyl-phenylamino)-propionic acid methyl ester To a stirring solution of 90 mg (0.18 mmol) of Intermediate 39 in 3 mL of triethyl orthoformate was added 5 mg of p-toluenesulfonic acid, which produced a white precipitate. This suspension was heated to 80° C. for 2 h with stirring, during which much of the precipitate disappeared. The reaction mixture was cooled to RT, poured into 20 mL of $Et_2O$/dichloromethane 1:1 and extracted with 1 N NaOH (1×20 mL). The organic layer was washed with $H_2O$ (1×20 mL), separated, dried ($MgSO_4$), and the solvents removed in vacuo. Purification of the crude product by silica gel flash column chromatography using EtOAc as eluent afforded 94 mg of the title compound as a clear yellow oil: low resolution MS (Cl)m/e 521 (MH+), 520 (M+).

Intermediate 41

1-(3-iodo-phenyl)-butane-1,3-dione 4.0 g (100 mmol) sodium hydride (60%) was added to a stirred solution of 13.8 g (50 mmol) 3-iodobenzoic acid ethyl ester and 12 mL (160 mmol) acetone in 25 mL anhydrous THF. The mixture was stirred at 25° C. for 20 min, then slowly warmed to 30° C. An exothermic reaction started, and the temperature was kept below 30° C. with water bath. After 1 h the hydrogen evolution stopped, and the mixture was cooled to 5° C., and quenched with 150 mL 3% aqueous hydrochloric acid. 200 mL ether was added to the solution, then the phases were separated. The organic phase was washed with 100 mL water three times, dried with anhydrous magnesium sulfate and filtered. The filtrate was concentrated under reduced pressure. The residue was mixed with 200 mL hexane, then the precipitate was filtered, and washed with 50 mL hexane three times. The filtrate was concentrated under reduced pressure, and purified by silica gel flash chromatography with hexane(neat), then hexane-EtOAc(4:1) as eluents to yield 7.0 g of the title compound, which was crystallized from hexane at −40° C.; TLC (Hexane-EtOAc(4:1)): Rf=0.65).

Intermediate 42

[2-(4-methoxy-phenyl)-5-methyl-oxazol-4-yl]-acetic acid methyl ester

A mixture of 725 mg (4.80 mmol) of 4-methoxybenzamide and 1.0 g (4.80 mmol) of methyl 4-bromo-3-oxo-pentanoate was heated neat at 120° C. for 2 h. The resulting dark slurry was cooled to RT, diluted with 2 mL of dichloromethane and purified by silica gel flash column chromatography using hexane/EtOAc 3/1 as eluent to afford 189 mg of the title compound as a yellow solid: low resolution MS (FAB)m/e 285 (MH$^+$), 284 (M$^+$).

Intermediate 43

2-[2-(4-methoxy-phenyl)-5-methyl-oxazol-4-yl]-ethanol

To a stirring solution of 185 mg (0.71 mmol) of Intermediate 42 in 5 mL of THF at 0° C. was added 0.71 mL (0.71 mmol, 1.0 equiv) of a 1.0 M solution of $LiAlH_4$ in THF. The resulting solution was stirred at RT for 45 min then cooled to 0° C. And quenched by careful addition of 0.027 mL of $H_2O$, followed by addition of 0.027 mL of 15% NaOH and 0.080 mL of $H_2O$. The resulting slurry was filtered to remove the solids and the filtrate was concentrated in vacuo to afford 164 mg of the title compound as a light yellow oil: $^1$H NMR ($CDCl_3$, 400 MHz) δ 6 7.92 (d, 2H, J=8.8), 6.94 (d, 2H, J=8.8), 3.92 (dt, 2H, J=5.7, 11.5), 3.86 (s, 3H), 3.35 (t, 1H, J=6.2), 2.71 (t, 2H, J=5.7), 2.32 (s, 3H).

Intermediate 44

2(S)-(2-benzoyl-phenylamino)-3-{4-[2-(5-methyl-2-(4-methoxy)-phenyl-oxazol-4-yl)-ethoxy]-phenyl}-propionic acid methyl ester To a stirring solution of 195 mg (0.74 mmol, 1.05 equiv) of triphenylphosphine in 5 mL of THF at 0° C. was added dropwise 117 mg (0.67 mmol, 0.95 equiv) of diethyl azodicarboxylate. The resulting light yellow solution was stirred at RT for 5 min then added dropwise to a solution of 265 mg (0.71 mmol) of Intermediate 23 and 165 mg (0.71 mmol) of Intermediate 43 in 5 mL of THF. The resulting solution was stirred 18 h at RT and then the solvent was removed in vacuo. The residue was stirred vigorously for 1 h in 30 mL of 2:1 diethyl ether/1 N LiOH biphasic solution to effect selective removal of residual Intermediate 23. The layers were separated and the organic layer washed with $H_2O$, dried ($MgSO_4$), and solvent removed in vacuo. Purification of the yellow solid by silica gel flash column chromatography using hexane/EtOAc 2/1 as eluent afforded 200 mg of the title compound as a yellow solid: low resolution MS (FAB)m/e 591 (MH$^+$).

Intermediate 45

[2-(4-fluoro-phenyl)-5-methyl-oxazol-4-yl]-acetic acid methyl ester

A solution of 667 mg (4.80 mmol) of 4-fluorobenzamide and 1.0 g (4.80 mmol) of methyl 4-bromo-3-oxo-pentanoate in 6 mL of dry toluene was heated at 120° C. for 16 h. The resulting dark slurry was cooled to RT, diluted with 10 mL of EtOAc, and washed with NaHCO$_3$ (1×10 mL). The organic layer was separated, dried (MgSO$_4$), and the solvents removed in vacuo. Purification of the material by silica gel flash column chromatography using hexane/EtOAc 4/1 as eluent to afford 308 mg of the title compound as a clear oil: $^1$H NMR (CDCl$_3$, 400 MHz) δ 7.97 (m, 2H), 7.11 (m, 2H), 3.73 (s, 3H), 3.56 (s, 2H), 2.36 (s, 3H).

Intermediate 46

2-[2-(4-fluoro-phenyl)-5-methyl-oxazol-4-yl]-ethanol

The title compound was prepared from 300 mg (1.20 mmol) of intermediate 45 by the procedure for preparing Intermediate 43 to afford 248 mg of the title compound as a white solid: low resolution MS (FAB)m/e 221 (M$^+$).

Intermediate 47

2(S)-(2-benzoyl-phenylamino)-3-{4-[2-(5-methyl-2-(4-fluoro)-phenyl-oxazol-4-yl)-ethoxy]-phenyl}-propionic acid methyl ester The title compound (298 mg) was prepared from 407 mg (1.08 mmol) of Intermediate 23 and 240 mg (1.08 mmol) of Intermediate 46 according to the method of Intermediate 44 followed by purification via silica gel flash column chromatography using hexane/EtOAc 2/1 as eluent: low resolution MS (FAB)m/e 580 (MH$^+$), 579 (M$^+$).

Intermediate 48

2-(5-methyl-1-phenyl-1H-pyrazol-3-yl)-ethanol

To a stirring solution of 150 mg (0.96 mmol) of methyl 3,5-dioxohexanoate in 5 mL of MeOH at RT was added 104 mg (0.96 mmol) of phenylhydrazine followed by 10 mg of p-toluenesulfonic acid. The reaction mixture was stirred 15 min at RT then refluxed for 2 h. The reaction was cooled to RT, diluted with 10 mL of EtOAc, and washed with NaHCO$_3$ (1×10 mL). The organic layer was separated, dried (MgSO$_4$), and the solvents removed in vacuo. Purification of the material by silica gel flash column chromatography using hexane/EtOAc 3/1 as eluent to afford 180 mg of the cyclized methyl ester. This material was then reduced according to the procedure outlined for the preparation of Intermediate 43: $^1$H NMR (CDCl$_3$, 400 MHz) δ 7.41 (m, 5H), 6.10 (s, 1H), 3.81 (t, 2H, J=6.5), 2.89 (t, 2H, J=6.5), 2.32 (s, 3H).

Intermediate 49

2(S)-(2-benzoyl-phenylamino)-3-{4-[2-(5-methyl-1-phenyl-1H-pyrazol-3-yl)-ethoxy]-phenyl}-propionic acid methyl ester The title compound (100 mg) was prepared from 275 mg (0.74 mmol) of Intermediate 23 and 150 mg (0.74 mmol) of Intermediate 48 according to the method of Intermediate 44 followed by purification via silica gel flash column chromatography using a gradient elution of hexane/EtOAc 4/1 to hexane/EtOAc 2/1 as eluent: low resolution MS (FAB)m/e 561 (MH$^+$), 560 (M$^+$).

Intermediate 50

[2-(2-piperadin-1-yl)-5-methyl-oxazol-4-yl]-acetic acid methyl ester

A mixture of 1.72 g (13.40 mmol, 4.0 equiv) of 1-piperidine carboxamide and 700 mg (3.35 mmol) of methyl 4-bromo-3-oxo-pentanoate in 3 mL of dry DMF was heated at 120° C. for 15 h. The resulting dark slurry was cooled to RT, diluted with 10 mL of EtOAc, and washed with H$_2$O (1×10 mL). The organic layer was separated, dried (MgSO$_4$), and the solvents removed in vacuo. Purification of the material by silica gel flash column chromatography using hexane/EtOAc 2/1 as eluent to afford 192 mg of the title compound as an orange oil: low resolution MS (FAB) m/e 240 (MH$^+$), 239 (M$^+$).

Intermediate 51

2-[5-methyl-2-piperidin 1-yl-oxazol-4-yl]-ethanol

The title compound (145 mg) was prepared from 190 mg (0.80 mmol) of Intermediate 50 according to the method of Intermediate 43: $^1$H NMR (CDCl$_3$, 400 MHz) δ 5.03 (t, 1H, J=5.8), 3.90 (d, 2H, J=5.9), 3.73 (m, 4H), 2.83 (t, 2H, J=5.9), 2.19 (s, 3H), 1.71 (m, 6H).

Intermediate 52

2(S)-(2-benzoyl-phenylamino)-3-{4-[2-(5-methyl-2-piperidin-1-yl-oxazol-4-yl)-ethoxy]-phenyl}-propionic acid methyl ester The title compound (280 mg) was prepared from 250 mg (0.67 mmol) of Intermediate 23 and 140 mg (0.67 mmol) of Intermediate 51 according to the method of Intermediate 44 followed by purification via silica gel flash column chromatography using hexane/EtOAc 2/1 as eluent: low resolution MS (FAB)m/e 568 (MH$^+$), 567 (M$^+$).

Intermediate 53

1-Morpholine thiocarboxamide

To a stirring solution of 2.0 g (11.20 mmol, 1.15 equiv) of thiocarbonyldiimidazole in 30 mL of THF at RT was added 932 mg (10.70 mmol) of morpholine. The reaction mixture was stirred at RT for 2 h then heated to 55° C. for 1 h. The reaction mixture was cooled to RT and approximately 20 mL of THF was removed in vacuo, and then 10 mL of a 2.0 M solution of ammonia in MeOH was added and the reaction mixture was sealed and stirred 15 h. An additional 10 mL of 2.0 M ammonia in MeOH was then added and the reaction stirred in a warm water bath for 8 h, during which time a white precipitate appeared. The precipitate was filtered, rinsed with diethyl ether, collected and dried to provide 745 mg of the title compound: low resolution MS (FAB)m/e 147 (MH$^+$).

Intermediate 54

2-(2-morpholin-4-yl-5-methyl-thiazol-4-yl)-acetic acid methyl ester

A mixture of 375 mg (2.56 mmol) of Intermediate 53 and 536 mg (2.56 mmol) of methyl 4-bromo-3-oxo-pentanoate in 5 mL of absolute ethanol was refluxed for 5 h. The reaction was cooled to RT, and the ethanol removed in vacuo. The residue was diluted with 10 mL of EtOAc, and washed with NaHCO$_3$ (1×10 mL). The organic layer was separated, dried (MgSO$_4$), and the solvents removed in vacuo. Purification of the material by silica gel flash column chromatography using hexane/EtOAc 2/1 as eluent to afford 590 mg of the title compound as a clear oil: $^1$H NMR (CDCl$_3$, 400 MHz) δ 3.79 (m, 4H), 3.69 (s, 3H), 3.47 (s, 2H), 3.38 (m, 4H), 2.23 (s, 3H).

Intermediate 55

2-[5-methyl-2-morpholin-1-yl-oxazol-4-yl]-ethanol

The title compound (487 mg) was prepared from 590 mg (2.27 mmol) of Intermediate 54 according to the method of Intermediate 43: $^1$H NMR (CDCl$_3$, 400 MHz) δ 4.29 (t, 1H, J=5.9), 3.90 (d, 2H, J=5.9), 3.82 (m, 6H), 3.37 (m, 4H), 2.68 (t, 2H, J=5.4), 2.22 (s, 3H).

Intermediate 56

2(S)-(2-benzoyl-phenylamino)-3-{4-[2-(5-methyl-2-morpholin 4-yl-thiazol-4-yl)-ethoxy]-phenyl}-propionic acid methyl ester The title compound (810 mg) was prepared from 760 mg (2.02 mmol) of Intermediate 23 and 480 mg (2.02 mmol) of Intermediate 55 according to the method of Intermediate 44 followed by purification via silica gel flash column chromatography using hexane/EtOAc 2/1 as eluent: $^1$H NMR (CDCl$_3$, 400 MHz) δ 8.89 (d, 1H, J=7.3), 7.59 (d, 2H, J=8.6) 7.47 (m, 3H), 7.33 (dd, 1H, J=7.2, 7.2), 7.17 (d, 2H, J=8.6), 6.82 (d, 2H, J=8.6), 6.63 (d, 1H, J=8.5), 6.57 (dd, 1H, J=7.5, 7.5), 4.37 (dd, 1H, J=7.2, 13.3), 4.15 (t, 2H, J=7.1), 3.78 (m, 4H), 3.69 (s, 3H), 3.36 (m, 4H), 3.19 (dd, 1H, J=6.0, 13.9), 3.11 (dd, 1H, J=7.3, 13.9), 2.93 (t, 2H, J=7.1), 2.23 (s, 3H).

Intermediate 57

[2-(2-pyrindin-4-yl)-5-methyl-thiazol-4-yl]-acetic acid methyl ester

A mixture of 800 mg (5.79 mmol) of thioisonicotinamide and 1.21 g (5.79 mmol) of methyl 4-bromo-3-oxo-pentanoate in 20 mL of toluene/absolute ethanol 1:1 was heated to 100° C. for 18 h. The reaction was cooled to RT, diluted with 20 mL of EtOAc, and washed with NaHCO$_3$ (1×10 mL). The organic layer was separated, dried (MgSO$_4$), and the solvents removed in vacuo. Purification of the material by silica gel flash column chromatography using hexane/EtOAc 1/1 as eluent afforded 630 mg of the title compound as an orange solid: $^1$H NMR (CDCl$_3$, 400 MHz) δ 8.64 (d, 2H, J=6.1), 7.70 (d, 2H, J=6.1), 3.82 (s, 2H), 3.71 (s, 3H), 2.45 (s, 3H).

Intermediate 58

2-[5-methyl-2-(4-pyridyl)-thiazol-4-yl]ethanol

The title compound was prepared from 620 mg (2.50 mmol) of Intermediate 57 according to the method of Intermediate 43 followed by purification via silica gel flash column chromatography using a gradient of EtOAc to EtOAc/MeOH 30/1 as eluent: $^1$H NMR (CDCl$_3$, 400 MHz) δ 8.66 (d, 2H, J=6.1), 7.71 (d, 2H, J=6.1), 4.01 (m, 2H), 3.57 (t, 1H, J=6.0), 2.93 (t, 2H, J=5.8), 2.46 (s, 3H).

Intermediate 59

2(S)-(2-benzoyl-phenylamino)-3-{4-[2-(5-methyl-2-(4-pyridyl)-thiazol-4-yl)-ethoxy]-phenyl}-propionic acid methyl ester The title compound was prepared from 255 mg (0.68 mmol) of Intermediate 23 and 150 mg (0.68 mmol) of Intermediate 58 according to the method of Intermediate 44 followed by purification via silica gel flash column chromatography using hexane/EtOAc 3/2 as eluent: Anal. (C$_{34}$H$_{31}$N$_3$O$_4$S) Calcd. C, 70.69; H, 5.41; N, 7.27, Found C, 70.44; H, 5.50; N, 7.03.

Intermediate 60

[2-(2-dimethylamino)-5-methyl-thiazol-4-yl]-acetic acid methyl ester

A mixture of 750 mg (7.20 mmol, 1.5 equiv) of N,N-dimethylthiourea and 1.00 g (4.80 mmol) of methyl 4-bromo-3-oxo-pentanoate in 10 mL of dioxane was heated to reflux for 3 h. The reaction was cooled to RT, diluted with 20 mL of EtOAc, and washed with NaHCO$_3$ (1×10 mL). The organic layer was separated, dried (MgSO$_4$), and the solvents removed in vacuo. Purification of the material by silica gel flash column chromatography using a gradient of hexane/EtOAc 1/5 to EtOAc/MeOH 20/1 as eluent afforded 210 mg of the title compound as an yellow oil: low resolution MS (FAB)m/e 216 (MH$^+$), 215 (M$^+$).

Intermediate 61

2-[2-dimethylamino-5-methyl-oxazol-4-yl]-ethanol

The title compound was prepared from 210 mg (0.98 mmol) of Intermediate 60 according to the method of Intermediate 43: low resolution MS (FAB)m/e 188 (MH$^+$), 187 (M$^+$).

Intermediate 62

2(S)-(2-benzoyl-phenylamino)-3-{4-[2-(2-dimethylamino-5-methyl--thiazol-4-yl)-ethoxy]-phenyl}-propionic acid methyl ester The title compound (168 mg) was prepared from 390 mg (1.00 mmol) of Intermediate 23 and 185 mg (1.00 mmol) of Intermediate 61 according to the method of Intermediate 44 followed by purification via silica gel flash column chromatography initially using hexane/EtOAc 2/1 as eluent to remove nonpolar impurities then using chloroform/MeOH to elute the desired product: low resolution MS (FAB)m/e 544 (M$^+$).

Intermediate 63

5-Methylisoxazole-3-thiocarboxamide

A suspension of 525 mg (4.16 mmol) of 5-methylisoxazole-3-carboxamide and 1.85 g (4.58 mmol, 1.1 equiv) of Lawesson's reagent in 15 mL of dry toluene was heated to reflux for 5 h, during which time the reaction mixture became a clear yellow color. The reaction mixture was cooled to RT and the solvent was removed in vacuo. Purification of the material by silica gel flash column chromatography using a gradient of hexane/EtOAc 5/1 to hexane/EtOAc 1/1 as eluent followed by trituration with acetonitrile, filtration to remove the solid Lawesson's reagent byproducts and removal of solvent afforded 614 mg of the title compound as a yellow oil: $^1$H NMR (CDCl$_3$, 300 MHz) δ 8.05 (s, br, 2H), 6.52 (s, 1H), 2.46 (s, 3H).

Intermediate 64

2-[5-methyl-2-(5-methyl-isoxazol-3-yl)-oxazol-4-yl]-acetic acid methyl ester

The title compound (375 mg) was prepared from 591 mg (4.15 mmol) of Intermediate 63 and 950 mg (4.47 mmol, 1.10 equiv) of methyl 4-bromo-3-oxo-pentanoate according to the method of Intermediate 45 followed by purification via silica gel flash column chromatography using hexane/EtOAc 5/1 as eluent: low resolution MS (FAB)m/e 216 (MH$^+$), 215 (M$^+$).

Intermediate 65

2-[5-methyl-2-(5-methyl-isoxazol-3-yl)-oxazol-4-yl]-ethanol

The title compound (187 mg) was prepared from 375 mg (1.49 mmol) of Intermediate 64 according to the method of Intermediate 43: $^1$H NMR (CDCl$_3$, 400 MHz) δ 6.50 (s, 1H), 3.97 (m, 2H), 3.46 (t, 1H, J=6.2), 2.92 (t, 2H, J=5.6), 2.49 (s, 3H), 2.44 (s, 3H).

Intermediate 66

2(S)-(2-benzoyl-phenylamino)-3-{4-[2-(5-methyl-2-(5-methyl-isoxazol-3-yl)-thiazol-4-yl)-ethoxy]-phenyl}-propionic acid methyl ester The title compound (470 mg) was prepared from 530 mg (1.45 mmol) of Intermediate 23 and 317 mg (1.45 mmol) of Intermediate 65 according to the method of Intermediate 44 followed by purification via silica gel flash column chromatography using a gradient of hexane/EtOAc 4/1 to hexane/EtOAc 2/1 as eluent: low resolution MS (FAB)m/e 582 (MH$^+$).

Intermediate 67

[5-methyl-2-(4-methyl[1,2,3]thiadiazol-5-yl)-oxazol-4-yl]-acetic acid methyl ester The title compound (560 mg) was prepared from 1.0 g (7.00 mmol) of 4-methyl-1,2,3-thiadiazole-5-carboxamide and 2.97 g (7.35 mmol, 1.05 equiv) of Lawesson's reagent according to the method of Intermediate 63, followed by the procedure outlined for the preparation of Intermediate 45 and purification via silica gel flash column chromatography using hexane/EtOAc 4/1 as eluent: low resolution MS (FAB)m/e 270 (M$^+$).

Intermediate 68

2-[5-methyl-2-(4-methyl[1,2,3]thiadiazol-5-yl)-oxazol-4-yl]-ethanol

The title compound (350 mg) was prepared from 560 mg (2.08 mmol) of Intermediate 67 according to the method of Intermediate 43 followed by purification via silica gel flash column chromatography using chloroform/MeOH 9/1 as eluent: $^1$H NMR (CDCl$_3$, 400 MHz) δ 3.99 (m, 2H), 3.02 (s, br, 1H), 2.94 (m, 5H), 2.49 (s, 3H).

Intermediate 69

2(S)-(2-benzoyl-phenylamino)-3-(4-{2-[5-methyl-2-(4-methyl[1,2,3]thiadiazol-5-yl)-thiazol-4-yl]-ethoxy}-phenyl)-propionic acid The title compound (235 mg) was prepared from 560 mg (1.49 mmol) of Intermediate 23 and 360 mg (1.49 mmol) of Intermediate 68 according to the method of Intermediate 44 followed by purification via silica gel flash column chromatography using a gradient of hexane/EtOAc 4/1 to hexane/EtOAc 3/1 as eluent: $^1$H NMR (CDCl$_3$, 400 MHz) δ 8.88 (d, 1H, J=7.3), 7.59 (dd, 2H, J=1.6, 8.4) 7.48 (m, 3H), 7.33 (dd, 1H, J=7.3, 7.3), 7.17 (d, 2H, J=8.5), 6.80 (d, 2H, J=8.5), 6.62 (d, 1H, J=8.6), 6.58 (dd, 1H, J=7.6, 7.6), 4.38 (m, 1H), 4.25 (t, 2H, J=6.5), 3.69 (s, 3H), 3.16 (m, 4H), 2.92 (s, 3H), 2.50 (s, 3H).

Intermediate 70

[5-methyl-2-(4-methyl-piperazin-1-yl)-thiazol-4-yl]-acetic acid methyl ester

The title compound (490 mg) was prepared from 18.7 g (104.8 mmol) of thiocarbonyldiimidazole and 10 g (99.8 mmol) of 1-methyl piperazine according to the method of intermediate 53, followed by the procedure outlined for the preparation of Intermediate 60 and purification via silica gel chromatography using MeOH/EtOAc (3:17) as eluent: TLC (MeOH/EtOAc (1:9)): R$_f$=0.15.

Intermediate 71

2-[5-methyl-2-(4-methyl-piperazin-1-yl)-thiazol-4-yl]-ethanol

The title compound (2.20 g) was prepared from 2.87 g (8.10 mmol) of Intermediate 70 according to the method of Intermediate 43 followed by purification via silica gel flash column chromatography using chloroform/MeOH 10/1 as eluent: $^1$H NMR (CDCl$_3$, 400 MHz) δ 4.42 (s, br, 1H), 3.85 (m, 2H), 3.41 (m, 4H), 2.67 (t, 2H, J=5.4), 2.49 (m, 4H), 2.34 (s, 3H), 2.20 (s, 3H).

Intermediate 72

[2-(3-dimethylamino-propylamino)-5-methyl-thiazol-4-yl]-acetic acid methyl ester The title compound (854 mg) was prepared from 1.0 g (6.20 mmol) of 3-dimethylaminopropyl thiourea and 1.30 g (6.20 mmol) of methyl 4-bromo-3-oxo-pentanoate according to the method of Intermediate 45: low resolution MS (FAB)m/e 272 (M$^+$).

Intermediate 73

2-[2-(3-dimethylamino-propylamino)-5-methyl-thiazol-4-yl]-ethanol

The title compound (608 mg) was prepared from 850 mg (3.14 mmol) of Intermediate 72 according to the method of Intermediate 43: $^1$H NMR (CDCl$_3$, 400 MHz) d 6.18 (s, br, 1H), 4.40 (s, br, 1H), 3.83 (t, 2H, J=5.5), 3.28 (m, 2H), 2.65 (t, 2H, J=5.5), 2.39 (t, 2H, J=6.4), 2.23 (s, 6H), 2.18 (s, 3H), 1.76 (m, 2H).

Intermediate 74

2(S)-(2-benzoyl-phenylamino)-3-(4-{2-[2-(3-dimethylamino-propylamino)-5-methyl-thiazol-4-yl]-ethoxy}-phenyl)-propionic acid methyl ester A suspension of 715 mg (2.73 mmol, 1.10 equiv) of triphenylphosphine, 929 mg (2.48 mmol) of Intermediate 23, and 600 mg (2.48 mmol) of Intermediate 73 in 25 mL of dry toluene was heated to 95° C. for 15 min to effect dissolution of Intermediate 23 to provide a clear yellow solution. To this solution was added 452 mg (2.60 mmol, 1.05 equiv) of diethyl azodicarboxylate dropwise over 5 min. The reaction was then allowed to cool to RT and stirred 16 h. The toluene was removed in vacuo, and the residue was purified by silica gel flash column chromatography using

Intermediate 75

2-[2-(2-methoxy-ethylamino)-5-methyl-thiazol-4-yl] ethanol

The title compound (800 mg) was prepared from 750 mg (5.59 mmol) of 2-methoxyethyl thiourea and 1.17 g (5.59 mmol) of methyl 4-bromo-3-oxo-pentanoate according to the method of Intermediate 60, followed by the procedure outlined for the preparation of Intermediate 43 nd purification via silica gel flash column chromatography using chloroform/MeOH 9/1 as eluent: $^1$H NMR (CDCl$_3$, 400 MHz) δ 3.82 (t, 2H, J=5.5), 3.58 (t, 2H, J=6.9), 3.41 (m, 2H), 3.36 (s, 3H), 2.65 (t, 2H, J=6.9), 2.19 (s, 3H).

Intermediate 76

2(S)-(2-benzoyl-phenylam ino)-3-(4-{2-[2-(2-methoxy-ethylamino)-5-methyl-thiazol-4-yl]-ethoxy}-phenyl)-propionic acid methyl ester The title compound (907 mg) was prepared from 1.38 g (3.70 mmol) of Intermediate 23, and 800 mg (3.70 mmol) of Intermediate 75 according to the method of Intermediate 74 followed by purification via MPLC (Merck Lobar Si60 column, diethyl ether/dichloromethane 1/4 as eluent): low resolution MS (FAB)m/e 574 (M$^+$).

Intermediate 77

3-{4-[2-(Benzoxazol-2-yl-methyl-amino)-ethoxy]-phenyl}-2-(2-cyclopentanecarbonyl-phenylamino)-propionic acid methyl ester The title compound (580 mg) was prepared from 650 mg (1.71 mmol) of Intermediate 9, 646 mg (3.42 mmol, 2.0 equiv.) of (2-amino-phenyl)-cyclopentyl-methanone and 15 mg (0.003 mmol, 0.01 equiv.) of rhodium acetate according to the method of Intermediate 3 followed by purification via silica gel flash column chromatography using hexane/EtOAc 7/3 as eluent: low resolution MS (ES) m/e 542.1 (MH$^+$).

Intermediate 78

3-{4-[2-(Benzoxazol-2-yl-methyl-amino)-ethoxy]-phenyl}-2-(2-cycloheptanecarbonyl-phenylamino)-propionic acid methyl ester The title compound (130 mg) was prepared from 650 mg (1.71 mmol) of Intermediate 9, 742 mg (3.42 mmol, 2.0 equiv.) of (2-amino-phenyl)-cycloheptyl-methanone and 15 mg of rhodium acetate according to the method of Intermediate 3 followed by purification via silica gel flash column chromatography using hexane/EtOAc 7/3 as eluent: low resolution MS (ES) m/e 569.9 (MH$^+$).

Intermediate 79

3-{4-[2-(Benzoxazol-2-yl-methyl-amino)-ethoxy]-phenyl}-2-(2-cyclohexanecarbonyl-5-fluoro-phenylamino)-propionic acid methyl ester The title compound (392 mg) was prepared from 400 mg (1.71 mmol) of Intermediate 9, 325 mg (1.47 mmol, 1.4 equiv.) of (2-amino-4-fluoro-phenyl)-cycloheptyl-methanone and 10 mg of rhodium acetate according to the method of Intermediate 3 followed by purification via silica gel flash column chromatography using hexane/EtOAc 7/3 as eluent: low resolution MS (ES) m/e 574.0 (MH$^+$).

Intermediate 80

3-{4-[2-(Benzoxazol-2-yl-methyl-amino)-ethoxy]-phenyl}-2-(4-cyclohexane carbonyl-2-methyl-2H-pyrazol-3-ylamino)-propionic acid methyl ester The title compound (278 mg) was prepared from 400 mg (1.05 mmol) of Intermediate 9, 287 mg (1.47 mmol, 1.4 equiv.) of (5-amino-1-methyl-1H-pyrazol-4-yl-cyclohexyl-methanone and 10 mg of rhodium acetate according to the method of Intermediate 3 followed by purification via silica gel flash column chromatography using hexane/EtOAc 7/3 as eluent: low resolution MS (ES) m/e 560.2 (MH$^+$).

Intermediate 81

3-{4-[2-(Benzoxazol-2-yl-methyl-amino)-ethoxy]-phenyl}-2-(3-benzoyl-thiophene-2-ylamino)-propionic acid methyl ester The title compound (145 mg) was prepared from 137 mg (0.36 mmol) of Intermediate 9 , 104 mg (0.51 mmol, 1.4 equiv.) of (2-amino-thiophen-3-yl)-phenyl-methanone and 5 mg of rhodium acetate according to the method of Intermediate 3 followed by purification via silica gel flash column chromatography using hexane/EtOAc 7/3 as eluent: low resolution MS (ES) m/e 556.0 (MH$^+$).

Intermediate 83

2-(2-Cyclohexanecarbonyl-phenylamino)-3-{4-[2-(5-methyl-2-phenyl-oxazol-4-yl)-ethoxy]-phenyl}-propionic acid methyl ester The title compound (2.89 g) was prepared from 3.03 g (7.75 mmol) of Intermediate 121, 2.07 g (10.51 mmol, 1.4 equiv.) of (2-amino-phenyl)-cyclohexyl-methanone and 69 mg of rhodium acetate according to the method of Intermediate 3 followed by purification via silica gel flash column chromatography using DCM to 1/99 diethyl ether/DCM as eluent: low resolution MS (ES) m/e 567.4 (MH$^+$); The enantiomers of this material were then separated on a Prep OD Column ; Enantiomer 1: NMR, MS, HPLC identical to racemate. Enantiomer 2: NMR, MS,HPLC identical to racemate.

Intermediate 84

(S)(−)-1-benzyl-pyrrolidin-3-yl methanesulfonate

To (S)(−)-1-benzyl-3-pyrrolidinol (5 g, 28.2 mmol) in pyridine (40 mL) was added methane sulphonyl chloride (2.03 mL, 26.2 mmol, 0.93 equiv.) dropwise. The reaction mixture stirred 3 h, was poured into ice water (100 mL) and extracted with DCM (3×50 mL). The combined organic extracts were washed with saturated aq NaHCO$_3$, brine and dried (MgSO$_4$) to give 3 g of the titled compound: low resolution MS (ES) m/e 256.0 (MH$^+$).

Intermediate 85

2-(2-Benzolyl-phenylamino)-3-[4-(1-benzyl-pyrrolidin-3-yloxy)-phenyl]-propionic acid methyl ester To a stirring solution of 1.0 g (2.66 mmol) of Intermediate 23 in 30 mL of DMF was added 0.95 g (2.95 mmol, 1.1 equiv.) of cesium carbonate and 747 mg. (2.93 mmol, 1.1 equiv.) of Intermediate 84. The resulting solution was stirred 24 h at 45° C. then quenched into 10 mL water. The reaction mixture was poured into 25 mL of EtOAc and 25 mL of Et$_2$O and extracted with H$_2$O (3×10 mL). The organic layer was dried (MgSO$_4$), and the solvents removed in vacuo. Purification by silica gel flash column chromatography using hexane/EtOAc 7/3 as eluent afforded 0.68 g of the title compound: low resolution MS (API) m/e 535.1 (MH$^+$).

Intermediate 86

3-[4-(1-Benzoxazol-2-yl-pyrrolidin-3-yloxy)-phenyl]-2-(2-benzoyl-phenylamino)-propionic acid methyl ester To 0.60 g of Intermediate 85 (1.12 mmol) in DCM (30 mL) at 0° C. was added alpha-chloroethyl chloroformate (0.24 mL, 2.24 mmol, 2 equiv). The reaction mixture stirred at 0° C. for 30 min and then was concentrated to dryness. The resulting residue was dissolved in MeOH (100 mL), refluxed for 2.5 h, then concentrated to dryness. To this crude material (0.71 g, 1.12 mmol) was added triethylamine (0.47 mL, 3.36 mmol, 3 equiv). The reaction mixture stirred 5 min followed by dropwise addition of 2-chlorobenzoxazole in THF (2 mL). The reaction mixture stirred 12 h at RT, was concentrated in vacuo. Purification by silica gel flash column chromatography using ET$_2$O/DCM 10/90 as eluent afforded 200 mg of the titled product: low resolution MS (ES) m/e 562.1 (MH$^+$).

Intermediate 87

3-{4-[2-(5-Methyl-2-phenyl-oxazol-4-yl)-ethoxy]-phenyl}-2-(S)-[2-(pyridine4-carbonyl)-phenylamino]-propionic acid methyl ester The title compound (2.92 g) was prepared from Intermediate 120 (3.65 g, 9.61 mmol) and 2-(pyridine-4-carbonyl)-cyclohexanone (2.92 g, 9.61 mmol) according to the method of Intermediate 23 followed by purification via silica gel flash column chromatography using DCM/MeOH 98/2 as eluent: low resolution MS (ES) m/e 546.0 (MH$^+$).

Intermediate 88

3-{4-[2-(5-methyl-2-phenyl-oxazol-4-yl)-ethoxy]-phenyl}-2-[2-(pyridineN-oxide4-carbonyl)-phenylamino]-propionic acid methyl ester To Intermediate 87 (200 mg, 0.36 mmol) in DCM (5 mL) at RT was added mCPBA (185 mg, 1.07 mmol, 3 equiv). After 24 h the reaction mixture was concentrated in vacuo. Purification by silica gel flash column chromatography using DCM/MeOH 98/2 to 90/10 as eluent afforded 90 mg of the title compound: low resolution MS (ES) m/e 578.1 (MH$^+$).

Intermediate 89

3-{4-[2-(5-Methyl-2-phenyl-oxazol-4-yl)-ethoxy]-phenyl}-2(S)-[2-(pyridine-3-carbonyl)-phenylamino]-propionic acid methyl ester The title compound (540 mg) was prepared from Intermediate 120 (1.30 g, 2.63 mmol) and 2-(pyridine-3-carbonyl)-cyclohexanone (1.07 g, 5.26 mmol) according to the method of Intermediate 23 followed by purification via silica gel flash column chromatography using hexane to 1/1 hexane/EtOAc as eluent: low resolution MS (ES) m/e 562.2 (MH$^+$).

Intermediate 90

2-(5-methyl-3-phenyl-pyrazol-1-yl)-ethanol

A solution of 497 mg (3.14 mmol) of 3-methyl-5-phenylpyrazole in 12.6 mL of DMF at 0° C. was treated with 138 mg (3.45 mmol, 60% in oil) of NaH. After stirring for 15 min, 1.38 g (15.7 mmol) of ethylene carbonate was added, and the reaction was warmed to 25° C. and stirred overnight. The reaction was diluted with H$_2$O and the product was extracted with hexanes/EtOAc (1:1). The combined organics were dried (MgSO$_4$), filtered, and concentrated in vacuo. The residue was purified by silica gel flash column chromatography using hexanes/EtOAc (1:3) as eluent to give 305 mg (48%) of title compound: low resolution MS (ES) m/e 225 (MNa$^+$), 203 (MH$^+$).

Intermediate 91

2S-(2-benzoyl-phenylamino)-3-{4-[2-(5-methyl-3-phenyl-pyrazol-1-yl)-ethoxy]-phenyl}-propionic acid methyl ester A solution of 169 mg (0.45 mmol) of Intermediate 23, 100 mg (0.49 mmol) of Intermediate 90, and 177 mg (0.67 mmol) of triphenylphosphine in 4.5 mL of THF at 25° C. was treated dropwise with 0.106 mL (0.67 mmol) of DEAD. The reaction was stirred at 25° C. for 24 h then concentrated in vacuo. The residue was purified by silica gel flash column chromatography using hexanes/EtOAc (2:1) as eluent to give 116 mg (46%) of title compound as a viscous yellow oil: low resolution MS (ES) m/e 582 (MNa$^+$), 560 (MH$^+$).

Intermediate 92

2S-(2-benzoyl-phenylamino)-3-[4-(1-tert-butoxycarbonyl-pyrrolidin-2S-yl-methoxy)-phenyl]-propionic acid methyl ester The title compound (1.62 g) was prepared from 2.82 g (7.5 mmol) of Intermediate 23 and 1.66 g (8.25 mmol) of N-tert-butoxycarbonyl-L-prolinol according to the method of Intermediate 91 followed by purification via silica gel flash column chromatography eluting with hexanes/EtOAc (3:1) as eluent: low resolution MS (ES) m/e 581 (MNa$^+$), 559 (MH$^+$).

Intermediate 93

2S-(2-benzoyl-phenylamino)-3-[4-(1-pyridin-2-yl-pyrrolidin-2S-yl-methoxy)-phenyl]-propionic acid methyl ester A solution of 2.95 g (5.3 mmol) of Intermediate 92 in 62 mL of CH$_2$Cl$_2$ was treated with 62 mL of trifluoroacetic acid and stirred 1 h. The reaction was diluted with CH$_2$Cl$_2$ and basified with saturated Na$_2$CO$_3$. The aqueous layer was extracted with CH$_2$Cl$_2$, and the combined organic layers were dried (Na$_2$SO$_4$), filtered, and concentrated in vacuo. The residue was dissolved in 210 mL of 2-fluoropyridine and heated at reflux for 24 h. Upon cooling to 25° C. the reaction was concentrated in vacuo, and the residue was purified by silica gel flash column chromatography eluting with hexanes/EtOAc (2:1) to give 1.2 g (42%) of the title compound as a viscous yellow oil: low resolution MS (ES) m/e 558 (MNa$^+$), 536 (MH$^+$).

Intermediate 94

2-(1-methyl-4-phenyl-1H-imidazol-2-yl)-ethanol

A solution of 674 mg (4.26 mmol) of 1-methyl-4-phenylimidazole (Kashima, C.; Harada, Y.; Hosomi, A.

*Heterocycles* 1993, 35, 433) in 8.5 mL of THF at −78° C. was treated with 1.9 mL (4.69 mmol) of a 2.5 M nBuLi in hexanes solution. After stirring for 10 min, 1.1 mL (21.3 mmol) of ethylene oxide was added. The reaction was stirred for min then warmed to 25° C. and stirred for 1 h. Upon cooling to 0° C., 1.1 mL (21.3 mmol) of ethylene oxide was added, and the reaction was warmed to 25° C. and stirred overnight. The reaction was poured into $H_2O$ and extracted with $Et_2O$. The combined organics were dried ($Na_2SO_4$), filtered, and concentrated in vacuo. The residue was purified by silica gel flash column chromatography using EtOAc/MeOH (95:5), and the collected product was recrystallized from $CH_2Cl_2$/EtOAc to give 178 mg (21%) of title compound as a white solid: low resolution MS (ES) m/e 225 ($MNa^+$), 203 ($MH^+$).

Intermediate 95

2S-(2-benzoyl-phenylamino)-3-{4-[2-(1-methyl-4-phenyl-1H-imidazol-2-yl)-ethoxy]-phenyl}-propionic acid methyl ester The title compound (90 mg) was prepared from 93 mg (0.25 mmol) of Intermediate 23 and 50 mg (0.25 mmol) of Intermediate 94 according to the method of Intermediate 91 followed by purification via silica gel flash column chromatography using hexanes/EtOAc (1:3) as eluent: low resolution MS (ES) m/e 582 ($MNa^+$), 560 ($MH^+$).

Intermediate 96

3-furan-2-yl-5-methylpyrazole

To a solution of 1.07 g (7.03 mmol) of 1-(2-furyl)-1,3-butanedione in 26 mL of MeOH at 25° C. was added 0.442 mL (14.07 mmol) of hydrazine. The reaction was stirred for 24 h then concentrated in vacuo. The residue was purified by silica gel flash column chromatography using hexanes/EtOAc (1:1) as eluent to give 1.02 g (98%) of title compound: low resolution MS (CI) m/e 149 ($MH^+$).

Intermediate 97

2-(3-furan-2-yl-5-methyl-pyrazol-1-yl)-ethanol

The title compound (189 mg) was prepared from 1.01 g (6.82 mmol) of Intermediate 96 according to the method of Intermediate 90 followed by purification via silica gel flash column chromatography using hexanes/EtOAc (1:3) as eluent: low resolution MS (CI) m/e 215 ($MNa^+$), 193 ($MH^+$).

Intermediate 98

2-(5-methyl-3-phenyl-[1,2,4]triazol-1-yl)-ethanol

The title compound (140 mg) was prepared from 550 mg (3.45 mmol) of 3-phenyl-5-methyl-[1,2,4]triazole (Francis, J. E.; Gorczyca, L. A.; Mazzenga, G. C.; Meckler, H. *Tetrahedron Lett.* 1987, 28, 5133) according to the method of Intermediate 90 followed by purification via silica gel flash column chromatography using EtOAc/MeOH (95:5) as eluent and recrystallization from $Et_2O$: low resolution MS (CI) m/e 204 ($MH^+$).

Intermediate 99

2S-(2-benzoyl-phenylamino)-3-{4-[2-(5-methyl-3-phenyl-[1,2,4]triazol-1-yl)-ethoxy]-phenyl}-propionic acid methyl ester The title compound (186 mg) was prepared from 196 mg (0.52 mmol) of Intermediate 23 and 106 mg (0.52 mmol) of Intermediate 98 according to the method of Intermediate 44 followed by purification via silica gel flash column chromatography using hexanes/EtOAc (1:1Æ 1:2) as eluent: low resolution MS (ES) m/e 583 ($MNa^+$), 561 ($MH^+$).

Intermediate 100

3-methoxymethyl-5-methyl-2-phenyl-3H-imidazole

To a solution of 1.0 g (6.32 mmol) of 4-methyl-2-phenylimidazole in 25 mL of DMF at 0° C. was added 278 mg (6.95 mmol, 60% in oil) of NaH. After stirring for 5 min, 0.528 mL (6.95 mmol) of chloromethyl methyl ether was added, and the reaction was warmed to 25° C. and stirred 4 h. The reaction was poured into $H_2O$, and the product was extracted with hexanes/EtOAc (1:1). The combined organic layers were dried ($Na_2SO_4$), filtered, and concentrated in vacuo. Purification by silica gel flash column chromatography using hexanes/EtOAc (5:95) as eluent provided 816 mg (64%) of title compound: low resolution MS (ES) m/e 225 ($MNa^+$), 203 ($MH^+$).

Intermediate 101

2-(3-methoxymethyl-5-methyl-2-phenyl-3H-imidazol-4-yl)-ethanol

The title compound (433 mg) was prepared from 710 mg (3.51 mmol) of Intermediate 100 according to the method of Intermediate 94 followed by purification via silica gel flash column chromatography using EtOAc/MeOH (93:7) as eluent: low resolution MS (ES) m/e 269 ($MNa^+$), 247 ($MH^+$).

Intermediate 102

2S-(2-benzoyl-phenylamino)-3-{4-[2-(3-methoxymethyl-5-methyl-2-phenyl-3H-imidazol-4-yl)-ethoxy]-phenyl}-propionic acid methyl ester The title compound (347 mg) was prepared from 314 mg (0.84 mmol) of Intermediate 23 and 207 mg (0.84 mmol) of Intermediate 101 according to the method of Intermediate 44 followed by purification via silica gel flash column chromatography using EtOAc/hexanes (3:1) as eluent to give 347 mg (69%) of title compound: low resolution MS (ES) m/e 604 ($MNa^+$), 626 ($MH^+$).

Intermediate 103

2-(3-trimethylsilyiethoxymethyl-5-methyl-2-phenyl-3H-imidazol-4-yl)-ethanol

A solution of 1.04 g (6.57 mmol) of 2-phenyl-3-methylimidazole in 25 mL of DMF at 0° C. was treated with 289 mg (7.23 mmol, 60% in oil) of NaH. After stirring for 5 min, 1.28 mL (7.23 mmol) of 2-(trimethylsilyl)ethoxymethyl chloride was added. The reaction was stirred for 10 min then warmed to 25° C. and stirred overnight. The reaction was poured into $H_2O$, and the product was extracted with hexanes/EtOAc (1:1). The combined organic layers were dried ($Na_2SO_4$), filtered, and concentrated in vacuo. The residue was purified by silica gel flash column chromatography using EtOAc/MeOH (98:2) as eluent to give 1.18 g (62%) of protected intermediate. This material was then converted to the title compound (851 mg) according to the method of Intermediate 94 followed by purification via silica gel flash column chromatography using EtOAc/MeOH (95:5Æ 9:1) as eluent: low resolution MS (ES) m/e 233 ($MH^+$).

Intermediate 104

2S-(2-benzoyl-phenylamino)-3-{4-[2-(5-methyl-2-phenyl-3H-imidazol-4-yl)-ethoxy]-phenyl}-propionic acid methyl ester The title compound (542 mg) was prepared from 931 mg (2.48 mmol) of Intermediate 23 and 825 mg (2.48 mmol) of Intermediate 103 according to the method of Intermediate 44 followed by purification via silica gel flash column chromatography using hexanes/EtOAc (2:1 Æ 1:1) as eluent to give 867 mg of impure intermediate. A solution of 830 mg (1.2 mmol) this material in 12 mL of CH$_3$CN at 0° C. was treated with 0.222 mL (1.8 mmol) of BF$_3$.OEt$_2$. After stirring for 30 min at 0° C. then at 25° C. for 1 h, an additional 0.444 mL (3.6 mmol) of BF$_3$.OEt$_2$ was added. After stirring for a further 1 h, an additional 0.444 mL (3.6 mmol) of BF$_3$.OEt$_2$ was added and stirring was continued for 35 min. The reaction was poured into saturated NaHCO$_3$, and the product was extracted with EtOAc. The combined organic layers were dried (Na$_2$SO$_4$), filtered, and concentrated in vacuo. The residue was purified by silica gel flash column chromatography using hexanes/EtOAc (1:1) as eluent: low resolution MS (ES) m/e 560 (MH$^+$).

Intermediate 105

5-methyl-2-phenyl4-thiazoleacetic acid methyl ester

The title compound (827 mg) was prepared from 1.0 g (4.78 mmol) of methyl 4-bromo-3-oxo-pentanoate and 2.6 g (19.14 mmol) of thiobenzamide according to the method of Intermediate 42 followed by purification via silica gel flash column chromatography using hexanes/EtOAc (3:1) as eluent: low resolution MS (ES) m/e 270 (MNa$^+$), 248 (MH$^+$).

Intermediate 106

2-(5-methyl-2-phenyl-thiazol-4-yl)ethanol

The title compound (538 mg) was prepared from 817 mg (3.30 mmol) of Intermediate 105 according to the method of Intermediate 43 followed by purification via silica gel flash column chromatography using hexanes/EtOAc (1:2) as eluent: low resolution MS (ES) m/e 242 (MNa$^+$), 219 (MH$^+$).

Intermediate 107

2S-(2-benzoyl-phenylamino)-3-{4-[2-(5-methyl-2-phenyl-thiazol-4-yl)-ethoxy]-phenyl}-propionic acid methyl ester The title compound (378 mg) was prepared from 348 mg (0.93 mmol) of Intermediate 23 and 203 mg (0.93 mmol) of Intermediate 106 according to the method of Intermediate 43 followed by purification via silica gel flash column chromatography using hexanes/EtOAc (3:1) as eluent: low resolution MS (ES) m/e 599 (MNa$^+$), 577 (MH$^+$).

Intermediate 108

Methyl 3-(5-methyl-2-thienylamino)-4-oxopentanoate

A slurry of 19.3 g (0.136 mol) 5-methyl-2-thiophenecarboxylic acid in 200 mL of toluene was treated with 10.9 mL (0.15 mol) of thionyl chloride. The resulting mixture was heated to 70° C. for 16 h, then concentrated in vacuo. The resulting oil was added in portions to a solution of 25.0 g (0.136 mol) of b-methylaspartic acid hydrochloride in 80 mL of pyridine at 0° C. at a rate to maintain a temperature <10° C. After the addition was complete the solution was allowed to stir at 25° C. for 1 h, treated with 50 mL of acetic anhydride and heated to 90° C. for 2 h. The mixture was then cooled to 25° C., poured into 700 mL of 1N HCl, and extracted three times with EtOAc. The combined organic phases were washed three times with 3 N HCl, once with water, once with 5% Aq NaHCO$_3$, and finally with brine. The solution was dried (Na$_2$SO$_4$), then chromatographed over silica gel eluting with hexanes:EtOAc 3//2 to obtain 9.1 g (25%) of the title compound as a clear yellow oil: MS (ES+) m/e 270 (MH+).

Intermediate 109

(5-methyl-2-(5-methyl-2-thienyl)-oxazo-4-yl) acetic acid methyl ester

A solution of 3.97 g (14.7 mmol) of Intermediate 108 in 100 mL of anhydrous acetonitrile was treated with 4.1 mL (44.2 mmol) of phosphorous oxychloride and heated to reflux for 5 h. The solution was cooled to 25° C. and a dark oil was decanted from the tar at the bottom of the flask. The solution was concentrated in vacuo and diluted with water and EtOAc. The aqueous layer was saturated with KHCO$_3$, the layers were separated and the solution was extracted twice more with EtOAc. The combined organic phases were dried (Na$_2$SO$_4$) and concentrated in vacuo to give an orange oil, which was chromatographed over silica gel eluting with dichloromethane:EtOAc 20/1. The residue after concentration in vacuo was rechromatographed over silica gel eluting with hexane:EtOAc 2/1 to obtain 2.94 g (79%) of the title compound as a pink-orange oil: MS (API+) m/e 252 (MH+).

Intermediate 110

2-(5-methyl-2-(5-methyl-2-thienyl)-oxazol-4-yl) ethanol

The title compound (1.05 g) was prepared from 2.94 9 (11.7 mmol) of Intermediate 109 according to the method of Intermediate 43 followed by purification via silica gel chromatography eluting with hexanes:EtOAc 1/1: MS (API+) m/e 224 (MH+).

Intermediate 111

2(S)-(2-benzoyl-phenylamino)-3-{4-[2-5-methyl-2-(5-methyl-2-thienyl)-oxazol-4-yl)-ethoxy]-phenyl}-propionic acid methyl ester The title compound (440 mg) was prepared from 700 mg (3.13 mmol) of Intermediate 110 and 1.18 g (3.13 mmol) of Intermediate 23 according to the method of Intermediate 44 followed by purification via silica gel chromatography eluting with toluene:EtOAc 20/1: MS (ES+) m/e 581 (MH+); TLC (PhMe:EtOAc/90:10): R$_f$=0.25.

Intermediate 112

2(S)-(2-benzoyl-phenylamino)-3-{4-[2-(5-methyl-2-(3-methyl-thien-2-yl)-oxazol-4-yl)-ethoxy]-phenyl}-propionic acid methyl ester The title compound (100 mg) was prepared from 3.7 9 of (5-methyl-2-(3-methyl-2-thienyl)-oxazo-4-yl) acetic acid methyl ester (prepared analogously to Intermediate 109) according to the method of Intermediate 43 followed by reaction with 375 mg (1.0 mmol) of Intermediate 23 according to the method of Intermediate 44, followed by purifica-

Intermediate 113

2-(2-iodo-phenyl)-3-{4-[2-(benzoxazol-2-yl-methyl-amino)-ethoxy]-phenyl}-propionic acid methyl ester To a solution of 2.88 g (13.15 mmol) of 2-iodoaniline stirred in 50 mL of toluene under a nitrogen atmosphere at 25° C. was added 26.3 mL of a 0.1 M solution of Intermediate 10 in toluene, followed by 58 mg (0.132 mmol) of rhodium (II) acetate dimer. The resulting solution was stirred for 16 h at 25 C, then concentrated in vacuo to a dark brown oil. The crude product was chromatographed over silica gel eluting with $CH_2Cl_2$ to obtain 1.12 g (75%) of the title compound: MS (API) m/e 573 (MH+), 572 (M+).

Intermediate 114

4(R)-Hydroxymethyl-thiazolidine-3-carboxylic acid tert-butyl ester

A solution of 4.66 g (20 mmol) of N-Boc-thioproline and 3.84 mL (22 mmol) DIEA dissolved in 10 mL THF was cooled to 0_C and treated with 2.1 mL (22 mmol) of ethyl chloroformate. After 30 min at RT the white precipitate is filtered off, the solution cooled to 0° C. and a solution of 8.32 g (220 mmol) sodium borohydride in 30 mL $H_2O$ is added dropwise. The reaction was stirred for 24 h, then cooled to 0° C. and quenched by dropwise addition of acetic acid. The product was then extracted with EtOAc, the combined organics were washed successively with sodium bicarbonate and citric acid, dried with magnesium sulfate, filtered and solvents removed in vacuo to provide 2.33 g of the title compound: MS (ES+) m/e 242 (M+23), 120 (M-Boc+1).

Intermediate 115

4(R)-{4-[2(S)-(2-Benzoyl-phenylamino)-2-methoxycarbonylethyl]-phenoxymethyl}-thiazolidine-3-carboxylic acid tert-butyl ester A solution of 1.20 g (5.48 mmol) of Intermediate 114, 2.05 g (5.48 mmol) of Intermediate 23 and 1.58 g (6.03 mmol) of the triphenylphosphine in 7 mL of THF was dropwise added 0.95 mL (6.03 mmol) of DEAD at 0° C. The reaction mixture was stirred at RT for 1 h, solvents removed in vacuo and the crude mixture purified via silica gel column chromatography using EtOAc/hexane 1/3 as eluent to afford 530 mg of the title compound: MS (ES+) m/e 599 (M+23).

Intermediate 116

3-[4-(3-Benzoxazol-2-yl-thiazolidin-4(R)-ylmethoxy)-phenyl]-2(S)-(2-benzoyl-phenylamino)-propionic acid methyl ester Intermediate 115 (500 mg, 0.868 mmol) was treated with 5 mL of 4N HCl in dioxane for 1.5 h. Solvents were then evaporated and the crude hydrochloride salt dissolved in 20 mL dichloromethane. To this solution was added 767 mg (5.0 mmol) of chiorobenzoxazole and 1.29 g (10.0 mmol) of DIEA and allowed the resulting solution was stirred at RT for 36 h. The volatiles were then removed in vacuo, and the solid residue purified by silica gel flash column chromatography using EtOAc/hexane 1:1 as eluent to afford 128 mg of the title compound: MS (ES+) m/e 594 (MH+).

Intermediate 117

2(S)-(2-Benzoyl-phenylamino)-3-(4-hydroxyphenyl)-propionic acid

The title compound (1.63 g) was prepared from 1.79 g (4.66 mmol) of Intermediate 23 according to the method of Example 32: MS (ES+) m/e 384 (MH+23).

Intermediate 118

2(S)-(2-Benzoyl-phenylamino)-3-(4-hydroxy-phenyl)-propionic acid (2-chloro-phenyl)-diphenyl-methyl ester attached to polystyrene resin A solution of 1.63 g (4.4 mmol) of Intermediate 117 in 10 mL of MeOH and 5 mL of water was treated with 0.852 (4.4 mmol) of cesium bicarbonate. The solution was stirred for 10 min at RT, then solvents were removed and the resulting solid cesium salt dried in vacua. A slurry of 480 mg of the Cl-Trityl-polystyrene (PS) resin (substitution 1.5 mmol/g) in 4 mL of dry DMF was treated with 60 mg (~1 mmol) of the cesium salt described above and reacted for 20 h at 50° C. Resin was then filtered off and washed successively 10× with DMF, 1:1 DMF/ethanol, ethanol and ethyl ether, resulting in 550 mg of the dry product. The substitution (0.49 mmol/g) of this derivatized resin was then calculated based on the combustion analysis ($C_{found}$ 79.46%, $H_{found}$ 5.94%, $N_{found}$ 0.68%).

Intermediate 119

2(S)-(tert-butoxycarbonyl-amino)-3-{4-[2-(5-methyl-2-phenyl-oxazol-4-y)-ethoxy]-phenyl}-propionic acid methyl ester The title compound (15.9 g) was prepared from 15.0 g (73.8 mmol) of 2-(5-methyl-2-phenyl)-oxazol-4-yl)-ethanol and 21.8 g (73.8 mmol) of 2(S)-(tert-butoxycarbonyl-amino)-3-(4-hydroxyphenyl)-propionic acid methyl ester according to the method of Intermediate 44 followed by purification via silica gel chromatography using diethyl ether/dichloromethane (1:19): low resolution MS (ES) m/e 481 (MH$^+$).

Intermediate 120

2(S)-amino-3-{4-[2-(5-methyl-2-phenyl-oxazol-4-yl)-ethoxy]-phenyl}-propionic acid methyl ester To a stirred solution of 15.92 g (33.1 mmol) of Intermediate 119 in 300 mL of dichloromethane at RT was added 33 mL (10% volume) of trifluoroacetic acid. After stirring 5 h, the reaction was quenched with 0.1 N NaOH and the layers separated. The organics were washed with water, the layers separated, the organics dried ($MgSO_4$), and the solvent remove in vacuo to give the title compound as the monotrifluoro acetate salt: low resolution MS (ES) m/e 381 (MH$^+$).

Intermediate 121

2-diazo-3-{4-[2-(5-methyl-2-phenyl-oxazol-4-yl)-ethoxy]-phenyl}-propionic acid methyl ester The title compound (240 mg) was prepared from 500 mg (1.01 mmol) of Intermediate 120 according to the method of Intermediate 9 followed by purification via silica gel chromatography using EtOAc/hexane (3:7) as eluent: low resolution MS (ES) m/e 364 (M–N$_2$)$^+$.

Intermediate 122

2-[2-iodo-phenylamino]-3-{4-[2-(5-methyl-2-phenyl-oxazol-4-yl)-ethoxy]-phenyl}-propionic acid methyl ester The title compound (3.93 g) was prepared from Intermediate 121 (3.08 g, 7.87 mmol), 2-iodoaniline (2.07 g, 9.44 mmol) and Rh$_2$OAc$_4$ (100 mg) according to the method of Intermediate 3 followed by purification via silica gel chromatography with hexane/EtOAc (85:15): low resolution MS (ES$^+$) m/e 583 (MH$^+$).

Intermediate 123

2-[2-(4-formyl-benzoyl)-phenylamino]-3-{4-[2-(5-methyl-2-phenyl-oxazol-4-yl)-ethoxy]-phenyl}-propionic acid methyl ester A suspension of $K_2CO_3$ (356 mg, 2.58 mmol) in dioxane (13 mL) containing Intermediate 122 (500 mg, 0.86 mmol), 4-formylphenyl boronic acid (193 mg, 1.29 mmol) and Pd(Cl)$_2$(PPh$_3$)$_2$ (18.0 mg, 26 mmol) was heated (100° C.) under 1 atm CO for 24 h. After cooling to RT, the mixture was partitioned between 50 mL each of water and EtOAc. The EtOAc solution was washed with 0.5 M NaOH (50 mL), water (50 mL) and brine (25 mL). This solution was dried over MgSO$_4$ and concentrated to a brown oil which was flash chromatographed on silica gel (150 g) with hexane/EtOAc (85:15) to obtain unreacted starting iodide (0.32 g, 64% yield) and the title compound (99.1 mg, 168 mmol, 20% yield) as a yellow oil: low resolution MS (ES) m/e 589 (MH$^+$).

Intermediate 124

2-[2-(3-formyl-benzoyl)-phenylamino]-3-{4-[2-(5-methyl-2-phenyl-oxazol-4-yl)-ethoxy]-phenyl}-propionic acid methyl ester Following the procedure for Intermediate 123 using 3-formyl benzeneboronic acid, the title compound was isolated (25% yield) as a yellow oil: low resolution MS (ES$^+$) m/e 589 (MH$^+$).

Intermediate 125

2(S)-(1-methoxycarbonyl-2-{4-{2-(5-methyl-2-phenyl-oxazol-4-yl)-ethoxy]-phenyl}-ethylamino)-benzoic acid methyl ester A solution of Intermediate 120 (664 mg, 1.75 mmol) and methyl cyclohexanone-2-carboxylate (300 mg, 1.92 mmol) in toluene (50 mL) was refluxed for 16 h under $N_2$ into a Dean-Stark trap (oil bath temp of 130°). The toluene was then removed by rotary evaporation and replaced with anisole (50 mL). To this solution was added 10% palladium on carbon (250 mg) and the resulting suspension heated to 190° and stirred for 6 h under $N_2$. After cooling to room temperature the catalyst was removed by filtration through a pad of Celite (5 g) with an EtOAc wash (200 mL). The filtrate was concentrated to a brown oil which was flash chromatographed on silica gel (100 g) with hexane/EtOAc (4/1) to provide the title compound (590 mg, 66%) as a white solid: mp 102–103° C.; low resolution MS (ES$^+$) m/e 515 (MH$^+$).

Intermediate 126

2-(S)-(1-methoxycarbonyl-2-{4-{2-(5-methyl-2-phenyl-oxazol-4-yl)-ethoxy]-phenyl}-ethylamino)-benzoic acid A suspension of $K_2CO_3$ (267 mg, 1.9 mmol) in dioxane (50 mL) and water (0.1 mL) containing Intermediate 122 (375.2 mg, 0.64 mmol) and Pd(Cl)$_2$(PPh$_3$)$_2$ (22.6 mg, 0.032 mmol) in a 250 mL volume Parr bomb was stirred at 125° under CO (200 psi) for 16 h. After cooling to room temperature and venting the CO, the resulting mixture was diluted with EtOAc (250 mL) and washed with 2.0 M HCl and brine (50 mL each). The organic solution was dried over MgSO$_4$ and concentrated to a brown oil which was flash chromatographed on silica gel (50 g) with EtOAc/hexane (1/1 with 0.1% HOAc) to afford the title compound (110 mg, 34%) as a white solid: mp 173–174° C.; low resolution MS (ES$^+$) m/e 501 (MH$^+$).

Intermediate 127

(2S)-2-(1-methoxycarbonyl-2-{4-hydroxyphenyl}-ethylamino)-benzoic acid methyl ester A solution of 20.0 g (0.10 mol) of (L)-tyrosine methyl ester and 28.8 g (0.18 mol, 1.8 equiv.) of methyl cyclohexanone-2-carboxylate in 300 mL of toluene is heated to reflux for 2 h, with removal of $H_2O$ via a Dean-Stark trap. The resulting yellow solution was cooled to RT and the toluene was removed in vacuo. The residue was dissolved in 250 mL of anisole, and 5.0 g of 10% Pd/C was added. The resulting mixture was heated to 200° C. for 7 h, cooled to RT, an additional 5.0 g of 10% Pd/C was added and the mixture reheated to 200° C. for an additional 7 h. The reaction mixture was cooled to RT and filtered through a pad of Celite to remove the Pd. The filtrate was concentrated in vacuo at 60° C., and the residue purified by silica gel flash column chromatography using hexane/EtOAc 7/3 as eluent to afford a light yellow solid. This material was triturated with diethyl ether/hexane 1/1 and filtered to afford 15.75 g (47%) of the title compound as a white solid: low resolution MS (ES$^+$) m/e 330 (MH$^+$).

Intermediate 128

2-{4-[2-(benzoxazol-2-yl-methyl-amino)-ethoxy]-benzyl}-3-(3-benzyloxy-phenyl)-3-hydroxy-2,3-dihydro-1H-indole-2-carboxylic acid methyl ester The title compound (1.45 g) was prepared from 2.09 g (5.49 mmol) Intermediate 9, 2.0 g (6.59 mmol) of (2-aminophenyl)-(4-benzyloxy-phenyl)-methanone (*J. Org. Chem.*, 1991, 56 (11), 3750–3752) and 120 mg (0.27 mmol) of rhodium (II) acetate dimer according to the method of Intermediate 3 followed by purification via silica gel chromatography using EtOAc/hexane (gradient of 2:3 to 1:1) as eluent: low resolution MS (ES) m/e 678 (MNa$^+$), 656 (MH$^+$).

Intermediate 129

3-{4-[2-(benzoxazol-2-yl-methyl-amino)-ethoxy]-phenyl}-2-[2-(3-benzyloxy-benzoyl)-phenylamino propionic acid methyl ester To a stirred solution of 1.45 g (2.21 mmol) of Intermediate 128 in 22 mL of toluene was added 1.1 mL (7.52 mmol) of 1,8-Diazabicyclo[5.4.0]undec-7-ene. The resulting solution was heated to reflux for 16 h. After cooling to RT, the solvent was removed in vacuo. The residue was purified by silica gel chromatography using EtOAc/hexane (gradient of 2:3 to 1:1) as eluent to give 1.02 g (70% yield) of the title compound: low resolution MS (ES) m/e 678 (M+Na$^+$), 656 (MH$^+$).

Intermediate 130

3-{4-[2-(benzoxazol-2-yl-methyl-amino)-ethoxy]-phenyl}-2-[2-(3-hydroxy-benzoyl)-phenylamino]-propionic acid methyl ester A solution of 600 mg (0.91 mmol) of Intermediate 129 in 9 mL of EtOAc was evacuated and flushed with argon. To the solution was added 300 mg (50 wt %) of Palladium on carbon (10%). The resulting slurry was evacuated and flushed with argon. After stirring under 1 atm of hydrogen for 16 h, the reaction was filtered through celite under a stream of nitrogen. The organics were collected and the solvent removed in vacuo to yield the title compound which was used directly without further purification: low resolution MS (ES) m/e 588 (MNa$^+$), 566 (MH$^+$).

Intermediate 131

3-{4-[2-(5-methyl-2-phenyl-oxazol-4-yl)-ethoxy]-phenyl}-2-[2-(4-propylsulfamoyl-benzoyl)-phenylamino]-propionic acid methyl ester The title compound (70 mg) was prepared from 190 mg (0.77 mmol) 4-propylsulfamoyl-benzene boronic acid and 300 mg (0.52 mmol) of Intermediate 122 according to the method of Intermediate 126 followed by purification via silica gel chromatography using EtOAc/hexane (1:2) as eluent: low resolution MS (ES) m/e 704 (MNa$^+$), 682 (MH$^+$).

Intermediate 132

2-[2-(3-amino-benzoyl)-phenylamino]-3-{4-[2-(5-methyl-2-phenyl-oxazol-4-yl)-ethoxy]-phenyl}-propionic acid methyl ester The title compound (640 mg) was prepared from 400 mg (2.58 mmol) 3-aminobenzene boronic acid and 1.0 g (1.72 mmol) of Intermediate 122 according to the method of Intermediate 126 followed by purification via silica gel chromatography using EtOAc/hexane (2:3) as eluent: low resolution MS (ES) m/e 598 (MNa$^+$), 576 (MH$^+$).

Intermediate 133

2-[2-(3-methanesulfonylamino-benzoyl)-phenylamino]-3-{4-[2-(5-methyl-2-phenyl-oxazol-4-yl)-ethoxy]-phenyl}-propionic acid methyl ester To a stirred solution of 150 mg (0.26 mmol) of Intermediate 132 in 3 mL of dichloromethane at 0° C. was added 0.06 mL (0.78 mmol) of pyridine and 0.02 mL (0.29 mmol) of methanesulfonyl chloride. After warming to RT over 1.25 h, the reaction was washed with Sat. NaHCO$_3$ and water, the layers separated, organics dried (Na$_2$SO$_4$), and the solvent removed in vacuo. The residue was purified by silica gel chromatography with EtOAc/hexane (1:1) as eluent to give 60 mg (35% yield) of the title compound: low resolution MS (ES) m/e 654 (MH$^+$).

Intermediate 134

2-[2-(3-methoxycarbonylamino-benzoyl)-phenylamino]-3-{4-[2-(5-methyl-2-phenyl-oxazol-4-y)-ethoxy]-phenyl}-proplonic acid methyl ester To a stirred solution of 180 mg (0.31 mmol) of Intermediate 132 in 3 mL of dichloromethane was added 65 mL (0.47 mmol) of triethylamine. The solution was cooled to 0° C. and 0.27 mL (0.34 mmol) of methylchloroformate added. After warming to RT overnight, the solvent was removed in vacuo and the residue purified by silica gel chromatography using EtOAc/hexane (2:3) as eluent to give 50 mg (25% yield) of the title compound: low resolution MS (ES) m/e 634 (MH$^+$).

Intermediate 135

2-[2-(3-benzyloxy-benzoyl)-phenylamino]3-{4-[2-(5-methyl-2-phenyl-oxazol-4-yl)-ethoxy]-phenyl}-propionic acid methyl ester The title compound (580 mg) was prepared from 480 mg (2.06 mmol) 3-benzyloxy benzene boronic acid and 0.8 g (1.37 mmol) of Intermediate 122 according to the method of Intermediate 126 followed by purification via silica gel chromatography using EtOAc/hexane (gradient of 3:17 to 1:4) as eluent: low resolution MS (FAB) m/e 667 (MH$^+$).

Intermediate 136

2-[2-(3-hydroxy-benzoyl)-phenylamino]-3-{4-[2-(5-methyl-2-phenyl-oxazol-4-yl)-ethoxy]-phenyl}-propionic acid methyl ester A solution of 100 mg (0.15 mmol) of Intermediate 135 in 1.5 mL of EtOAc was evacuated and flushed with argon. To the solution was added 110 mg (100 wt %) of Palladium on carbon (10%). The resulting slurry was evacuated and flushed with argon. After stirring under 1 atm of hydrogen for 16 h, the reaction was filtered through celite under a stream of nitrogen. The organics were collected and the solvent removed in vacuo. The residue was purified by silica gel chromatography using EtOAc/hexane (3:7) as eluent to give 56 mg (37% yield) of the title compound: low resolution MS (FAB) m/e 577 (MH$^+$).

Intermediate 137

2-[2-(3-Carbanoylmethoxy-benzoyl)-phenylamino]-3-{4-[2-(5-methyl-2-phenyl-oxazol-4-yl)-ethoxy]-phenyl}-propionic acid methyl ester To a stirred solution of 100 mg (0.17 mmol) of Intermediate 136 in 2 mL of anhydrous THF at 0° C. was added 8 mg (0.19 mmol) of a 60% suspension of NaH. After stirring for 5 min, 24 mg (0.17 mmol) of 2-bromoacetamide was added to the slurry. The solution was warmed to RT, diluted with water, and extracted with EtOAc. The layers were separated, the organics dried (Na$_2$SO$_4$), and the solvent removed in vacuo to give a yellow solid. The solid was purified by trituration with hexane to give 73 mg (66% yield) of the title compound: low resolution MS (ES) m/e 656.2 (MNa$^+$), 634 (MH$^+$).

Intermediate 138

3-azido-4-oxo-pentanoic acid methyl ester

To a solution of 2.23 g (10.67 mmol) of 3-bromo4-oxo-pentanoic acid methyl ester in 11 mL of DMF at 0° C. was added 690 mg (10.67 mmol) of sodium azide. After warming to RT over 2.5 h, the reaction was diluted with water and extracted with diethyl ether/hexane (1:1). The layers were separated, the organics dried (Na$_2$SO$_4$), and the solvent removed in vacuo. The residue was purified by silica gel chromatography using diethyl ether/hexane (gradient of 1:4 to 2:3) to give 1.07 g (58% yield) of the title compound: low resolution MS (FAB) m/e 172 (MH$^+$).

Intermediate 139

3-amino-4-oxo-pentanoic acid methyl ester

A solution of 1.0 g (5.8 mmol) of Intermediate 138 in 25 mL of MeOH was evacuated and flushed with argon. To the solution was added 290 mg (30 wt %) of Palladium on carbon (10%). The resulting slurry was evacuated and flushed with argon. After stirring under 1 atm of hydrogen for 4 h, the reaction was filtered through celite under a stream of nitrogen. The organics were collected and the solvent removed in vacuo to give 940 mg (90% yield) of the title compound which was used without further purification: low resolution MS (ES) m/e 146 (MH$^+$).

Intermediate 140

4-oxo-3-[(pyridine-4-carbonyl)-amino]-pentanoic acid methyl ester

To a stirred solution of 940 mg (5.18 mmol) Intermediate 139 in 52 mL of dichloromethane at 0° C. was added 2.9 mL (20.72 mmol) of triethylamine. After stirring for 5 min, 1.0 g (5.69 mmol) of isonicotinoyl chloride hydrochloride was added and the reaction allowed to warm to RT overnight. The stirred solution was diluted with water, the layers separated, organics dried ($MgSO_4$), and the solvent removed in vacuo. The residue was purified by silica gel chromatography using MeOH/EtOAc (gradient of 0:1 to 1:19) to give 360 mg (28% yield) of the title compound: low resolution MS (ES) m/e 251 ($MH^+$).

Intermediate 141

(5-methyl-2-pyridin-4-yl-oxazol-4-yl)-acetic acid methyl ester

To a stirred solution of 250 mg (1.0 mmol) of Intermediate 140 in 7 mL of anhydrous toluene was added 0.28 mL (3.0 mmol) of $POCl_3$ (fresh ampule) and the reaction heated to reflux for 16 h. After cooling to RT, the reaction was diluted with EtOAc and the organics washed with Sat. $NaHCO_3$, dried ($MgSO_4$), and the solvent removed in vacuo. The residue was purified by silica gel chromatography using MeOH/EtOAc (1:19 with 0.1% $NH_4OH$) as eluent to give 180 mg (78% yield) of the title compound: low resolution MS (ES) m/e 233 ($MH^+$).

Intermediate 142

2-(5-methyl-2-pyridin-4-yl-oxazol-4-yl)-ethanol

The title compound (200 mg) was prepared from 285 mg (1.23 mmol) of Intermediate 141 according to the method of Intermediate 43 followed by purification via silica gel column chromatography using MeOH/EtOAc (1:19) as eluent: low resolution MS (ES) m/e 205 ($MH^+$).

Intermediate 143

2(S)-(2-benzoyl-phenylamino)-3-{4-[2-(5-methyl-2-pyridin-4-yl-oxazol-4-yl)-ethoxy]-phenyl}-propionic acid methyl ester The title compound (210 mg) was prepared from 0.15 g (0.73 mmol) of Intermediate 142 and 0.27 g (0.73 mmol) of Intermediate 23 according to the method of Intermediate 44 followed by purification via silica gel chromatography using EtOAc/hexane (gradient of 1:1 to 9:1): low resolution MS (ES) m/e 562 ($MH^+$).

Intermediate 144

4-tert-butoxycarbonyl-piperazine-1-carbothioic acid amide

The title compound (1.5 g) was prepared from 3.01 g (16.91 mmol) of thiocarbonyldiimidazole and 3.0 g (16.12 mmol) of 1-tert-butoxycarbonyl-piperazine according to the method of Intermediate 53 followed by purification via trituration with diethyl ether: low resolution MS (ES) m/e 246 ($MH^+$).

Intermediate 145

[5-methyl-2-(4-tert-butoxycarbonyl-piperazin-1-yl)-thiazol-4-yl]-acetic acid methyl ester The title compound (1.18 g) was prepared from 1.2 g (4.89 mmol) of Intermediate 144 and 1.02 g (4.89 mmol) of methyl-4-bromo-3-oxo-pentanoate according to the method of Intermediate 60 followed by purification via silica gel chromatography using MeOH/dichloromethane (1:19) as eluent: low resolution MS (ES) m/e 356 ($MH^+$).

Intermediate 146

2-[5-methyl-2-(4-tert-butoxycarbonyl-piperazin-1-yl)-thiazol-4-yl]-ethanol

The title compound (820 mg) was prepared from 1.0 g (2.81 mmol) of Intermediate 145 according to the method of Intermediate 43 followed by purification via silica gel chromatography using MeOH/dichloromethane (1:19) as eluent: low resolution MS (ES) m/e 328 ($MH^+$).

Intermediate 147

2(S)-(2-benzoyl-phenylamino)-3-(4-{2-[5-methyl-2-(4-tert-butoxycarbonyl-piperazin-1-yl)-thiazol-4-yl]-ethoxy}-phenyl)-propionic acid methyl ester The title compound (490 mg) was prepared from 300 mg (0.92 mmol) of Intermediate 146 and 330 mg (0.87 mmol) of Intermediate 23 according to the method of Intermediate 45 followed by purification via silica gel chromatography using MeOH/dichloromethane (1:49) as eluent: low resolution MS (ES) m/e 707 ($MNa^+$), 685 ($MH^+$).

Intermediate 148

2(S)-(2-benzoyl-phenylamino)-3-{4-[2-(5-methyl-2-piperazin-1-yl-thiazol-4-yl)-ethoxy]-phenyl}-propionic acid methyl ester To a stirred solution of 650 mg (0.95 mmol) of Intermediate 147 in 10 mL of dichloromethane was added 1 mL of trifluoroacetic acid. After stirring for 1.5 h, the reaction was washed with water and Sat. $NaHCO_3$. The layers were separated, the organics dried ($MgSO_4$), and the solvent removed in vacuo. The residue was purified by silica gel chromatography using MeOH/EtOAc (1:4) as eluent to give 176 mg (32% yield) of the title compound: low resolution MS (ES) m/e 607 ($MNa^+$), 585 ($MH^+$).

Intermediate 149

2(S)-(2-benzoyl-phenylamino)-3-(4-{2-[5-methyl-2-(4-methylsulfonyl-piperazin-1-yl)-thiazol-4-yl]-ethoxy}-phenyl)-propionic acid methyl ester To a stirred solution of 170 mg (0.29 mmol) of Intermediate 148 in 3 mL of dichloromethane at 0° C. was added 0.07 mL (0.87 mmol) of pyridine and 0.025 mL (0.32 mmol) of methanesulfonyl chloride. After warming to RT, the reaction was washed with Sat. $NaHCO_3$ and water. The layers were separated, the organics dried ($MgSO_4$), and the solvent removed in vacuo. The residue was purified by silica gel chromatography using EtOAc/hexane (2:1) as eluent to give 140 mg (74% yield) of the title compound: low resolution MS (ES) m/e 663 ($MH^+$).

Intermediate 150

2(S)-(2-{4-[2-(5-methyl-2-phenyl-thiazol-4-yl)-ethoxy]-phenyl}-1-methoxycarbonyl-ethylamino)-benzoic acid methyl ester A suspension of 350 mg (1.37 mmol, 1.10 equiv) of triphenylphosphine, 395 mg (1.20 mmol) of Intermediate 127, and 290 mg (1.32 mmol) of Intermediate 106 in 10 mL of dry toluene was heated to 80° C. for 15 min to effect dissolution of Intermediate 127 to provide a clear colorless solution. To this solution was added 250 mg (1.26 mmol, 1.05 equiv) of diisopropyl azodicarboxylate dropwise over 5 min. The reaction was then allowed to cool to RT and stirred 16 h. The toluene was removed in vacuo, and then the residue was stirred vigorously for 1 h in 10 mL of 1:1 diethyl ether/1 N LiOH biphasic solution to effect selective removal of residual Intermediate 127. The layers were separated and the organic layer washed with $H_2O$, dried ($MgSO_4$), and solvent removed in vacuo. The material was purified by silica gel flash column chromatography using hexane/EtOAc 5/1 as eluent to afford 400 mg of the title compound as a white solid: low resolution MS (FAB)m/e 531 ($MH^+$).

Intermediate 151

2(S)-(2-{4-[2-(4-chloro-phenylsulfanyl)-ethoxy]-phenyl}-1-methoxycarbonyl-ethylamino)-benzoic acid methyl ester The title compound (118 mg) was prepared from 100 mg (0.30 mmol) of Intermediate 127 and 69 mg (0.36 mmol) of 2-(4-chlorophenylthio)-ethanol according to the method of Intermediate 150 followed by purification via silica gel flash column chromatography using hexane/EtOAc 5/1 as eluent: low resolution MS (FAB)m/e 500 ($M^+$).

Intermediate 152

2(S)-(2-{4-[2-(5-nitro-2-pyridyloxy)-ethoxy]-phenyl}-1-methoxycarbonyl-ethylamino)-benzoic acid methyl ester The title compound (109 mg) was prepared from 139 mg (0.754 mmol) of 2-(5-nitro-2-pyridyloxy)ethanol and 248 mg (0.754 mmol) of Intermediate 127 according to the method of Intermediate 150 followed by purification via flash chromatography (2:1Hex:EtOAc): low resolution MS m/e 496 (MH+).

Intermediate 153

2(S)-(2-{4-[2-(5-chloro-2-pyridylsulfanyl)-ethoxy]-phenyl}-1-methoxycarbonyl-ethylamino)-benzoic acid methyl ester The title compound (155 mg) was prepared from 156 mg (0.824 mmol) of 2-(5-chloropyrid-2-ylthio)ethanol and 271 mg (0.824 mmol) of Intermediate 127 according to the method of Intermediate 150 followed by purification via flash chromatography (4:1 Hex:EtOAc): $^1$H NMR ($CDCl_3$, 400 MHz) δ 8.39 (d, 1H, 2.3), 8.19 (d, 1H), 7.89 (dd, 1H, J=1.5, 8.0), 7.78 (d, 1H, J=2.5), 7.45 (dd, 1H, J=2.4, 8.5), 7.14 (d, 4H, J=8.5), 6.86 (d, 2H, 8.5), 6.62 (t, 1H, 7.6), 6.54 (d, 1H, J=8.4), 4.33 (q, 1H, J=6.7), 4.19 (t, 2H, J=6.7), 3.85 (s, 3H), 3.67 (s, 3H), 3.52 (t, 2H, J=6.7), 3.12 (ddd, 2H, J=5.4, 7.1, 7.1).

Intermediate 154

2(S)-(2-{4-[2-(N-ethyl-2-methyl-toluidino)-ethoxy]-phenyl}-1-methoxycarbonyl-ethylamino)-benzoic acid methyl ester The title compound (90 mg) was prepared from 123 mg (0.687 mmol) of 2-(N-ethyl-m-toluidino)ethanol and 226 mg (0.687 mmol) of Intermediate 127 according to the method of Intermediate 150 followed by purification via by flash chromatography (4:1 Hex:EtOAc): low resolution MS m/e 491 (MH+).

Intermediate 155

2(S)-(2-{4-[2-(4-dimethylamino-phenyl)-ethoxy]-phenyl}-1-methoxycarbonyl-ethylamino)-benzoic acid methyl ester The title compound (290 mg) was prepared from 110 mg (0.64 mmol) of 4-(dimethylamino) phenethyl alcohol and 200 mg (0.61 mmol) of Intermediate 127 according to the method of Intermediate 150 followed by purification via silica gel chromatography using triethylamine/EtOAc/hexane (1:4:15) as eluent: low resolution MS (ES) m/e 499 ($MNa^+$).

Intermediate 156

2(S)-[1-methoxycarbonyl-2-(4-{2-[5-methyl-2-(4-methyl-piperazin-1-yl)-thiazol-4-yl]-ethoxy}-phenyl)-ethylamino]-benzoic acid methyl ester The title compound (360 mg) was prepared from 187 mg (0.77 mmol) of Intermediate 71 and 240 mg (0.74 mmol) of Intermediate 127 according to the method of Intermediate 150 followed by purification via silica gel chromatography using MeOH/EtOAc (1:9) as eluent: low resolution MS (ES) m/e 553 ($MH^+$).

Intermediate 157

2(S)-(2-{4-[2-(4-chloro-phenyl)ethoxy]-phenyl}-1-methoxycarbonyl-ethylamino)-benzoic acid methyl ester The title compound (230 mg) was prepared from 100 mg (0.64 mmol) of 4-chloro phenethyl alcohol and 200 mg (0.61 mmol) of Intermediate 127 according to the method of Intermediate 150 followed by purification via silica gel chromatography using EtOAc/hexane (1:3 with 1% TEA) as eluent: low resolution MS (ES) m/e 490 ($MNa^+$), 468 ($MH^+$).

Intermediate 158

2-(4-trifluoromethoxy-phenyl)-ethanol

To a stirred solution of 1.0 g (4.54 mmol) of 4-(trifluoromethoxy)-phenylacetic acid in 15 mL of anhydrous THF at 0° C. was added dropwise 9 mL (9.08 mmol) of 1 M $BH_3THF$ and the reaction allowed to warm to RT over 16 h. The mixture was cooled back down to 0° C. and the reaction quenched with 15 mL of water/acetic acid/THF (1:1:3). After warming to RT, the solvent was removed in vacuo, the residue diluted with water, and the solution extracted with EtOAc. The layers were separated, the organics washed with $NaHCO_3$, the layers separated, the organics dried ($MgSO_4$), and the solvent removed in vacuo. The residue was purified by silica gel chromatography using EtOAc/hexane (1:1) as eluent to give 540 mg (57% yield) of the title compound: TLC (EtOAc/hexane (1:1)): $R_f$=0.43.

Intermediate 159

2(S)-(1-methoxycarbonyl-2-{4-[2-(4-trifluoromethoxy-phenyl)-ethoxy]-phenyl}-ethylamino)-benzoic acid methyl ester The title compound (280 mg) was prepared from 130 mg (0.64 mmol) of Intermediate 158 and 200 mg (0.61 mmol)

of Intermediate 127 according to the method of Intermediate 150 followed by purification via silica gel chromatography using EtOAc/hexane (1:3) as eluent: low resolution MS (ES) m/e 540 (MNa$^+$).

Intermediate 160

2-{4-[2-(Benzoxazol-2-yl-methylamino)-ethoxy]-benzyl}-3-hydroxy-3-phenyl-2,3-dihydro-1H-thieno [3,4-b]pyrrole-2 carboxylic acid methyl ester The title compound (100 mg) was prepared from 198 mg (0.52 mmol) of Intermediate 9 and 160 mg (0.79 mmol) of 2-amino-3-benzoylthiophene (Hromatka, O. et. al., *Monatsh. Chem.* 1973, 104(6), 1513–19) according to the method of Intermediate 3 followed by purification via silica gel chromatography eluting with 20–40% EtOAc in hexanes: low resolution MS (Cl) m/e 556 (MH$^+$).

Intermediate 161

3-(4-Hydroxyphenyl)-2-(2-(4-biphenylcarbonyl)-phenylamino)-propionic acid methyl ester The title compound (830 mg) was prepared from 1.83 g (5.7 mmol) O-benzyl-L-tyrosine methyl ester and 1.59 g (5.7 mmol) of 2-(4-phenylbenzoyl)cyclohexanone (Child, R. G. et.al. J. Pharm Sci 1977, 66(4), 466–76) according to the method of Intermediate 23 followed by purification via silica gel chromatography eluting with 1/9 EtOAc/hexanes: Low resolution MS (Cl) m/e 452 (MH$^+$).

Intermediate 162

3-{4-[2-(Benzoxazol-2-yl-methylamino)-ethoxy]-phenyl}-2-(2-(4-biphenylcarbonyl)-phenylamino)-propionic acid methyl ester To a DMF solution (5 mL) of Intermediate 161 (0.78 g, 1.73 mmol) was added 57 mg of 80% NaH followed by 0.47 g (1.73 mmol) of Intermediate 6 in 5 mL DMF. The mixture was stirred for 18 h at 80° C., quenched with water (5 mL), concentrated to dryness, and extracted from 30 mL water with EtOAc(3×30 mL). The organics were dried (MgSO$_4$), concentrated, and purified by silica gel chromatography eluting with 1/1 EtOAc/hexanes to give 0.90 g of the title compound: low resolution MS (Cl) m/e 626 (MH+).

Intermediate 163

3-(4-Hydroxyphenyl)-2-(2-(4-methoxybenzoyl)-phenylamino)-propionic acid methyl ester The title compound (2.31 g) was prepared from 4.64 g (20 mmol) of 2-(4-methoxybenzoyl)-cyclohexanone (Howard, A. S. et. al. Tetrahedron Lett. 1979, (15), 1339–40) and 6.43 g (20 mmol) of O-benzyl-L-tyrosine methyl ester hydrochloride as a yellow solid as described for Intermediate 161: low resolution MS (Cl) m/e 406 (MH$^+$).

Intermediate 164

3-{4-[2-(Benzoxazol-2-yl-methylamino)-ethoxy]-phenyl}-2-(2-(4-methoxybenzoyl)-phenylamino)-propionic acid methyl ester The title compound (0.34 g) was prepared from Intermediate 163 (0.5 g, 1.23 mmol) and Intermediate 6 (0.33 g, 1.23 mmol) as described above for Intermediate 162: low resolution MS (Cl) m/e 581 (MH$^+$).

Intermediate 165

3-{4-[2-(Benzoxazol-2-yl-methylamino)-ethoxy]-phenyl}-2-(2-(4-methylbenzoyl)-phenylamino)-propionic acid methyl ester The title compound (810 mg) was prepared from 0.6 g (1.58 mmol) Intermediate 9 and 1.0 g (4.73 mmol) of 2-amino-4'-methylbenzophenone (Frye, S. V. et. al. *J. Org. Chem.* 1991, 56(11), 3750–52) according to the method of Intermediate 3 followed by purification via silica gel chromatography eluting with 30–50% EtOAc in hexanes: low resolution MS (ESP$^+$) m/e 586 (M+Na$^+$).

Intermediate 166

3-{4-[2-(Benzoxazol-2-yl-methylamino)-ethoxy]-phenyl}-2-(2-(2-methylbenzoyl)-phenylamino)-propionic acid methyl ester The title compound (800 mg) was prepared from 628 mg (1.65 mmol) of Intermediate 9 and 523 mg (2.48 mmol) of 2-amino-2'-methylbenzophenone (Frye, S. V. et. al. *J. Org. Chem.* 1991, 56(11), 3750–52) according to the method of Intermediate 3 followed by purification via silica gel chromatography, eluting with 20–40% EtOAc in hexanes: low resolution MS (Cl) m/e 564 (MH$^+$).

EXAMPLES

Example 1

3-(4-Benzyloxy-phenyl)-2(S)-(1-methyl-3-oxo-3-phenyl-propenylamino)-propionic acid dicyclohexylamine salt A stirred mixture of 5.42 g (20 mmol) o-benzyl-L-tyrosine, 4.4 mL (22 mmol) dicyclohexylamine and 3.24 g (20 mmol) 1-benzoylacetone in 100 mL MeOH was refluxed for 24 h. 500 mL abs. ethanol was then added slowly to the solution and the MeOH was distilled out from the reaction flask with the same rate. The solution was then cooled to 0° C., stirred for 30 min, then filtered. The white solid was washed with 15 mL cold (–20° C.) abs. ethanol three times then dried to yield 7.60 g of the title compound: low resolution MS (FAB+) m/e 597 (MH+), 182 (DCAH+); Anal. ($C_{38}H_{48}N_2O_4$) Calcd. C, 76.47; H, 8.10; N, 4.69 Found C, 76.44; H, 8.16; N 4.63.

Example 2

3-(4-Benzyloxy-phenyl)-2(S)-(1-methyl-3-oxo-3-phenyl-propenylamino)-propionic acid methyl ester To a stirred suspension of 2.98 g (5 mmol) of Example 1 and 1.50 g (10.8 mmol) anhydrous potassium carbonate in 30 mL anhydrous dimethylformamide 0.37 mL (6 mmol) methyl iodide was added in one portion. The mixture was stirred for 1 h, then an additional amount of 0.5 mL (8 mmol) methyl iodide was added. The suspension was stirred for an additional 20 min, then it was diluted with 100 mL ether. 100 mL brine was added, and the phases were separated. The organic phase was extracted with 200 mL brine six times, then the organic phase was dried with anhydrous magnesium sulfate, and filtered. The filtrate was concentrated under reduced pressure. The residue was purified by flash chromatography (SiO$_2$, eluent: Hexane/EtOAc(5:1) then hexane/EtOAc (1:1)) to yield 1.4 g of the of the title compound: low resolution MS (ESP+) m/e 430 (MH+); Anal. ($C_{27}H_{27}NO_4$) Calcd. C, 75.50; H, 6.33; N, 3.26; Found C, 75.41; H, 6.35; N 3.28.

Example 3

2(S)-(2-Benzoyl-cyclohex-1-enylamino)-3-(4-benzyloxy-phenyl)-propionic acid dicyclohexylamine salt A stirred mixture of 1.35 g (5 mmol) o-benzyl-L-tyrosine, 1.0 mL (5 mmol) dicyclohexylamine and 1.01 g (5 mmol) 2-benzoylcyclohexanone (Denny, William A.; Cain, Bruce F.; J. Med. Chem. (1978), 21(5), 430–7.) in 25 mL MeOH was refluxed for 24 h. The solution was then cooled to 20° C., and the solvent was evaporated under reduced pressure. Purification of the residue by flash chromatography using Hexane/EtOAc (1:1) then EtOAc (neat), finally $CHCl_3$/MeOH (10:1) as eluents resulted in 1.4 g of the of the title compound. 1H NMR (DMSO-d6, 400 MHz) δ 12.00 (d, 1H, J=8.4) 7.3 (m, 10H), 7.13 (d, 2H, J=8.5), 6.85 (d, 2H, J=8.5), 5.01 (s, 2H), 4.02 (m, 1H), 3.05 (m, 1H), 2.89 (m, 2H), 2.73 (dd, 1H, J=8.5, 13.7), 2.25 (m, 1H), 2.03 (m, 3H) 1.93 (m, 3H), 1.66 (m, 3H), 1.53 (d, 2H, J=12.3), 1.30 (m, 2H), 1.20 (m, 12H), 1.03 m (2H); low resolution MS (ESP+) m/e 456 (MH+).

Example 4

2-(2-benzoylphenylamino)-3-(4-benzyloxyphenyl) propanoic acid

To a solution of 185 mg (0.62 mmol) of Intermediate 2 in 8 mL (1:1; dioxane:water) was added 500 mg (11.9 mmol) lithium hydroxide monohydrate. The resulting suspension was stirred at 50° C. for 5 h and then cooled to RT. A 1M phosphoric acid solution was added until pH was 5.5 was reached where upon the resulting suspension was extracted with EtOAc (2×25 mL). The combined organic extracts were dried ($MgSO_4$), filtered, and concentrated and chromatographed on silica gel using $CH_2Cl_2$/MeOH (9:1) to yield 133 mg of the title compound. 1H NMR ($CDCl_3$) δ 8.87 (bs, 1H) 7.60–7.58 (d, 2H, J=6) 7.94–7.32 m (10H), 7.23–7.21 (d, 2H, J=3.9), 6.90–6.88 (m, 2H) 6.67–6.56 (m, 2H), 4.98 (s, 2H), 4.39 (m, 1H), 3.30–3.10 (m, 2H); low resolution MS (FAB+) m/e (MH+) 452.1.

Example 5

3-(4-Benzyloxy-phenyl)-2-(2-benzyloxy-phenylamino)-propionic acid methyl ester 3 mg (0.0067 mmol) rhodium(II) acetate dimer was added to stirred solution of 150 mg (0.50 mmol) of Intermediate 1 (Kawamatsu, Y. at al. Arzneim.-Forsch. 1980, 30(4), 585–9) and 113 mg (0.50 mmol) 2-Amino-benzoic acid benzyl ester in 5 mL toluene at 80° C. The mixture was stirred at 80° C. for 5 min, then cooled to room temperature. The solvent was removed under reduced pressure, and the residue was purified by flash chromatography using hexane/EtOAc (5:1) as eluent to yield 130 mg of the title compound. 1H NMR ($CDCl_3$, 400 MHz) δ 8.19 (d, 1H, J=7.3), 7.95 (dd, 1H, J=1.4, 7.9), 7.35 (m, 11H), 7.12 (d, 2H, J=8.5), 6.87 (d, 2H, J=8.5), 6.60 (t, 1H, J=7.5), 6.53 (d, 1H, J=8.6), 5.30 (s, 2H), 5.01 (s, 2H), 4.32 (q, 1H, J=6.4), 3.65 (s, 3H), 3.14 (dd, 1H, J=6.0, 13.6), 3.08 (dd, 1H, J=7.2, 13.7); low resolution MS (ESP+) m/e 496 (MH+).

Example 6

3-(4-Benzyloxy-phenyl)-2-(phenylcarbamoyl-phenylamino)-propionic acid methyl ester The title compound (54 mg) was prepared from 150 mg (0.50 mmol) of Intermediate 1 (Kawamatsu, Y. at al. Arzneim.-Forsch. 1980, 30(4), 585–9) and 110 mg (0.51 mmol) 2-amino-benzanilide according to the method of Example 5: 1H NMR ($CDCl_3$, 400 MHz) δ 7.83 (s, 1H), 7.66 (d, 1H, J=7.9), 7.54 (d, 2H, J=8.0), 7.47 (d, 1H, J=7.9), 7.35 (m, 8H), 7.13 (m, 3H), 6.85 (d, 2H, J=8.6), 6.68 (t, 1H, J=7.5), 6.61 (d, 1H, J=8.4), 4.96 (s, 2H), 4.30 (q, 1H, J=7.2), 3.64 (s, 3H), 3.10 (m, 2H); low resolution MS (ESP+) m/e 481 (MH+).

Example 7

3-(4-Benzyloxy-phenyl)-2-[2-(piperidine-1-carbonyl)-phenylamino]-propionic acid methyl ester The title compound (90 mg) was prepared from 150 mg (0.50 mmol) Intermediate 1 (Kawamatsu, Y. at al. Arzneim.-Forsch. 1980, 30(4), 585–9) and 103 mg (0.50 mmol) 2-amino-phenyl)-piperidin-1-yl-methanone (Ahern, T. P., et al. Can. J. Chem. 1976, 54(2), 290–6.) according to the method of Example 5 followed by purification by silica gel flash chromatography using hexane/EtOAc (1:1) as eluent: 1H NMR ($CDCl_3$, 400 MHz) δ 7.40 (m, 5H), 7.21 (t, 1H, J=8.2), 7.15 (m, 3H), 6.93 (d, 2H, J=8.7), 6.73 (t, 1H, J=7.4), 6.59 (d, 1H, J=8.2), 5.21 (d(broad), 1H, J=8.3), 5.06 (s, 2H), 4.30 (dd, 1H, J=7.9, 8.8), 3.69 (s, 3H), 3.45 (m, 4H), 3.10 (m, 2H), 1.55 (m, 6H); low resolution MS (ESP+) m/e 473 (MH+).

Example 8

2-(3-Benzoyl-thiophen-2-yl-amino)-3-(4-benzyloxy-phenyl)-propionic acid

A solution of 100 mg (1.78 mmol) potassium hydroxide in 1 mL water was added to a stirred solution of 120 mg (0.25 mmol) of Intermediate 3 in 10 mL MeOH. The mixture was stirred for 2 h at 20° C. then adjusted to pH=2 with 5% aqueous hydrochloric acid. 50 mL water was added to the mixture, the it was extracted with 20 mL methylene chloride three times. The organic phases were combined, dried with anhydrous magnesium sulfate, then concentrated under reduced pressure. The residue was purified by silica gel flash chromatography using EtOAc(neat) then EtOAc/EtOH (1:1) solvent mixtures as eluents to provide 27 mg of the title compound. 1H NMR (DMSO-d6, 400 MHz) δ 9.68 (d, 1H, J=6.9), 7.45 (m, 10H), 7.14 (d, 2H, J=8.0), 6.86 (d, 2H, J=8.0), 6.80 (d, 1H, J=5.6), 6.27 (d, 1H, J=5.5), 5.03 (s, 2H), 3.80 (m, 1H), 3.23 (d, br, 1H, J=9.0), 3.06 (d, 1H, J=9.5); low resolution MS (ESP+) m/e 458 (MH+).

Example 9

2-(2-Benzoyl-thiophen-3-yl-amino)-3-(4-benzyloxy-phenyl)-propionic acid

A solution of 300 mg (5.35 mmol) potassium hydroxide in 2 mL water was added to a stirred solution of 280 mg (0.59 mmol) of Intermediate 4 in 10 mL MeOH. The mixture was stirred for 2 h at 20° C. then 50 mL water, 50 mL brine and 3 mL acetic acid was added. The resulting emulsion was extracted with 20 mL methylene chloride three times. The organic phases were combined, dried with anhydrous magnesium sulfate, then concentrated under reduced pressure. The residue was purified by silica gel flash chromatography using $CH_2Cl_2$(neat), EtOAc/EtOH(9:1) and finally EtOH (neat) as eluents to provide 90 mg tile compound. 1H NMR (DMSO-d6, 400 MHz) δ 8.95 (d, 1H, J=7.7), 7.62 (m, 3H), 7.45 (m, 3H), 7.30 (m, 5H), 7.09 (d, 2H, J=8.4), 6.80 (d, 2H, J=8.2), 6.60 (d, 1H, J=5.5), 4.96 (s, 2H), 4.05 (m, 1H), 3.13

(d, br, 1H, J=11.8), 2.90 (dd, 1H, J=1.6, 3.4); low resolution MS (ESP+) m/e 458 (MH+).

Example 10

3-(4-Benzyloxy-phenyl)-2(S)-[(4-oxo-4H-chromene-3-carbonyl)-amino]-propionic acid methyl ester To a stirring solution of 360 mg (2 mmol) of chromone-3-carboxylic acid in 25 mL of $CH_2Cl_2$ at 0° C. were added several drops of DMF followed by 1 mL of 2M solution of oxalyl chloride in $CH_2Cl_2$. The resulting solution was stirred 3 h at rt and 643 mg (2 mmol) of O-benzyl-L-tyrosine methyl ester hydrochloride and 0.2 g (2.0 mmol) of triethylamine in 15 mL of $CH_2Cl_2$ were added and stirring continued overnight. Solvent was removed under reduced pressure. Product was purified by LCC on SiO2 (Hexane: EtOAc 13:7) providing 83 mg of title compound as a white solid: low resolution MS (ES+ (M+H), 458; RP-HPLC (Dynamax C-8 25 cm×4.1 mm; 50–90% $CH_3CN$ in $H_2O$ with 0.1% TFA buffer; 15 minutes; 2 mL/min): tr=10.44 min.

Example 11

2-(2-Benzoyl-phenylamino)-3-{4-[2-(methyl-pyridin-2-yl-amino)-ethoxy]-phenyl}-propionic acid A stirred solution of 300 mg (0.57 mmol) of Intermediate 21 300 mg (5.2 mmol) potassium hydroxide in 10 mL ethanol was refluxed for 30 min. The yellow solution was cooled to 20° C., 0.3 mL (5.2 mmol) acetic acid was added to the solution, then 30 mL water was added dropwise. The mixture was stirred at 20° C. for 30 min, the solid was filtered, and washed with 20 mL water three times to yield 180 mg of the title compound: low resolution MS (ESP+) m/e 496 (MH+); Anal. $(C_{30}H_{29}N_3O_4 \cdot \frac{1}{2}H_2O)$ Calcd. C, 71.41; H, 5.99; N, 8.33; Found C, 71.97; H, 5.98; N 8.33.

Example 12

2(S)-(2-benzoyl-phenylamino)-3-{4-[2-(methyl-pyridin-2-yl-amino)-ethoxy]- phenyl}-propionic acid A solution of 1.85 g (3.63 mmol) of Intermediate 26 in 30 mL of THF, 10 mL of water, and 10 mL of MeOH at 0° C. was treated with 5.45 mL (5.45 mmol, 1.5 equiv) of 1 M LiOH dropwise. After warming to 25° C. and stirring 2 h, the volatiles were removed under reduced pressure (<25° C.). The remaining aqueous layer was treated with EtOAc, acidified to pH 1 with 1 N HCl, and extracted with EtOAc. The combined organics were concentrated in vacuo and triturated with EtOAc. Filtration gave 1.24 g of the title compound as a yellow solid. An additional 0.50 g (97% total yield) of product was obtained upon concentration of the filtrate, trituration with EtOAc, and filtration: low resolution MS (Cl) m/e 518 (MNa+), 496 (MH+); Anal. $(C_{30}H_{29}N_3O_4 \cdot 0.8H_2O)$ C, 70.65; H, 6.05; N, 8.24 Found C, 70.74; H, 6.25; N, 7.92.

Example 13

2-(2-Benzoyl-phenylamino)-3-{4-[2-(methyl-pyridin-2-yl-amino)-ethoxy]-phenyl}-propionic acid ethyl ester A stirred solution of 100 mg (0.19 mmol) of Intermediate 21 and 100 mg (0.65 mmol) 1,8-diazabicyclo[5.4.0]undec-7-ene in 5 mL toluene was refluxed for 12 h. The solvent was removed under reduced pressure, and the residue was purified by silica gel flash chromatography using hexane(EtOAc (4:1) to yield 70 mg of the title compound: low resolution MS (ESP+) m/e 524 (MH+); TLC(hexane/EtOAc (4:1)): Rf=0.30).

Example 14

2-(1-Methyl-oxo-3-phenyl-propenylamino)-3{4-[2-(methyl-pyridin-2-yl-amino)-ethoxy]-phenyl}-propionic acid dicyclohexylamine salt A stirred suspension of 105 mg (0.33 mmol) of Intermediate 22, 58.5 mg (0.36 mmol) 1-benzoylacetone, 0.066 mL (0.33 mmol) dicyclohexylamine was refluxed for 24 h in 7 mL MeOH. 120 mL anhydrous ethanol was added to the solution, then the MeOH-ethanol mixture was distilled out from the flask at atmospheric pressure. When the remaining reaction volume was about 5 mL, the mixture was concentrated using reduced pressure. 3 mL anhydrous ether was then added to the residue at 0° C., and the resulting slurry was stirred at −5–0° C. for 30 min. The solid was filtered, and washed with 5 mL cold (−50° C.) ether three times to yield 105 mg of the title compound: low resolution MS (ESP+) m/e 460 (MH-DCA+), 182 (DCAH+); Anal. $(C_{39}H_{52}N_4O_4)$ Calcd. C, 73.09; H, 8.18; N, 8.74; Found C, 73.03; H, 8.13; N 8.72.

The enantiomers of the 2-(1-Methyl-3-oxo-3-phenyl-propenylamino)-3-{4-[2-(methyl-pyridin-2-yl-amino)-ethoxy]-phenyl}-propionic acid dicyclohexylamine salt were separated by chiral chromatography, (method: SFC, Column: Semi-Prep Chiralpak AD (25×2 cm), mobile phase: $CO_2$/Methanol (0.1% $Et_2NH$)(75:25), flow: 5.0 mL/min, pressure: 3000 psi, inj. volume: 50 mL, temp: 40° C., detector wavelength: 350 nM. injected amount: 15 mg) to obtain 4.7 mg (S)-2-(1-Methyl-3-oxo-3-phenyl-propenylamino)-3-{4-[2-(methyl-pyridin-2-yl-amino)-ethoxy]-phenyl}-propionic acid diethylamine salt (RT: 61.5 min.) and 5.5 mg (R)-2-(1-Methyl-3-oxo-3-phenyl-propenylamino)-3{4-[2-(methyl-pyridin-2-yl-amino)-ethoxy]-phenyl}-propionic acid diethylamine salt (RT:69.8 min.): 1H NMR (CDCl₃, 400 MHz) δ 11.76 (d, 1H, J=8.9), 9.46 (s(broad), 2H), 8.11 (d, 1H, J=4.2) 7.77 (d, 2H, J=7.8) 7.40 (m, 2H), 7.37 (d, 2H, J=7.5), 7.09 (d, 2H, J=8.3), 6.75 (d, 2H, J=8.2), 6.50 (m, 2H), 5.52 (s, 1H), 4.24 (m, 1H), 4.08 (t, 2H, J=5.3), 3.92 (t, 2H, J=5.4), 3.21 (m, 1H), 3.10 (s, 3H), 2.96 (m, 5H), 1.61 (s, 3H), 1.33 (m, 6H).

Example 15

3-{4-[2-(benzoxazol-2-yl-methyl-amino)-ethoxy]-phenyl}-2-(2-benzoyl-phenylamino)-propionic acid The title compound (24 mg) was prepared from 0.11 g (0.2 mmol) of Intermediate 10 and 0.11 g (2.1 mmol) of potassium hydroxide according to the method of Example 11 followed by purification by reverse phase HPLC using acetonitrile\water (15% to 80% gradient over 0.5 h) as eluent: low resolution MS (FAB) m/e 536 (MH+); high resolution MS (FAB) 536.283 (MH+), $C_{32}H_{29}N_3O_5$ requires 536.2185; reverse phase HPLC tr=21.2 min, to =1.77 min.

Example 16

3-{4-[2-(benzoxazol-2-yl-methyl-amino)-ethoxy]-phenyl}-2-(2-benzoyl-phenylamino)-propionic acid The title compound (209 mg) was prepared from 0.234 g (0.43 mmol) of Intermediate 10 according to the method of Example 12 followed by purification via trituration with Et$_2$O/hexanes: low resolution MS (Cl) m/e 558 (MNa+), 536 (MH+); Anal. (C$_{32}$H$_{29}$N$_3$O$_5$.1.1H$_2$O) Calcd. C, 69.20; H, 5.66; N, 7.57; Found C, 69.45; H, 5.82; N, 7.18; TLC (EtOAc/MeOH (9:1)): Rf=0.23.

Example 17

3-{4-[2-(Benzoxazol-2yl-methyl-amino)-ethoxy]-phenyl}-2(S)-(1-methyl-3-oxo-3-phenyl-propenylamino)-propionic acid dicyclohexylamine salt The title compound was prepared from 0.35 g (1.0 mmol) of Intermediate 8, 0.22 mL (1.1 mmol) dicyclohexylamine and 0.18 g (1.11 mmol) 1-benzoylacetone according to the method of Example 14: 1H NMR (DMSO-d6, 300 MHz) δ 11.47 (d, 1H, J=8.9) 7.84 (m, 2H), 7.45 (m, 4H), 7.31 (d, 1H, J=7.5), 7.18 (m, 3H), 7.03 (t, 1H, J=7.5), 6.86 (d, 2H, J=8.3), 5.60 (s, 1H), 4.25 (t, 2H, J=4.9), 4.07 (m, 1H), 3.91 (t, 2H, J=4.8), 3.26 (s, 3H), 3.14 (dd, 1H, J=4.3, 14.2), 3.01 (m, 2H), 2.81 (dd, 1H, J=8.8, 13.7), 1.99 (s, 3H), 1.80–1.05 (m, 20 H); low resolution MS (FAB+) m/e 500 (MH-DCA+), 182 (DCAH+).

Example 18

3-{4-[2-(Benzoxazol-2-yl-methyl-amino)-ethoxy]-phenyl}-2(S)-[3-(3-iodo-phenyl)-1-methyl-3-oxo-propenylamino]-propionic acid dicyclohexylamine salt The title compound (370 mg) was prepared from 0.35 g (1.0 mmol) of Intermediate 8, 0.22 mL (1.1 mmol) dicyclohexylamine and 0.29 g (1.0 mmol) 1-(3-iodo-phenyl)-butane-1,3-dione according to the method of Example 14: 1H NMR (DMSO-d6, 300 MHz) δ 11.48 (d, 1H, J=8.9) 7.84 (m, 2H), 7.42 (d, 1H, J=7.8), 7.20 (m, 4H), 7.03 (t, 1H, J=7.5), 6.86 (m, 3H), 5.59 (s, 1H), 4.25 (t, 2H, J=5.1), 4.08 (m, 1H), 3.92 (t, 2H, J=5.4), 3.27 (s, 3H), 3.15 (dd, 1H, J=3.8, 13.4), 3.02 (m, 2H), 2.82 (dd, 1H, J=8.8, 13.7), 2.00 (s, 3H), 1.80–1.10 (m, 20H); low resolution MS (FAB+) m/e 626 (MH-DCA+), 182 (DCAH+).

Example 19

3-{4-[2-(benzoxazol-2-yl-methyl-amino)-ethoxy]-phenyl}-2-(2-benzoyl-4-methyl-phenylamino)-propionic acid The title compound (5 mg) was prepared from 0.10 g (0.2 mmol) of Intermediate 11 according to the method of Example 11 followed by purification via reverse phase HPLC using acetonitrile/water (15% to 80% gradient over 0.5 h) as eluent: low resolution MS (FAB) m/e 550 (MH+); high resolution MS (FAB) m/e 550.2349 (MH+), C$_{33}$H$_{31}$N$_3$O$_5$ requires 550.2342.

Example 20

3-{4-[2-(benzoxazol-2-yl-methyl-amino)-ethoxy]-phenyl}-2-(2-benzoyl-4-chloro-phenylamino)-propionic acid Reaction was performed behind a blast shield. To a stirred solution of 0.20 g (0.5 mmol) of Intermediate 9 and 0.15 9 (0.6 mmol) of 2-amino-5-chloro benzophenone in 10 mL of toluene at 80° C. was added 2.4 mg (5.3 mmol) of rhodium (II) acetate dimer. Nitrogen was immediately released from the reaction. The solution was heated for 2 h and then cooled to RT. Solvent was removed in vacuo. The residue was purified by silica gel chromatography using EtOAc/hexane (gradient of 3:7 to 6:4) as gradient. The purified residue was then taken up in 10 mL ethanol and 0.10 g (2.0 mmol) of potassium hydroxide added. The resulting mixture was heated to 80° C. for 2 h. The solution was cooled to RT and diluted with 20 mL of water. Glacial acetic acid was then added dropwise to pH 5–6. A yellow precipitate was collected and washed with water and then washed with hexane. The solid was dried under vacuum at 40° C. for 0.5 h and further purified by silica gel chromatography using MeOHl-methylene chloride (1:9) as eluent. A solid was collected which was then recrystallized from methylene chloride (containing 1% MeOH) to yield 29.7 mg of the title compound: low resolution MS (FAB) m/e 570 (MH+); Anal. calcd. for C$_{32}$H$_{28}$N$_3$O$_5$Cl, C, 67.43%, H, 4.95%, N, 7.37%. Found C, 67.36%, H, 4.95%, N, 7.35%.

Example 21

3-[4-(1-Benzoxazol-2-yl-pyrrolidin-3-yloxy)-phenyl]-2-(2-benzoyl-phenylamino)-propionic acid To a stirring solution of 130 mg (0.23 mmol) of Intermediate 34 in 3 mL of dioxane and 3 mL H$_2$O was added 10 mg (0.23 mmol, 1.0 equiv.) of lithium hydroxide. The resulting solution was stirred 12 h at RT then acidified to pH2 The reaction mixture was poured into 50 mL of EtOAc and washed with brine (1×10 mL). The organic layer was separated, dried (MgSO$_4$), and the solvents removed in vacuo. Purification by silica gel flash column chromatography using DCM/MeOH/HOAc 9/1/0.1 as eluent afforded 127 mg of the title compound: low resolution MS (ESP) m/e 548.0 (MH+). RP-HPLC (Vydac C-18, 25 cm×4.6 mm; 10–90% CH3CN in H20 with 0.1% TFA buffer; 25 minutes; 1 mL/min); tr=13.46 min (t0=3 min).

Example 22

3-[4-(1-benzoxazol-2-yl)-pyrrolidin-2R-yl-methoxy)-phenyl]-2-(2-benzoyl-phenylamino)-propionic acid The title compound (150 mg) was prepared from 0.17 g (0.30 mmol) of Intermediate 31 according to the method of Example 12: low resolution MS (ES) m/e 562 (M+); TLC (EtOAc/MeOH (9:1)): Rf=0.34.

Example 23

3-[4-(1-benzoxazol-2-yl)-pyrrolidin-2S-yl-methoxy)-phenyl]-2-(2-benzoyl-phenylamino)-propionic acid The title compound (2.14 g) was prepared from 2.26 g (3.93 mmol) of Intermediate according to the method of Example 12 followed by purification via trituration with hexanes/Et$_2$O: low resolution MS (ES) m/e 562 (M+); Anal. (C$_{34}$H$_{31}$N$_3$O$_5$.0.9H$_2$O) Calcd. C, 70.67; H, 5.72; N, 7.27; Found C, 70.65; H, 6.01; N, 7.28.

Example 24

3-{4-[2-(Benzoxazol-2-yl-methyl-amino)-ethoxy]-phenyl}-2-(2-cyclohexanecarbonyl-phenylamino)-propionic acid The title compound (44 mg) was prepared from 61 mg (0.11 mmol) of Intermediate 12 according to the method of Example 21 followed by purification viasilica gel flash column chromatography using DCM/MeOH 91/1/as eluent: low resolution MS (API) m/e 542.3 (MH+); RP-HPLC

Example 25

3-{4-[2-Benzoxazol-2-yl-methyl-amino)-ethoxy]-phenyl}-2-(2-benzoyl-thiophen-3-ylamino)-propionic acid The title compound (44 mg) was prepared from 113 mg (0.20 mmol) of Intermediate 13 according to the method of Example 21 followed by purification via silica gel flash column chromatography using DCM/MeOH 19/1/as eluent: low resolution MS (API) m/e 542.2 (MH+). RP-HPLC (Vydac C-18, 25 cm×4.6 mm; 10–90% $CH_3CN$ in $H_2O$ with 0.1% TFA buffer; 25 minutes; 1 mL/min); tr=12.60 min (t0=3 min).

Example 26

3-{4-[2-(Benzoxazol-2-yl-methyl-amino)-ethoxy]-phenyl}-2-benzyl-propionic acid trifluoroacetate To a stirring solution of 90.8 mg (0.2042 mmol) of Intermediate 15 in 2.0 mL of a 2:1 mixture of THF:$H_2O$ at rt was added 9.8 mg (0.4085 mmol, 2.0 equiv) of LiOH. The resulting solution was stirred at 60° C. for 19 h, cooled, then extracted with EtOAc. The aqueous layer was acidified with 1.0 N HCl and extracted with EtOAc. The organic layers were dried ($MgSO_4$), and the solvents removed in vacuo. Purification by preparatory reverse phase HPLC using 15–80% $CH_3CN/H_2O$ with 1% TFA buffer as eluent afforded 87.3 mg of the title compound as a white amorphous solid: low resolution MS (ES) m/e 429 (M–H); high resolution MS (FAB) m/e for $C_{26}H_{27}N_2O_4$: calcd. 431.1938; found 431.1965 (MH+).

Example 27

3-{4-[2-(Benzoxazol-2-yl-methyl-amino)-ethoxy]-phenyl}-2-(2-bromo-benzyl)-propionic acid trifluoroacetate The title compound (31 mg) was prepared from 51.9 mg (0.0991 mmol) of Intermediate 16 according to the method of Example 26 followed by purification via preparatory reverse phase HPLC using 15–80% $CH_3CN/H_2O$ with 1% TFA buffer as eluent: low resolution MS (ES) m/e 507 (M–H); high resolution MS (FAB) m/e for $C_{26}H_{26}BrN_2O_4$: calcd. 509.1075; found 509.1085 (MH+).

Example 28

3-{4-[2-(Benzoxazol-2-yl-methyl-amino)-ethoxy]-phenyl}-2(S)-[(4-oxo-4H-chromene-3-carbonyl)-amino]-propionic acid To a stirring suspension of 120 mg of 60% NaH in 10 mL of DMF at 0° C. was added 990 mg (3.0 mmol) of N-carbobenzoxy-L-tyrosine methyl ester in 10 mL of DMF. The resulting mixture was stirred until it became clear. N-2-[(N-methyl aminoethyl-1-methylsulfonate)-1,3-benzoxazole 810 mg (3.0 mmol) in 10 mL of DMF was then added and mixture stirred overnight at rt. Solvent was removed under reduced pressure, residue dissolved in EtOAc and washed with 1N HCl, sat $NaHCO_3$aq. and water. EtOAc was evaporated providing 300 mg of yellow oil (MS (ES+)(M+H=504)). Oil was re dissolved in EtOAc 50 mg of 10% Pd/C were added and reaction mixture was hydrogenated under atm. pressure overnight. Catalyst was filtered off and solvent evaporated providing 190 mg of amino ester as yellow oil which was used without further purification. To a stirring solution of 90 mg (0.5 mmol) of chromone-3-carboxylic acid in 15 mL of $CH_2Cl_2$ at 0° C. were added several drops of DMF followed by 0.25 mL of 2M solution of oxalyl chloride in $CH_2Cl_2$. The resulting solution was stirred 3 h at rt and 190 mg (0.5 mmol) of previously prepared amino ester and 50 mg (0.5 mmol) of triethylamine in 15 mL of $CH_2Cl_2$ were added and stirring continued overnight. Solvent was removed under reduced pressure and residue dissolved in mixture of THF and water and 0.5 mL of 1n NaOH were added and mixture was stirred for 3 hr. 30 mg (0.5 mmol) of acetic acid were added and solvent removed under reduced pressure. Crude material was purified by RP Prep. HPLC affording 11 mg of title compound: low resolution MS(ES+)(M+H+), 528; RP-HPLC (Dynamax C-8 25 cm×4.1 mm; 50–90% $CH_3CN$ in $H_2O$ with 0.1% TFA buffer; 15 minutes; 2 mL/min): tr=3.20 min.

Example 29

2(S)-(2-Benzoyl-phenylamino)-3-{4-[2-(5-methyl-2-phenyl-oxazol-4-yl)ethoxy]-phenyl}-propionic acid A solution of 0.21 g (0.37 mmol) of Intermediate 35 in 20 mL of 6:4 THF:water was treated with 13 mg (0.56 mmol, 1.5 equiv) of LiOH. After stirring at RT for 3 h, TLC ($SiO_2$, 7:3 hexane:EtOAc) indicated a significant amount of starting material at Rf=0.51 and a major new component at the origin. The solution was treated with an additional 6 mg of LiOH and stirred for an additional 2 h at which point TLC indicated no remaining starting material. The solution was neutralized by addition of 1 mL of 1N aqueous HCl and subjected to rotary evaporation to remove THF. A yellow mixture resulted which was extracted with $CHCl_3$ (3×20 mL). The combined extracts were washed with water (3×50 mL), dried over anhydrous $MgSO_4$, and concentrated in vacuo to afford 0.20 g (99%) of the title compound as a yellow foam: mp 85–90° C.; 1H-NMR (DMSO-d6, 200 MHz) δ 8.66 (d, 1H, J=7.8), 7.91 (m, 2H), 7.64–7.33 (m, 10H), 7.13 (d, 2H, J=8.3), 6.82 (m, 3H), 6.62 (t, 1H, J=7.5), 4.54 (m, 1H), 4.15 (t, 2H, J=6.5), 3.10 (m, 2H), 2.90 (t, 2H, J=6.5), 2.34 (s, 3H); low resolution MS (ES) m/e 547 (MH+); Anal. ($C_{34}H_{30}N_2O_5$ 0.3 $H_2O$) Calcd. C, 73.98; H, 5.59; N, 5.07; Found C, 73.91; H, 5.62; N, 5.00; TLC ($CH_2Cl_2$/MeOH(95:5)): Rf=0.49.

Example 30

2-(2-Benzoyl-phenylamino)-3-{4-[2-(4-chlorophenyl)-thiazol-4ylmethoxy]-phenyl}-propionic acid The title compound (154 mg) was prepared from 200 mg (0.34 mmol) of Intermediate 36 according to the method of Example 12 followed by purification via trituration in acetonitrile/chloroform 1/1: low resolution MS (FAB)m/e 572 (MH++2), 571 (MH++1), 570 (MH+), 569 (M+); Anal. ($C_{32}H_{25}ClN_2O_4S$) Calcd. C, 67.54; H, 4.43; N, 4.92, Found C, 67.36; H, 4.51; N, 4.90.

Example 31

3-[4-(2-Benzoimidazol-1-yl-ethoxy)-phenyl]-2-(2-benzoyl-phenylamino)-propionic acid The title compound (58 mg) was prepared from 90 mg (0.17 mmol) of Intermediate 40 according to the method of

Example 32

2(S)-(2-benzoyl-phenylamino)-3-{4-[2-(5-methyl-2-(4-methoxy)-phenyl-oxazol-4-yl)-ethoxy]-phenyl}-propionic acid To a stirring solution of 190 mg (0.32 mmol) of Intermediate 44 in 7 mL of THF/MeOH/H$_2$O (6:0.1:1) at RT was added 0.50 mL (0.50 mmol, 1.6 equiv) of a 1.0 M solution of LiOH in H$_2$O. The resulting solution was stirred 18 h at RT, then was poured into 50 mL of EtOAc and extracted with 1 N HCl (2×50 mL). The organic layer was separated, dried (MgSO$_4$), and the solvents removed in vacuo. Purification of the yellow solid by trituration in EtOAc/diethyl ether 1:1 followed by vacuum filtration and drying under vacuum afforded 96 mg of the title compound as a yellow amorphous solid: low resolution MS (FAB)m/e 578 (MH$^+$), 577 (M$^+$); RP-HPLC (Dynamax C-8 25 cm×4.1 mm; 30–80% CH$_3$CN in H$_2$O with 0.1% TFA buffer; 30 minutes; 1 mL/min): t$_r$=25.59 min.

Example 33

2(S)-(2-benzoyl-phenylamino)-3-{4-[2-(5-methyl-2-(4-fluoro)-phenyl-oxazol-4-yl)-ethoxy]-phenyl}-propionic acid The title compound (205 mg) was prepared from 280 mg (0.48 mmol) of Intermediate 47 and 0.73 mL (0.73 mmol, 1.5 equiv) of a 1.0 M solution of LiOH in H$_2$O according to the method of example 32: low resolution MS (FAB)m/e 566 (MH$^+$), 565 (M$^+$); Anal. (C$_{34}$H$_{29}$FN$_2$O$_5$) Calcd. C, 72.33; H, 5.18; N, 4.96, Found C, 72.24; H, 5.23; N, 4.89.

Example 34

2(S)-(2-benzoyl-phenylamino)-3-{4-[2-(5-methyl-2-(5-methyl-thien-2-yl)-oxazol-4-yl)-ethoxy]-phenyl}-propionic acid The title compound (297 mg) was prepared from 440 mg (0.76 mmol) of Intermediate 111 and 1.10 mL (1.10 mmol, 1.5 equiv) of a 1.0 M solution of LiOH in H$_2$O according to the method of Example 32: low resolution MS (FAB)m/e 568 (MH$^+$), 567 (M$^+$); Anal. (C$_{33}$H$_{30}$N$_2$O$_5$S) Calcd. C, 69.95; H, 5.34; N, 4.94, Found C, 69.31; H, 5.37; N, 4.91.

Example 35

2(S)-(2-benzoyl-phenylamino)-3-{4-[2-(5-methyl-1-phenyl-1H-pyrazol-3-yl)-ethoxy]-phenyl}-propionic acid The title compound (74 mg) was prepared from 100 mg (0.18 mmol) of Intermediate 49 and 0.27 mL (0.27 mmol, 1.5 equiv) of a 1.0 M solution of LiOH in H$_2$O according to the method of Example 32: low resolution MS (FAB)m/e 547 (MH$^+$), 546 (M$^+$); t$_r$=14.73 min.; Anal. (C$_{34}$H$_{31}$N$_3$O$_4$) Calcd. C, 74.84; H, 5.73; N, 7.70, Found C, 74.89; H, 5.79; N, 7.62.

Example 36

2(S)-(2-benzoyl-phenylamino)-3-{4-[2-(5-methyl-2-piperidin-1-yl-oxazol-4-yl)-ethoxy]-phenyl}-propionic acid The title compound (47 mg) was prepared from 270 mg (0.48 mmol) of Intermediate 52 and 0.70 mL (0.70 mmol, 1.5 equiv) of a 1.0 M solution of LiOH in H$_2$O according to the method of Example 32: low resolution MS (FAB)m/e 555 (MH$^+$), 554 (M$^+$); RP-HPLC (Dynamax C-8 25 cm×4.1 mm; 30–80% CH$_3$CN in H$_2$O with 0.1% TFA buffer; 30 minutes; 1 mL/min): t$_r$=18.54 min.

Example 37

2(S)-(2-benzoyl-phenylamino)-3-{4-[2-(5-methyl-2-morpholin-4-yl-thiazol-4-yl)-ethoxy]-phenyl}-propionic acid The title compound (456 mg) was prepared from 810 mg (1.38 mmol) of Intermediate 56 and 2.00 mL (2.00 mmol, 1.5 equiv) of a 1.0 M solution of LiOH in H$_2$O according to the method of Example 32. Purification of the yellow oil by silica gel flash column chromatography using chloroform/MeOH 12/1 as eluent followed by trituration in EtOAc/diethyl ether 1:1 provided a yellow amorphous solid: mp 148–151° C.; low resolution MS (FAB)m/e 573 (MH$^+$), 572 (M$^+$); Anal. (C$_{32}$H$_{33}$N$_3$O$_5$S.HCl) Calcd. C, 63.20; H, 5.64; N, 6.91, Found C, 63.68; H, 5.70; N, 6.73.

Example 38

2(S)-(2-benzoyl-phenylamino)-3-{4-[2-(5-methyl-2-(4-pyridyl)-thiazol-4-yl)-ethoxy]-phenyl}-propionic acid The title compound (102 mg) was prepared from 165 mg (0.29 mmol) of Intermediate 59 and 0.43 mL (0.43 mmol, 1.5 equiv) of a 1.0 M solution of LiOH in H$_2$O according to the method of Example 32. Purification by silica gel flash column chromatography using chloroform/MeOH 9/1 as eluent followed by trituration in EtOAc/diethyl ether 1:1 afforded a yellow amorphous solid: mp 155–158° C.; low resolution MS (FAB)m/e 564 (M$^+$); Anal. (C$_{33}$H$_{29}$N$_3$O$_4$S.2HCl) Calcd. C, 62.16; H, 5.06; N, 6.59, Found C, 62.41; H, 4.82; N, 6.83.

Example 39

2(S)-(2-benzoyl-phenylamino)-3-{4-[2-(2-dimethylamino-5-methyl-thiazol-4-yl)-ethoxy]-phenyl}-propionic acid To a stirring solution of 150 mg (0.27 mmol) of Intermediate 62 in 7 mL of THF/MeOH/H$_2$O (6:0.1:1) at RT was added 0.42 mL (0.42 mmol, 1.5 equiv) of a 1.0 M solution of LiOH in H$_2$O. The resulting solution was stirred 5 h at RT, then the solvent was removed in vacuo. The residue was redissolved in THF and acidified with 0.022 mL (0.42 mmol, 1.5 equiv) of concentrated sulfuric acid. Purification of the yellow oil by silica gel flash column chromatography using EtOAc/MeOH 1/1 with 1% ammonium hydroxide as eluent afforded 39 mg of the title compound as a yellow amorphous solid: low resolution MS (FAB)m/e 531 (MH$^+$), 530 (M$^+$); Anal. (C$_{30}$H$_{31}$N$_3$O$_4$S.H$_2$O) Calcd. C, 65.79; H, 6.07; N, 7.67, Found C, 65.74; H, 5.87; N, 7.54.

Example 40

2(S)-(2-benzoyl-phenylamino)-3-{4-[2-(5-methyl-2-(5-methyl-isoxazol-3-yl)-thiazol-4-yl)-ethoxy]-phenyl}-propionic acid The title compound (220 mg) was prepared from 450 mg (0.77 mmol) of Intermediate 66 and 1.20 mL (1.2 mmol, 1.5 equiv) of a 1.0 M solution of LiOH in H$_2$O according to the method of Example 32. Purification by silica gel flash column chromatography using chloroform/MeOH 9/1 as eluent followed by trituration with diethyl ether afforded a yellow amorphous solid: low resolution MS (FAB)m/e 568 (MH$^+$); Anal. ($C_{32}H_{29}N_3O_5S.H_2O$) Calcd. C, 65.62; H, 5.34; N, 7.17, Found C, 65.64; H, 5.13; N, 7.13.

Example 41

2(S)-(2-benzoyl-phenylamino)-3-(4-{2-[5-methyl-2-(4-methyl[1,2,3]thiadiazol-5-yl)-thiazol-4-yl]ethoxy}-phenyl)-propionic acid The title compound (120 mg) was prepared from 230 mg (0.38 mmol) of Intermediate 69 and 0.575 mL (0.58 mmol, 1.5 equiv) of a 1.0 M solution of LiOH in $H_2O$ according to the method of Example 32. Purification by silica gel flash column chromatography using chloroform/MeOH 9/1 as eluent afforded a yellow amorphous solid: low resolution MS (FAB)m/e 585 (MH$^+$); RP-HPLC (Dynamax C-8 25 cm×4.1 mm; 50–100% $CH_3CN$ in $H_2O$ with 0.1% TFA buffer; 30 minutes; 1 mL/min): $t_r$=16.52 min.

Example 42

2(S)-(2-benzoyl-phenylamino)-3-(4-{2-[5-methyl-2-(4-methyl-piperazin-1-yl)-thiazol-4-yl]-ethoxy}-phenyl)-propionic acid A suspension of 1.93 g (7.40 mmol, 1.10 equiv) of triphenylphosphine, 2.51 g (6.70 mmol) of Intermediate 23, and 2.20 g (6.70 mmol) of Intermediate 71 in 40 mL of dry toluene was heated to 95° C. for 15 min to effect dissolution of Intermediate 23 to provide a clear yellow solution. To this solution was added 1.23 g (7.04 mmol, 1.05 equiv) of diethyl azodicarboxylate dropwise over 10 min. The reaction was then allowed to cool to RT and stirred 16 h. The toluene was removed in vacuo, and the residue was purified by silica gel flash column chromatography using EtOAc/MeOH 10/1 with 1% ammonium hydroxide as eluent to afford 3.06 g of the title compound as a yellow oil. Approximately 130 mg of the material was dissolved in diethyl ether and the pH was adjusted to 1.0 by the addition of a 1.0 M solution of HCl in diethyl ether. The resulting yellow precipitate was filtered and dried under vacuum to afford 100 mg of the HCl salt: low resolution MS (FAB)m/e 599 (MH$^+$); RP-HPLC (Dynamax C-8 25 cm×4.1 mm; 30–80% $CH_3CN$ in $H_2O$ with 0.1% TFA buffer; 30 minutes; 1 mL/min): $t_r$=17.79 min.

Example 43

2(S)-(2-benzoyl-phenylamino)-3-(4-{2-[2-(3-dimethylamino-propylamino)-5-methyl-thiazol-4-yl]-ethoxy}-phenyl)-propionic acid The title compound (522 mg) was prepared from 695 mg (1.15 mmol) of Intermediate 74 and 1.75 mL (1.75 mmol, 1.5 equiv) of a 1.0 M solution of LiOH in $H_2O$ according to the method of Example 32. Purification by silica gel flash column chromatography using MeOH as eluent followed by trituration with EtOAc afforded a yellow amorphous solid: low resolution MS (FAB)m/e 587 (MH$^+$); Anal. ($C_{33}H_{38}N_4O_4S.HCl.H_2O$) Calcd. C, 61.81; H, 6.44; N, 8.73, Found C, 61.93; H, 6.20; N, 8.77.

Example 44

2(S)-(2-benzoyl-phenylamino)-3-(4-{2-[2-(2-methoxy-ethylamino)-5-methyl-thiazol-4-yl]-ethoxy}-phenyl)-propionic acid The title compound (473 mg) was prepared from 907 mg (1.58 mmol) of Intermediate 76 and 12.40 mL (2.40 mmol, 1.5 equiv) of a 1.0 M solution of LiOH in $H_2O$ according to the method of Example 32. Purification by silica gel flash column chromatography using chloroform/MeOH 9/1 as eluent afforded a yellow amorphous solid: low resolution MS (FAB)m/e 560 (M$^+$); Anal. ($C_{31}H_{33}N_3O_5S.HCl.H_2O$) Calcd. C, 60.63; H, 5.91; N, 6.84, Found C, 60.61; H, 5.55; N, 6.83.

Example 45

2-(1-Carboxy-2-{4-[2-(5-methyl-2-phenyl-thiazol-4-yl)-ethoxy]-phenyl}-ethylamino)-benzoic acid methyl ester The title compound (290 mg) was prepared from 400 mg (0.75 mmol) of Intermediate 150 and 1.50 mL (1.50 mmol, 2.0 equiv) of a 1.0 M solution of LiOH in $H_2O$ according to the method of Example 32. Purification by silica gel flash column chromatography using chloroform/MeOH 9/1 as eluent afforded a white solid: low resolution MS (FAB)m/e 517 (M$^+$); Anal. ($C_{29}H_{28}N_2O_5S$ .$H_2O$) Calcd. C, 65.15; H, 5.65; N, 5.24, Found C, 65.60; H, 5.35; N, 5.23.

Example 46

2-(1-Carboxy-2-{4-[2-(4-clhorophenylsulfanyl)-ethoxy]-phenyl}-ethylamino)-benzoic acid methyl ester The title compound (40 mg) was prepared from 118 mg (0.24 mmol) of Intermediate 151 and 0.47 mL (0.47 mmol, 2.0 equiv) of a 1.0 M solution of LiOH in $H_2O$ according to the method of Example 32. Purification by silica gel flash column chromatography using chloroform/MeOH 9/1 as eluent afforded a light tan solid: low resolution MS (FAB) m/e 486 (M$^+$); RP-HPLC (Dynamax C-8 25 cm×4.1 mm; 50–100% $CH_3CN$ in $H_2O$ with 0.1% TFA buffer; 30 minutes; 1 mL/min): $t_r$=16.81 min.

Example 47

2-(1-Carboxy-2-{4-[1-(4-nitro)-phenyl-pyrrolidin-2-ylmethoxy]-phenyl}-ethylamino)-benzoic acid methyl ester A suspension of 95 mg (0.36 mmol, 1.10 equiv) of triphenylphosphine, 100 mg (0.30 mmol) of Intermediate 127, and 80 mg (0.36 mmol) of (S)-(–)-1-(4-nitrophenyl)-2-pyrrolidineMeOH in 5 mL of dry toluene was heated to 80° C. for 15 min to effect dissolution of Intermediate 127 to provide a clear yellow solution. To this solution was added 68 mg (0.33 mmol, 1.2 equiv) of diisopropyl azodicarboxylate dropwise over 5 min. The reaction was then allowed to cool to RT and stirred 16 h. The toluene was removed in vacuo, and then the residue was stirred vigorously for 1 h in 10 mL of 1:1 diethyl ether/1 N LiOH biphasic solution to effect selective removal of residual Intermediate 127. The layers were separated and the organic layer washed with $H_2O$, dried (MgSO$_4$), and solvent removed in vacuo. The material was purified by silica gel flash column chromatography using hexane/EtOAc 3/1 as eluent to afford 94 mg of the title compound as a yellow solid. This material was dissolved in 5 mL of THF/MeOH/$H_2O$ (4:0.1:1) at RT and 0.35 mL (0.35 mmol, 2.0 equiv) of a 1.0 M solution of LiOH in $H_2O$ was added. The resulting solution was stirred 4 h at RT, then was poured into 20 mL of EtOAc and extracted with 1 N HCl (2×10 mL). The organic layer was separated, dried (MgSO$_4$), and the solvents removed in vacuo. Purification of the material by silica gel flash column chromatography using chloroform/MeOH 9/1 as eluent afforded 30 mg of the title compound as a yellow solid: low resolution MS (FAB)m/e 520 (MH$^+$); Anal. ($C_{28}H_{29}N_3O_7.H_2O$) Calcd. C, 62.56; H, 5.81; N, 7.82, Found C, 62.18; H, 5.50; N, 7.86.

Example 48

3-{4-[2-(Benzoxazol-2-yl-methyl-amino)-ethoxy]-phenyl}-2-(2-cyclopentanecarbonyl-phenylamino)-propionic acid The title compound (66 mg) was prepared from 0.55 g (1.07 mmol) of Intermediate 77 and 67.5 mg (1.61 mmol, 1.5 equiv.) of lithium hydroxide according to the method of Example 32 followed by purification via silica gel flash column chromatography using DCM/MeOH 98/2 as eluent: low resolution MS (ES) m/e 526.2 (MH$^-$); RP-HPLC (Vydac C-18, 25 cm×4.6 mm; 30–80% $CH_3CN$ in $H_2O$ with 0.1% TFA buffer; 25 minutes; 1 mL/min); $t_r$=21.29 min ($t_0$=3 min).

Example 49

3-{4-[2-(Benzoxazol-2-yl-methyl-amino)-ethoxy]-phenyl}-2-(2-cycloheptanecarbonyl-phenylamino)-propionic acid The title compound (39 mg) was prepared from 0.13 g (0.23 mmol) of Intermediate 78 and 14.5 mg (0.35 mmol, 1.5 equiv.) of lithium hydroxide according to the method of Example 32 followed by purification via silica gel flash column chromatography using DCM/MeOH 98/2 to 90/10 as eluent: low resolution MS (ES) m/e 554.1 (MH$^-$); RP-HPLC (Vydac C-18, 25 cm×4.6 mm; 30–80% $CH_3CN$ in $H_2O$ with 0.1% TFA buffer; 25 minutes; 1 mL/min); $t_r$=24.86 min ($t_0$=3 min).

Example 50

3-{4-[2-(Benzoxazol-2-yl-methyl-amino)-ethoxy]-phenyl}-2-(2-cyclohexanecarbonyl-5-fluoro-phenylamino)-propionic acid The title compound (139 mg) was prepared from 0.39 g (0.68 mmol) of Intermediate 79 and 34.4 mg (0.82 mmol, 1.2 equiv.) of lithium hydroxide according to the method of Example 32 followed by purification via silica gel flash column chromatography using DCM/MeOH 98/2 to 95/5 as eluent: low resolution MS (ES) m/e 558.0 (MH$^-$); RP-HPLC (Vydac C-18, 25 cm×4.6 mm; 30–80% $CH_3CN$ in $H_2O$ with 0.1% TFA buffer; 25 minutes; 1 mL/min); $t_r$=22.62 min ($t_0$=3 min).

Example 51

3-{4-[2-(Benzoxazol-2-yl-methyl-amino)-ethoxy]-phenyl}-2-(4-cyclohexanecarbonyl-2-methyl-2H-pyrazol-3-ylamino)-propionic acid The title compound (68 mg) was prepared from 0.175 g (0.31 mmol) of Intermediate 80 and 16 mg (0.37 mmol, 1.2 equiv.) of lithium hydroxide according to the method of Example 32 followed by purification via silica gel flash column chromatography using DCM/MeOH 98/2 to 90/10/ 0.1 DCM/MeOH/HOAc as eluent: low resolution MS (ES) m/e 544.1 (MH$^-$); RP-HPLC (Vydac C-18, 25 cm×4.6 mm; 30–80% $CH_3CN$ in $H_2O$ with 0.1% TFA buffer; 25 minutes; 1 mL/min); $t_r$=14.66 min ($t_0$=3 min).

Example 52

3-{4-[2-(Benzoxazol-2-yl-methyl-amino)-ethoxy]-phenyl}-2-(3-benzoyl-thiophene-2-ylamino)-propionic acid The title compound (77 mg) was prepared from 0.145 g (0.26 mmol) of Intermediate 81 and 14 mg (0.34 mmol, 1.3 equiv.) of lithium hydroxide according to the method of Example 32 followed by purification via silica gel flash column chromatography using DCM/MeOH 95/5 to 90/10 as eluent: low resolution MS (ES) m/e 539.9 (MH$^-$); RP-HPLC (Vydac C-18, 25 cm×4.6 mm; 30–80% $CH_3CN$ in $H_2O$ with 0.1% TFA buffer; 25 minutes; 1 mL/min); $t_r$=18.16 min ($t_0$=3 min).

Example 53

2-(2-Cyclohexanecarbonyl-phenylamino)-3-{4-[2-(5-methyl-2-phenyl-oxazol-4-yl)-ethoxy]-phenyl}-propionic acid The title compound (750 mg) was prepared from 1.08 g (1.90 mmol) of enantiomer 1 of Intermediate 83 and 120 mg (2.86 mmol, 1.5 equiv.) of lithium hydroxide according to the method of Example 32 followed by purification via silica gel flash column chromatography using DCM/MeOH 95/5 as eluent: low resolution MS (ES) m/e 551.2 (MH$^-$); RP-HPLC (Vydac C-18, 25 cm×4.6 mm; 30–80% $CH_3CN$ in $H_2O$ with 0.1% TFA buffer; 25 minutes; 1 mL/min); $t_r$=18.22 min ($t_0$=3 min). Daicel Chiral OD-H (4.6×250 mm, 5 m; 0.7 mL/min; inj volume 3 mL, UV 230 nM; 60/40 IPA/Hexane; 30 min); $t_r$=7.44 min, 99.99% ee.

Example 54

2-(2-Cyclohexanecarbonyl-phenylamino)-3-{4-[2-(5-methyl-2-phenyl-oxazol-4-yl)-ethoxy]-phenyl}-propionic acid The title compound (78 mg) was prepared from 220 mg (0.39 mmol) of enantiomer 2 of Intermediate 83 and 24 mg (0.58 mmol, 1.5 equiv.) of lithium hydroxide according to the method of Example 32 followed by purification via silica gel flash column chromatography using DCM/MeOH 95/5 as eluent: MS,HPLC identical to Example 53. Daicel Chiral OD-H (4.6×250 mm, 5 m; 0.7 mL/min; inj volume 3 mL, UV 230 nM; 60/40 IPA/Hexane; 30 min); $t_r$=11.67 min, 99.3% ee.

Example 55

3-[4-(1-Benzoxazol-2-yl-pyrrolidin-3-yloxy)-phenyl]-2-(2-benzoyl-phenylamino)-propionic acid The title compound (115 mg) was prepared from 200 mg (0.36 mmol) of 3-[4-(1-Benzoxazol-2-yl-pyrrolidin-3-yloxy)-phenyl]-2-(2-benzoyl-phenylamino)-propionic acid methyl ester and 18 mg (0.43 mmol, 1.2 equiv.) of lithium hydroxide according to the method of Example 32 followed by purification via silica gel flash column chromatography using DCM/MeOH 90/10 as eluent: low resolution MS (ES) m/e 546.0 (MH$^-$); RP-HPLC (Vydac C-18, 25 cm×4.6 mm; 30–80% $CH_3CN$ in $H_2O$ with 0.1% TFA buffer; 25 minutes; 1 mL/min); $t_r$=17.92 min ($t_0$=3 min). Daicel Chiral OD-H (4.6×250 mm, 5 m; 0.7 mL/min; inj volume 3 mL, UV 230 nM; 40/60/0.1 IPA/Hexane/TEA; 30 min); $t_r$=6.8 min and 10.0 min.

Example 56

3-{4-[2-(5-Methyl-2-phenyl-oxazol-4-yl)-ethoxy]-phenyl}-2(S)-[2-(pyridine-4-carbonyl)-phenylamino]-propionic acid The title compound (815 mg) was prepared from 1.71 g (3.05 mmol) of Intermediate 87 and 192 mg (4.57 mmol, 1.5 equiv.) of lithium hydroxide according to the method of Example 32 followed by trituration in DCM: low resolution MS (ES) m/e 546 (MH⁻); RP-HPLC (Vydac C-18, 25 cm×4.6 mm; 30–80% CH$_3$CN in H$_2$O with 0.1% TFA buffer; 25 minutes; 1 mL/min); t$_r$=16.35 min (t$_0$=3 min). Daicel Chiral OD-H (4.6×250 mm, 5 m; 0.7 mL/min; inj volume 3 mL, UV 230 nM; 40/60/0.1 IPA/Hexane/TEA; 30 min); t$_r$=9.21 min, 96% ee.

Example 57

3-{4-[2-(5-methyl-2-phenyl-oxazol-4-yl)-ethoxy]-phenyl}-2(S)-[2-(pyridineN-oxide-4-carbonyl)-phenylamino]-propionic acid The title compound (52 mg) was prepared from 70 mg (0.12 mmol) of Intermediate 88 and 10 mg (0.24 mmol, 2 equiv.) of lithium hydroxide according to the method of Example 32 followed by purification via silica gel flash column chromatography using DCM/MeOH 90/10 as eluent: $^1$H NMR (DMSO-d6 400 MHz) δ 8.69 (d,1H, J=7.2), 8.26 (d, 2H, J=7.1), 7.85 (m, 3H), 7.46 (m, 4H), 7.38 (m, 2H), 7.05 (d, 2H, J=8.4), 6.74 (m, 2H), 6.49 (m, 1H), 4.10 (m, 2H), 3.15 (m, 2H), 2.96 (m, 1H), 2.85 (m, 2H), 2.49 (s, 3H); low resolution MS (ES) m/e 562 (MH⁻); RP-HPLC (Vydac C-18, 25 cm×4.6 mm; 30–80% CH$_3$CN in H$_2$O with 0.1% TFA buffer; 25 minutes; 1 mL/min); t$_r$=15.92 min (t$_0$=3 min).

Example 58

3-{4-[2-(5-Methyl-2-phenyl-oxazol-4-yl)-ethoxy]-phenyl}-2(S)-[2-(pyridine-3-carbonyl)-phenylamino]-propionic acid The title compound (506 mg) was prepared from 0.54 g (0.96 mmol) of Intermediate 89 and 122 mg (2.88 mmol, 3.0 equiv.) of lithium hydroxide according to the method of Example 32 followed by purification via silica gel flash column chromatography using DCM/MeOH 90/10 as eluent: low resolution MS (ES) m/e 546 (MH⁻); RP-HPLC (Vydac C-18, 25 cm×4.6 mm; 30–80% CH$_3$CN in H$_2$O with 0.1% TFA buffer; 25 minutes; 1 mL/min); t$_r$=17.31 min (t$_0$=3 min). Daicel Chiral OD-H (4.6×250 mm, 5 m; 0.7 mL/min; inj volume 3 mL, UV 230 nM; 40/60/0.1 IPA/Hexane/TEA; 30 min); t$_r$=8.98 min, 78% ee.

Example 59

3-{4-[2-(5-methyl-2-phenyl-oxazol-4-yl)-ethoxy]-phenyl}-2(S)-[2-(pyridine-N-oxide-3-carbonyl)-phenylamino]-propionic acid To Intermediate 89 (100 mg, 0.18 mmol) in DCM (5 mL) at RT was added mCPBA (57 mg, 0.33 mmol, 1.5 equiv). After 24 h a second 1.5 equiv mCPBA was added. The reaction mixture stirred 2 h, was concentrated to dryness and purified by silica gel flash column chromatography using DCM/MeOH 95/5 as eluent afforded 50 mg of the intermediate N-oxide: low resolution MS (ES) m/e 578.3 (MH⁺). Hydrolysis according to the method of Example 32 followed by purification via silica gel flash column chromatography using DCM/MeOH 90/10 as eluent afforded 20 mg of the title compound: low resolution MS (ES) m/e 562 (MH⁻); RP-HPLC (Vydac C-18, 25 cm×4.6 mm; 30–80% CH$_3$CN in H$_2$O with 0.1% TFA buffer; 25 minutes; 1 mL/min); t$_r$=15.70 min (t$_0$=3 min).

Example 60

2S-(2-benzoyl-phenylamino)-3-{4-[2-(5-methyl-3-phenyl-pyrazol-1-yl)-ethoxy]-phenyl}-propionic acid The title compound (77 mg) was prepared from 110 mg (0.20 mmol) of Intermediate 91 and 0.295 mL (0.295 mmol) of 1 M LiOH according to the method of Example 32 followed by purification via silica gel flash column chromatography eluting with chloroform/MeOH (9:1) and trituration with Et$_2$O/hexanes: low resolution MS (ES) m/e 546 (MH⁺); Anal. (C$_{34}$H$_{31}$N$_3$O$_4$.1.2H$_2$O) Calcd. C, 71.99; H, 5.94; N, 7.41; Found C, 71.96; H, 5.85; N, 7.33; RP-HPLC (C-18, 4.6 mm×25 cm; 50–100% CH$_3$CN in H$_2$O with 0.1% TFA; 30 minutes; 1 mL/min): t$_r$=14.5 min (t$_0$=3 min).

Example 61

2S-(2-benzoyl-phenylamino)-3-[4-(1-pyridin-2-yl-pyrrolidin-2S-yl-methoxy)-phenyl]-propionic acid The title compound (1.17 g) was prepared from 1.2 g (2.24 mmol) of Intermediate 93 and 3.4 mL (3.4 mmol) of 1 N LiOH according to the method of Example 32 followed by purification via trituration with CHCl$_3$/Et$_2$O: low resolution MS (ES) m/e 522 (M⁺); Anal. (C$_{32}$H$_{31}$N$_3$O$_4$.HCl.0.6H$_2$O) Calcd. C, 67.56; H, 5.88; N, 7.39; Cl, 6.23; Found C, 67.57; H, 5.87; N, 7.31; Cl, 6.46.

Example 62

2S-(2-benzoyl-phenylamino)-3-{4-[2-(1-methyl-4-phenyl-1H-imidazol-2-yl)-ethoxy]-phenyl}-propionic acid The title compound (70 mg) was prepared from 83 mg (0.15 mmol) of Intermediate 95 and 0.223 mL (0.223 mmol) of 1 N LiOH according to the method of Example 32 followed by purification via trituration with EtOAc: low resolution MS (ES) m/e 546 (MH⁺); Anal. (C$_{34}$H$_{31}$N$_3$O$_4$.HCl.0.5 H$_2$O) Calcd. C, 69.09; H, 5.63; N, 7.11; Cl, 6.00; Found C, 69.08; H, 5.63; N, 7.04; Cl, 6.04.

Example 63

2S-(2-benzoyl-phenylamino)-3-{4-[2-(3-furan-2-yl-5-methyl-pyrazol-1-yl)-ethoxy]-phenyl}-propionic acid A solution of 239 mg (0.911 mmol) of triphenylphosphine in 1.8 mL of anhydrous THF at 0° C. was treated with 0.143 mL (0.911 mmol) of DEAD in a dropwise fashion. After stirring for 10 min, the mixture was added to a solution of 342 mg (0.911 mmol) of Intermediate 23 and 175 mg (0.911 mmol) of Intermediate 97 in 1.8 mL of anhydrous THF at 25° C. The reaction was stirred at 25° C. for 15 h then concentrated in vacuo (@≦25° C.). The residue was purified by silica gel flash column chromatography using EtOAc/hexanes (1:1) as eluent to give impure intermediate ester. The crude ester was hydrolyzed according to the method of Example 32 followed by purification via silica gel flash column chromatography using CHCl$_3$/MeOH (9:1) as eluent followed by trituration with Et$_2$O to afford 180 mg (37%) of the title compound as a yellow solid: low resolution MS (ES) m/e 558 (MNa⁺), 536 (MH⁺); Anal. (C$_{32}$H$_{29}$N$_3$O$_5$.1.2H$_2$O) Calcd. C, 68.98; H, 5.68; N, 7.54; Found C, 68.65; H, 5.29; N, 7.76; TLC (CHCl$_3$/MeOH (9:1)): R$_f$=0.24.

Example 64

2S-(2-benzoyl-phenylamino)-3-{4-[2-(5-methyl-3-phenyl-[1,2,4]triazol-1-yl)-ethoxy]-phenyl}-propionic acid The title compound (141 mg) was prepared from 180 mg (0.32 mmol) of Intermediate 99 and 0.482 mL (0.482 mmol) of 1 N LiOH according to the method of Example 32 followed by purification via trituration with Et$_2$O: low resolution MS (ES) m/e 569 (MNa$^+$), 547 (MH$^+$); Anal. (C$_{33}$H$_{30}$N$_4$O$_4$.0.1H$_2$O) Calcd. C, 70.20; H, 5.71; N, 9.92; Found C, 70.35; H, 5.70; N, 9.98; TLC (CHCl$_3$/MeOH (9:1)): R$_f$=0.25.

Example 65

2S(2-benzoyl-phenylamino)-3-{4-[2-(3-methoxymethyl-5-methyl-2-phenyl-3H-imidazol-4-yl)-ethoxy]-phenyl}-propionic acid The title compound (324 mg) was prepared from 340 mg (0.56 mmol) of Intermediate 102 and 0.845 mL (0.845 mmol) of 1 N LiOH according to the method of Example 32 followed by purification via trituration with Et$_2$O: low resolution MS (ES) m/e 612 (MNa$^+$), 590 (MH$^+$); Anal. (C$_{36}$H$_{35}$N$_3$O$_5$.0.3H$_2$O) Calcd. C, 68.47; H, 5.84; N, 6.65; Found C, 68.46; H, 6.14; N, 6.41; TLC (CHCl$_3$/MeOH (9:1)): R$_f$=0.20.

Example 66

2S-(2-benzoyl-phenylamino)-3-{4-[2-(5-methyl-2phenyl-3H-imidazol-4-yl)-ethoxy]-phenyl}-propionic acid hydrochloride salt The title compound (162 mg) was prepared from 200 mg (0.36 mmol) of Intermediate 104 and 0.536 mL (0.536 mmol) of 1 N LiOH according to the method of Example 32 followed by purification via trituration with EtOAc/Et$_2$O: low resolution MS (ES) m/e 546 (MH$^+$); Anal. (C$_{34}$H$_{31}$N$_3$O$_4$.1.0H$_2$O) Calcd. C, 68.05; H, 5.71; N, 7.00; Cl, 5.91; Found C, 68.03; H, 5.74; N, 6.94; Cl, 5.98.

Example 67

2S-(2-benzoyl-phenylamino)-3-{4-[2-(5-methyl-2-phenyl-thiazol-4-yl)ethoxy]-phenyl}-propionic acid The title compound (283 mg) was prepared from 350 mg (0.61 mmol) of Intermediate 107 and 0.91 mL (0.91 mmol) of 1.0 N LiOH according to the method of Example 32 followed by purification via trituration with Et$_2$O/hexanes: low resolution MS (ES) m/e 586 (MNa$^+$), 563 (M$^+$); Anal. (C$_{34}$H$_{30}$N$_2$O$_4$S.0.3H$_2$O) Calcd. C, 71.89; H, 5.43; N, 4.93; S, 5.64; Found C, 71.91; H, 5.44; N, 4.93; S, 5.62.

Example 68

2(S)-(2-benzoyl-phenylamino)-3-{4-[2-(5-methyl-2-(3-methyl-thien-2-yl)-oxazol-4-yl)ethoxy]-phenyl}-propionic acid The title compound (90 mg) was prepared from 100 mg (0.17 mmol) of Intermediate 112 and 10.8 mg (0.258 mmol, 1.5 equiv) of LiOH according to the method of Example 32: MS (ES−) m/e 565.0 (MH−); Anal. (C$_{33}$H$_{30}$N$_2$O$_5$S 0.4 EtOAc) Calc. C, 69.04; H, 5.56; N, 4.65; Found C, 69.45; H, 5.95; N, 4.33.

Example 69

2(S)-(2-{4-[2-(5-nitro-2-pyridyloxy)-ethoxy]-phenyl}-1-methoxycarbonyl-ethylamino)-benzoic acid A solution of 109 mg (0.220 mmol) of Intermediate 152 in THF (2 mL) and EtOH (2 mL) was treated with 1M LiOH (1 mL). The reaction was stirred for 45 min. Water (10 mL) and 1N HCl (1 mL) were added. The reaction was extracted with EtOAc (2×30 mL). The combined organics were washed with brine (1×30 mL), dried over MgSO$_4$, filtered and concentrated. The material was purified by flash chromatography using EtOAc+0.1% AcOH as eluent to afford 25 mg (24%) of the title compound: $^1$H NMR (CDCl$_3$, 400 MHz) δ 9.07 (d, 1H, J=2.7), 8.36 (dd, 1H, J=2.8, 6.3), 7.91 (dd, 1H, J=1.6, 6.3), 7.35 (t, 1H J=7.4), 7.20 (d, 2H, J=8.7), 6.88 (dd, 3H, J=2.7, 7.7), 6.68 (t, 1H, J=7.4), 6.58 (d, 1H, J=8.3), 4.77 (t, 2H, J=4.6), 4.32 (m, 3H), 3.86 (s, 3H), 3.20 (ddd, 2H, J=5.1, 7.7, 7.7); low resolution MS m/e 480 (MH−).

Example 70

2(S)-(2-{4-[2-(5-chloro-2-pyridylsulfanyl)-ethoxy]-phenyl}-1-methoxycarbonyl-ethylamino)-benzoic acid The title compound (90 mg) was prepared from 155 mg (0.310 mmol) of Intermediate 153 according to the method of Example 69: $^1$H NMR (CDCl$_3$, 400 MHz) δ 8.38 (d, 1H, J=2.4), 8.19 (d, 1H, J=5.9), 7.91 (d, 1H, J=8.1), 7.46 (dd, 1H, J=2.5, 7), 7.34 (t, 1H, J=7.1), 7.19 (d, 2H, J=8.5), 7.13 (d, 1H, J=8.6), 6.87 (d, 2H, J=7.5 ), 6.67 (t, 1H, J=7.5), 6.57 (d, 1H, J=8.4), 4.30 (m, 1H), 4.18 (t, 2H, J=6.8), 3.85 (s, 3H), 3.52 (t, 2H, J=6.8), 3.18 (ddd, 2H, J=5.1, 7.5, 7.5); low resolution MS m/e 485 (MH−), 486 (M).

Example 71

2(S)-(2-{4-[2-(N-ethyl-2-methyl-toluidino)-ethoxy]-phenyl}-1-methoxycarbonyl-ethylamino)-benzoic acid The title compound (16 mg) was prepared from 90 mg (0.184 mmol) of Intermediate 154 according to the method of Example 69: $^1$H NMR (CDCl$_3$, 400 MHz) δ 8.19 (s 1H), 7.91 (d, 1H, J=6.7), 7.33 (t, 1H, J=8.4), 7.18 (d, 2H, J=7.9), 7.11 (m, 1H), 6.82 (m, 1H), 6.67 (t, 2H, J=8.5), 6.56 (d, 2H, J=8.4), 6.53 (m, 1H), 4.30 (q, 1H, J=6.9), 4.07 (m, 2H), 3.85 (s, 3H), 3.69 (m, 2H), 3.43 (m, 2H), 3.21 (ddd, 2H, J=5.3, 7.7, 7.7), 1.2 (m, 3H); low resolution MS m/e 475 (MH−), 476 (M).

Example 72

3-[4-(3-Benzoxazol-2-yl-thiazolidin-4(R)-ylmethoxy)-phenyl]-2(S)-(2-benzoyl-phenylamino)-propionic acid A solution of 100 mg (0.168 mmol) of Intermediate 116 dissolved in 5 mL of 2/2/1 (v/v) acetonitrile/MeOH/water was treated with 17.5 mg (0.337 mmol) of LiOH H2O for 2 h at room temperature. The reaction was quenched with an excess of citric acid, volatiles evaporated off and the product partitioned between EtOAc and water. The organics were then combined, dried and the solid residue left after rotary evaporation was further purified on preparative C18HPLC to afford 50 mg of the title compound: TLC: R$_f$=0.41 (chloroform/MeOH 9/1); MS (ES+) m/e 580 (M+1); Anal. (C$_{33}$H$_{29}$N$_3$O$_5$S.2TFA) Calc. C, 55.02; H, 3.87; N, 5.20; S, 3.97, Found C, 54.38; H, 3.90; N, 5.19; S 3.91.

Example 73

3-{4-[2-(benzoxazol-2-yl-methyl-amino)-ethoxy]-phenyl}-2-[2-(4-trifluoromethyl-benzoyl)-phenylamino-propionic acid A solution of Intermediate 113 (250 mg, 0.44 mmol), K$_2$CO$_3$, (182 mg, 1.3 mmol), Pd(Cl)$_2$ (PPh$_3$)$_2$ (9.2 mg, 0.013 mmol) and 4-trifluoromethylbenzene boronic acid (91.4 mg, 0.48 mmol) in dioxane (4.4 mL) was stirred under CO (1 atm, balloon) at 100° for 20 h. The resulting brown heterogeneous mixture was partitioned between water (50 mL) and EtOAc (50 mL). The EtOAc solution was washed with 2.0 M NaOH and brine (25 mL each), dried over $MgSO_4$ and concentrated to a brown oil. This material was chromatographed on silica gel (75 g) with EtOAc/hexane ½ as eluent to afford 3-{4-[2-(benzoxazol-2-yl-methyl-amino)-ethoxy]-phenyl}-2-[2-(4-trifluoromethyl-benzoyl)-phenylamino-propionic acid methyl ester (206.9 mg, 76%) as a yellow oil: low resolution MS ($ES^+$) m/e 618 ($MH^+$); TLC (EtOAc/hexane, (1/1)): $R_f$=0.51. A solution of the methyl ester (206.9 mg, 0.335 mmol) in THF/EtOH/1.0 M LiOH (3/1/1, 5 mL) was hydrolyzed following the conditions outlined in Example 32 to afford the title compound (175 mg, 86%) as a yellow solid: mp 177–178° C.; low resolution MS ($ES^+$) m/e 604 ($MH^+$); Anal. Calc. for $C_{33}H_{28}F_3N_3O_5 \cdot 1.0 H_2O$: C, 63.76; H, 4.86; N, 6.76; Found: C, 63.44; H, 4.71; N, 6.52.

Example 74

3-{4-[2-(benzoxazol-2-yl-methyl-amino)-ethoxy]-phenyl}-2-[2-(2-thiophenecarbonyl)-phenylamino-propionic acid Using the protocol reported for Example 73, the title compound was synthesized from Intermediate 113 and 2-thiophene boronic acid in 27% overall yield and isolated as a yellow solid: mp 76–80° C.; low resolution MS ($ES^+$) m/e 542 ($MH^+$); high resolution MS ($FAB^+$) Calc. for $C_{30}H_{27}N_3O_5S_1$ ($MH^+$): 542.1750; Found: 542.1750.

Example 75

3-{4-[2-(benzoxazol-2-yl-methyl-amino)ethoxy]-phenyl}-2-[2-(3-thiophenecarbonyl)-phenylamino-propionic acid Using the protocol reported for Example 73, the title compound was synthesized from Intermediate 113 and 3-thiophenene boronic acid in 28% overall yield and isolated as a yellow solid: mp 85–95° C.; low resolution MS ($ES^+$) m/e 542 ($MH^+$); Anal. Calc. for $C_{30}H_{27}N_3O_5S_1 \cdot 1.5H_2O$: C, 63.37; H, 5.32; N, 7.39; Found: C, 63.48; H, 4.97; N, 7.08.

Example 76

3-{4-[2-(benzoxazol-2-yl-methyl-amino)-ethoxy]-phenyl}-2-[2-(3-trifluoromethylbenzoyl)-phenylamino-propionic acid Using the protocol reported for Example 73, the title compound was synthesized from Intermediate 113 and 3-trifluorobenzene boronic acid in 63% overall yield and isolated as a yellow solid: mp 159–160° C.; low resolution MS ($ES^+$) m/e 604 ($MH^+$); Anal. Calc. for $C_{33}H_{28}F_3N_3O_5 \cdot 0.5 H_2O$: C, 64.70; H, 4.77; N, 6.86; Found: C, 64.77H, 4.75; N, 6.83.

Example 77

3-{4-[2-(benzoxazol-2-yl-methyl-amino)-ethoxy]-phenyl}-2-[2-(2-trifluoromethyl-benzoyl)-phenylamino-propionic acid Using the protocol reported for Example 73, the title compound was synthesized from Intermediate 113 and 2-trifluoromethylbenzene boronic acid in 70% overall yield and isolated as a yellow solid: mp 102–106° C.; low resolution MS ($ES^+$) m/e 604 ($MH^+$); Anal. Calc. for $C_{33}H_{28}F_3N_3O_5 \cdot 1.0 H_2O$: C, 63.76; H, 4.86; N, 6.76; Found C, 63.82H, 4.72; N, 6.58.

Example 78

3-{4-[2-(benzoxazol-2-yl-methyl-amino)-ethoxy]-phenyl}-2-[2-(3-methoxy-benzoyl)-phenylamino-propionic acid Using the protocol reported for Example 73, the title compound was synthesized from Intermediate 113 and 3-methoxybenzene boronic acid in 61% overall yield and isolated as a yellow solid: mp 76–80° C.; low resolution MS ($ES^+$) m/e 566 ($MH^+$); Anal. Calc. for $C_{33}H_3lN_3O_6 \cdot 1.5 H_2O$: C, 66.88; H, 5.78; N, 7.09; Found: C, 66.53H, 5.45; N, 6.78.

Example 79

3-{4-[2-(benzoxazol-2-yl-methyl-amino)-ethoxy]-phenyl}-2-[2-(2-methoxy-benzoyl)-phenylamino-propionic acid Using the protocol reported for Example 73, the title was synthesized from Intermediate 113 and 2-methoxybenzene boronic acid in 49% overall yield and isolated as a yellow solid: mp 98–102° C.; low resolution MS ($ES^+$) m/e 566 ($MH^+$); Anal. Calc. for $C_{33}H_{31}N_3O_6 \cdot 2.0 H_2O$: C, 65.88; H, 5.86; N, 6.98; Found: C, 65.98; H, 5.50; N, 6.64.

Example 80

3-{4-[2-(benzoxazol-2-yl-methyl-amino)-ethoxy]-phenyl}-2-[2-(3-methyl-benzoyl)-phenylamino-propionic acid Using the protocol reported for Example 73, the title compound was synthesized from Intermediate 113 and 3-methylbenzene boronic acid in 52% overall yield and isolated as a yellow solid: mp 80–85° C.; low resolution MS ($ES^+$) m/e 550 ($MH^+$); Anal. Calc. for $C_{33}H_{31}N_3O_5 \cdot 1.5 H_2O$: C, 68.74; H, 5.94; N, 7.29; Found: C, 68.49H, 5.66; N, 7.00.

Example 81

2-[2-(4-dimethylaminomethyl-benzoyl)-phenylamino]-3-{4-[2-(5-methyl-2-phenyl-oxazol-4-yl)-ethoxy]-phenyl}-propionic acid hydrochloride To a solution of Intermediate 123 (96 mg, 1.63 mmol), dimethylamine (0.85 mL, 0.17 mmol), and HOAc (3.7 mL, 0.065 mmol) in MeOH/THF ((3/1), 4 mL) was added sodium cyanoborohydride (20 mg, 0.33 mmol). The resulting solution was stirred under $N_2$ for 6 h. The solution was diluted with EtOAc (50 mL) and washed with 1.0 M $NaHCO_3$ (20 mL) and brine (20 mL). This solution was dried over $MgSO_4$ and concentrated to a yellow semi-solid which was flash chromatographed on silica gel with EtOAc to elute the less polar products and then with EtOAc/MeOH 98/2 to elute the product dimethylbenzylamine methyl ester: low resolution MS (ES) m/e 618 ($MH^+$); TLC (EtOAc); $R_f$=0.13. This material was hydrolyzed according to the procedure outlined in Example 32 to give the title compound (28.0 mg, 27% for 2 steps) as a yellow solid: mp 103–105° C.; low resolution MS (ES) m/e 604 ($MH^+$); high resolution MS (FAB+) m/e ($MH^+$) Calc. for $C_{37}H_{37}N_3O_5$: 604.2811, Found: 604.2816.

Example 82

2-[2-(4-aminomethyl-benzoyl)-phenylamino]-3-{4-[2-(6-methyl-2-phenyl-oxazol-4-yl)-ethoxy]-phenyl}-propionic acid hydrochloride To a solution of Intermediate 123 (167 mg, 0.284 mmol) in THF (20 mL) was added sodium borohydride (11 mg, 284 mmol). The resulting solution was stirred under $N_2$ for 30 min and quenched with acetone (1 mL). After stirring for an additional 30 min, the mixture was diluted with EtOAc (50 mL) and washed with 2.0 M NaOH, 1.0 M $NaHCO_3$ and brine (20 mL each). This solution was dried over $MgSO_4$ and concentrated to a dark brown oil which was flash chromatographed on silica gel with EtOAc/hexane 2/3 as eluent to give the benzyl alcohol (129 mg, 77% yield) as a yellow oil: low resolution MS ($ES^+$) m/e 591($MH^+$); TLC (EtOAc/hexane (1/1)); $R_f$=0.33. To a solution of the above benzyl alcohol (97 mg, 0.165 mmol) and triethylamine (27.5 mL, 0.20 mmol) in $CH_2Cl_2$ (3 mL) was added methanesulfonyl chloride (14.0 mL, 0.18 mmol). The resulting solution was stirred under $N_2$ for 3 h. The solution was diluted with EtOAc (50 mL) and washed with 2.0 M HCl, water, 1.0 M $NaHCO_3$ and brine (20 mL each). The solution was dried over $MgSO_4$ and concentrated to give the corresponding mesylate (105 mg) as a yellow oil: low resolution MS ($ES^+$) m/e 669 ($MH^+$); TLC (EtOAc/toluene (1/3)); $R_f$=0.74. To a solution of the above mesylate (105 mg, 0.156 mmol) in DMF (2.5 mL) was added $NaN_3$ (31 mg, 0.18 mmol). The resulting solution was stirred under $N_2$ for 16 h. After adding 1.0 M $NaHCO_3$ (1 mL), the solvents were removed by rotary evaporation and the residue partitioned between water (20 mL) and EtOAc (50 mL). The EtOAc solution was washed with water and brine (20 mL each), dried over $MgSO_4$ and concentrated to provide the benzyl azide (96.3 mg) as a yellow oil: low resolution MS ($ES^+$) m/e 616 ($MH^+$); TLC (EtOAc/hexane (1/2)); $R_f$=0.45. To a solution of the above azide (96 mg, 0.156 mmol) in THF (5 mL) and water (0.2 mL) was added triphenylphosphine (45 mg, 0.172 mmol). The resulting solution was stirred under $N_2$ for 24 h. The solution was then diluted with EtOAc (50 mL) and washed with 2.0 M NaOH (10 mL) and brine (25 mL). The organic solution was dried over $MgSO_4$ and concentrated to a yellow oil which was flash chromatographed on silica gel with $CHCl_3$/MeOH 95/5 as eluent to give the benzyl amine methyl ester (73 mg, 75% yield from the benzyl alcohol) as a yellow oil: low resolution MS (ES+) m/e 590 ($MH^+$); TLC ($CHCl_3$/MeOH (9/1)); $R_f$=0.23. A solution of the above benzyl amine methyl ester in THF/EtOH/1.0 M LiOH (3/1/1, 5 mL) was stirred for 16 h under $N_2$. The solvents were removed by rotary evaporation and the residue dissolved in water (15 mL) and washed with ether (25 mL). The aqueous layer was acidified to pH 2 with 2.0 M HCl to give a flocculent suspension. This mixture was concentrated to 5 mL and centrifuged (7100 rpm, 5 min). The aqueous solution was decanted and the resulting yellow pellet resuspended in water (10 mL) and centrifuged as above (3x). The yellow solid thus obtained was suspended in water (2 mL) and lyophilized. The resulting yellow solid was suspended in EtOAc and centrifuged (3x). The resulting pellet was dried under vacuum to provide the title compound (56.8 mg, 82% yield) as a yellow powder: mp 134–136° C.; low resolution MS ($ES^+$) m/e 576 ($MH^+$); high resolution MS ($FAB^+$) m/e ($MH^+$) Calc. for $C_{35}H_{33}N_3O_5$: 576.2498; Found: 576.2495; TLC ($CHCl_3$/MeOH (4/1)+1 drop HOAc); $R_f$=0.30.

Example 83

3-{4-[2-(benzoxazol-2-yl-methyl-amino)-ethoxy]-phenyl}-2-[2-(2,6-dimethylbenzoyl)-phenylamino-propionic acid Using the protocol reported for Example 73, the title compound was synthesized from Intermediate 113 and 2,6-dimethylbenzene boronic acid in 13% overall yield and isolated as a yellow solid: mp 85–90° C.; low resolution MS ($ES^+$) m/e 564 ($MH^+$); high resolution MS ($FAB^+$) Calc. for $C_{34}H_{33}N_3O_5$ ($MH^+$): 564.2498; Found: 564.2484.

Example 84

3-(2-{1-carboxy-2-[4-(2-{5-methyl-2-phenyl-oxazol-4-yl}-ethoxy)-phenyl]-ethylamino}-benzoyl benzoic acid To a solution of Intermediate 124 (75 mg, 128 mmol) in acetone (5 mL) was added dropwise 2.67 M Jones' reagent (48 mL, 128 mmol). The resulting dark green solution was stirred for 2 h. The reaction was quenched with the addition of iPrOH (1 mL). After stirring for an additional 15 min, the mixture was diluted with EtOAc (50 mL) and washed with 1.0 M HCl (20 mL), water (20 mL) and brine (10 mL). This solution was dried over $MgSO_4$ and concentrated to a brown oil which was flash chromatographed on silica gel eluting with $CHCl_3$/MeOH (98/2 containing 0.1% HOAc) to produce 3-(2-{1-carboxy-2-[4-(2-{5-methyl-2-phenyl-oxazol-4-yl}-ethoxy)-phenyl]-ethylamino}-benzoyl benzoic acid methyl ester(25 mg, 33%) as a yellow oil: low resolution MS (ES) m/e 605 ($MH^+$); TLC ($CHCl_3$/MeOH (95/5)); $R_f$=0.20. The above methyl ester was hydrolyzed according to the procedure outlined in Example 32 to produce the title compound (24 mg, 98%) as a yellow solid: mp 107–110° C.; low resolution MS (ES) m/e 589 (M–H⁻); Anal. Calc. for $C_{35}H_{30}N_2O_7 \cdot 0.5H_2O$: C, 70.11; H, 5.21; N, 4.67; Found C, 69.99; H, 5.28; N, 4.51.

Example 85

2-[2-(3-hydroxymethyl-benzoyl)-phenylamino]-3-{4-[2-(5-methyl-2-phenyl-oxazol-4-yl)-ethoxy]-phenyl}-propionic acid To a solution of Intermediate 124 (257 mg, 0.43 mmol) in THF (10 mL) was added sodium borohydride (16.5 mg, 0.43 mmol). The resulting solution was stirred under $N_2$ for 45 min and the quenched with acetone (1 mL) and stirred for an additional 10 min. After addition of 1.0 M $NaHCO_3$ (1 mL) the solvents were removed by rotary evaporation and the residue partitioned between EtOAc (50 mL) and water (20 mL). The EtOAc layer was washed with water (20 mL) and brine (10 mL) and dried over $MgSO_4$. This solution was concentrated to give a yellow oil which was flash chromatographed on silica gel (30 g) with EtOAc/hexane (2/3) to give the 2-[2-(3-hydroxymethyl-benzoyl)-phenylamino]-3-{4-[2-(5-methyl-2-phenyl-oxazol-4-yl)-ethoxy]-phenyl}-propionic acid methyl ester (211 mg, 82%) as a yellow oil: low resolution MS ($ES^+$) m/e 591 ($MH^+$); TLC (EtOAc/hexane (1/1)); $R_f$=0.39. A solution of the methyl ester (45 mg) was hydrolyzed according to the procedure outlined in Example 32 to produce the title compound (43 mg, 97%) as a yellow solid: mp 87–90° C.; low resolution MS (ES⁻) m/e 575 (M–H⁻); Anal. Calc. for $C_{35}H_{32}N_2O_6 \cdot 0.5H_2O$) C, 71.78; H, 5.68; N, 4.78; Found C, 71.70; H, 6.06; N, 4.45.

Example 86

2-[2-(3-aminomethyl-benzoyl)-phenylamino]-3-{4-[2-(5-methyl-2-phenyl-oxazol-4-yl)-ethoxy]-phenyl}-propionic acid hydrochloride Using the same synthetic route used for Example 82, Intermediate 124 was converted to the title compound: mp 138–140° C.; low resolution MS ($ES^+$) m/e 576 ($MH^+$); Anal. Calc. for $C_{35}H_{33}N_3O_5 \cdot HCl \cdot 0.75H_2O$) C, 67.19; H, 5.72; N, 6.72; Found C, 67.25; H, 5.92; N, 6.35.

Example 87

2-[2-(3-dimethylaminomethyl-benzoyl)-phenylamino]-3-{4-[2-(5-methyl-2-phenyl-oxazol-4-yl)-ethoxy]-phenyl}-propionic acid hydrochloride Using the analogous route used for Example 81, Intermediate 124 was converted to the title compound: mp 120–124° C.; low resolution MS (ES$^+$) m/e 604 (MH$^+$); Anal. Calc. for $C_{37}H_{37}N_3O_5 \cdot HCl \cdot 3H_2O$): C, 64.01; H, 6.39; N, 6.05; Found C, 63.62; H, 6.03; N, 5.78.

Example 88

2-(S)-(1-carboxy-2-{4-{2-(5-methyl-2-phenyl-oxazol-4-yl)-ethoxy]-phenyl}-ethylamino)-benzoic acid methyl ester A solution of Intermediate 125 (582 mg, 1.13 mmol) in THF/EtOH/1.0 M LiOH (3/1/1, 15 mL) was stirred under $N_2$ for 2 h. A solution of 0.4M HCl (25 mL) was added and the mixture was then extracted with EtOAc (150 mL). This extract was washed with brine (25 mL) and dried over $Na_2SO_4$ and concentrated to a white solid. This material was flash chromatographed on silica gel with EtOAc (containing 0.1% HOAc) to produce the title compound (450 mg, 80%) as a white solid: mp 140–141° C.; $^1$H NMR (DMSO-d$_6$, 400 MHz) δ 12.95 (br s, 1H), 7.94–7.88 (m, 3H), 7.77 (d, 1H, J=8.0), 7.49–7.45 (m, 3H), 7.35 (t, 1H, J=7.9), 7.08 (d, 2H, J=8.5), 6.82 (d, 1H, J=8.6), 6.69 (d, 1H, J=8.6), 6.59 (t, 1H, J=7.5), 4.42–4.38 (m, 1H), 4.15 (t, 2H, J=6.7), 3.75 (s, 3H), 3.09 (dd, 1H, J=5.3, 13.9), 2.96 (dd, 1H, J=6.1, 14.0), 2.89 (t, 2H, J=6.6), 2.32 (s, 3H); low resolution MS (ES$^+$) m/e 501 (MH$^+$); TLC (EtOAc): R$_f$=0.51; Chiral Chromatography (Chiralcel OD-H, 4.6×250 mm, EtOH/hexane (3/7) and 0.1% TFA, 0.7 mL/min): t$_r$=7.8 min (major enantiomer), 7.2 min (minor enantiomer): 88% ee; [a]$_D$=–9.8°, a=–0.109°, c=1.11 (CH$_2$Cl$_2$) (not corrected for ee); Anal. Calc. for $C_{29}H_{28}N_2O_6$: C, 69.51; H, 5.68; N, 5.54; Found: C, 69.40; H, 5.74; N, 5.42.

Example 89

2-(S)-(1-carboxy-2-{4-{2-(5-methyl-2-phenyl-oxazol-4-yl)-ethoxy]-phenyl}-ethylamino)-benzoic acid 2-aminoethyl amide hydrochloride To a solution of Intermediate 126 (48.9 mg, 0.98 mmol), HOBt (5 mg, 37 mmol), triethylamine (20.4 mL, 146 mmol) and tert-butyl N-(2-aminoethyl)carbamate (16.9 mL, 107 mmol) in $CH_2Cl_2$ (5 mL) was added 1-ethyl-3-(3-dimethylaminopropyl)carbodiimide (22.4 mg, 117 mmol). The resulting solution was stirred for 16 h under $N_2$ and then diluted with EtOAc (50 mL) and washed with 25 mL each of 0.5 M HCl (2×), saturated $NH_4Cl$, water and 2.0 M $NaHCO_3$ (2×) and brine (10 mL). This solution was dried over $MgSO_4$ and concentrated to a brown oil which was flash chromatographed on silica gel with EtOAc/hexane 1/1 as eluent to afford (37 mg, 59%) of a colorless oil: low resolution MS (ES$^+$) m/e 643 (MH$^+$); TLC (hexane/EtOAc (1/1)): R$_f$=0.35. A solution of this material in THF/EtOH/1.0 M LiOH (3/1/1, 5 mL) was stirred under $N_2$ for 16 h. The solvents were removed by rotary evaporation and the residue taken up in water (10 mL) and acidified with 2.0 M HCl (2 mL). The resulting mixture was extracted with EtOAc (50 mL). This extract was washed with brine (10 mL), dried over $MgSO_4$ and concentrated to a colorless solid. This material was dissolved in 4.0 M HCl in dioxane (2 mL) and stirred under $N_2$ for 1 h. The dioxane was removed in vacuo to afford the title compound (42 mg, 100%) as a hygroscopic white solid: mp 110–115° C.; low resolution MS (ES$^+$) m/e 529 (MH$^+$); high resolution MS (FAB$^+$) Calc. for $C_{30}H_{32}N_4O_5$ (MH$^+$): 529.2451; Found: 529.2454; TLC (CHCl$_3$/MeOH (9/1)): R$_f$=0.04.

Example 90

2-(S)-(1-carboxy-2-{4-{2-(5-methyl-2-phenyl-oxazol-4-yl)-ethoxy]-phenyl}-ethylamino)-benzoic acid 3-aminopropyl amide hydrochloride By use of the analogous route to Example 89, the title compound was obtained in 95% yield from Intermediate 126 and tert-butyl N-(3-aminopropyl)carbamate as a hygroscopic white solid: mp 95–98° C.; low resolution MS (ES$^+$) m/e 543 (MH$^+$); high resolution MS (FAB$^+$) Calc. for $C_{31}H_{34}N_4O_5$ (MH$^+$): 543.2607; Found: 543.2609; TLC (CHCl$_3$/MeOH (9/1)): R$_f$=0.04.

Example 91

2-(S)-(1-carboxy-2-{4-{2-(5-methyl-2-phenyl-oxazol-4-yl)ethoxy]-phenyl}-ethylamino)-benzoic acid methyl amide To a solution of Intermediate 126 (49.5 mg, 0.10 mmol), HOBt (6.7 mg, 49 mmol), triethylamine (41.3 mL, 0.30 mmol) and methylamine (12.8 mL (40% solution in water), 0.15 mmol) in $CH_2Cl_2$ was added 1-ethyl-3-(3-dimethylaminopropyl) carbodiimide (22.7 mg, 0.12 mmol). The resulting solution was stirred for 16 h under $N_2$ and then diluted with EtOAc (50 mL) and washed with 20 mL each of 0.5 M HCl (2×), saturated $NH_4Cl$, water and 2.0 M $NaHCO_3$ (2×). This solution was dried over $MgSO_4$ and concentrated to a yellow oil which was flash chromatographed on silica gel (10 g) with EtOAc/hexane (1/1) to afford 33.8 mg (67%) of a colorless oil: low resolution MS (ES$^+$) m/e 514 (MH$^+$); TLC (hexane/EtOAc (1/1)): R$_f$=0.31. This material was hydolyzed according to the procedure outlined in Example 32 to afford the title compound (33.4 mg, 100%) as a white solid: mp 85–90° C.; $^1$H NMR (DMSO-d$_6$, 400 MHz) δ 12.71 (s, 1H), 8.24–8.20 (m, 2H), 7.90–7.88 (m, 2H), 7.49–7.45 (m, 4H), 7.21 (t, 1H, J=7.2), 7.10 (d, 2H, J=8.5), 6.82 (d, 2H, J=8.6), 6.6–6.53 (m, 2H), 4.23–4.22 (m, 1H), 4.15 (t, 2H, J=6.5), 3.02 (dd, 1H, J=5.6, 13.8), 2.92–2.87 (m, 3H), 2.69 (d, 3H, J=4.5), 2.33 (s, 3H); low resolution MS (ES$^+$) m/e 500 (MH$^+$); TLC (hexane/EtOAc (2/1)): R$_f$=0.06.

Example 92

3-{4-[2-(benzoxazol-2-yl-methyl-amino)-ethoxy]-phenyl}-2-[2-(3-hydroxy-benzoyl)-phenylamino]-propionic acid The title compound (140 mg) was prepared from 500 mg (0.88 mmol) of Intermediate 130 and 111 mg (2.65 mmol) of lithium hydroxide monohydrate according to the method of Example 32 followed by purification via silica gel chromatography using MeOH/dichloromethane 1:19 as eluent: low resolution MS (ES) m/e 552 (MH$^+$); RP-HPLC (50–100% CH$_3$CN in water with 0.1% TFA buffer, 25 min): t$_r$=7.46 min.

Example 93

3-{4-[2-(5-methyl-2-phenyl-oxazol-4-yl)-ethoxy]-phenyl}-2-[2-(4-propylsulfamoyl-benzoyl)-phenylamino]-propionic acid The title compound (31 mg) was prepared from 70 mg (0.102 mmol) of Intermediate 131 and 21 mg (0.31 mmol)

of lithium hydroxide monohydrate according to the method of Example 32 followed by purification via trituration with MeOH/hexane (1:19) and then EtOAc/hexane (1:19): low resolution MS (ES) m/e 668.3 (MH$^+$); RP-HPLC (50–100% CH$_3$CN in water with 0.1% TFA buffer, 25 min): t$_r$=14.52 min; Anal. (C$_{37}$H$_{37}$N$_3$O$_7$S.0.5H$_2$O) C, 65.66; H, 5.66; N, 6.21; Found C, 65.82; H, 5.61; N, 6.18.

Example 94

2-[2-(3-amino-benzoyl)-phenylamino]-3-{4-[2-(5-methyl-2-phenyl-oxazol-4-yl)-ethoxy]-phenyl}-propionic acid The title compound (35 mg) was prepared from 73 mg (0.13 mmol) of Intermediate 132 and 19 mg (0.39 mmol) of lithium hydroxide monohydrate according to the method of Example 32 followed by purification via silica gel chromatography with ethyl MeOH/dichloromethane (gradient of 1:19 to 1:4) as eluent followed by trituration with MeOH/hexane (1:19) and then EtOAc/hexane (1:9): low resolution MS (ES) m/e 562 (MH$^+$); RP-HPLC (0–100% CH$_3$CN in water with 0.1% TFA buffer, 25 min): t$_r$=16.51 min; high resolution MS (FAB) m/e 562.2348 (MH$^+$), C$_{34}$H$_{31}$N$_3$O$_5$ requires 562.2342.

Example 95

2-[2-(3-methanesulfonylamino-benzoyl)-phenylamino]-3-{4-[2-(5-methyl-2-phenyl-oxazol-4-yl)-ethoxy]-phenyl}-propionic acid The title compound (23 mg) was prepared from 60 mg (0.10 mmol) of Intermediate 133 and 1 mg (0.28 mmol) of lithium hydroxide monohydrate according to the method of Example 32 followed by purification via silica gel chromatography using MeOH/dichloromethane (1:9 with 1% acetic acid) as eluent: low resolution MS (ES) m/e 640.2 (MH$^+$); RP-HPLC (50–100% CH$_3$CN in water with 0.1% TFA buffer, 25 min): t$_r$=12.02 min; high resolution MS (FAB) 640.2116 (MH$^+$), C$_{35}$H$_{33}$N$_3$O$_7$S requires 640.2117.

Example 96

2-[2-(3-methoxycarbonylamino-benzoyl)-phenylamino]-3-{4-[2-(5-methyl-2-phenyl-oxazol-4-yl)-ethoxy]-phenyl}-propionic acid The title compound (28 mg) was prepared from 50 mg (0.79 mmol) of Intermediate 134 and 12 mg (0.28 mmol) of lithium hydroxide monohydrate according to the method of Example 32 followed by purification via silica gel chromatography with MeOH/dichloromethane (1:9 with 0.1% acetic acid) as eluent and trituration with EtOAc/hexane (1:9): low resolution MS (ES) m/e 642 (MNa$^+$), 620 (MH$^+$); RP-HPLC (50–100% CH$_3$CN in water with 0.1% TFA buffer, 25 min): t$_r$=13.73 min; high resolution MS (FAB) 620.2384 (MH$^+$), C$_{36}$H$_{33}$N$_3$O$_7$ requires 620.2397.

Example 97

2-[2-(3-hydroxy-benzoyl)-phenylamino]-3-{4-[2-(5-methyl-2-phenyl-oxazol-4-yl)-ethoxy]-phenyl}-propionic acid The title compound (13 mg) was prepared from 50 mg (0.087 mmol) of Intermediate 136 and 13.6 mg (0.32 mmol) of lithium hydroxide monohydrate according to the method of Example 32 followed by purification via silica gel chromatography with MeOH/dichloromethane (gradient of 1:9 to 1:9+0.1% acetic acid) as eluent and trituration with MeOH/hexane (1:19): low resolution MS (ES) m/e 561 (M–H)$^+$; RP-HPLC (50–100% CH$_3$CN in water with 0.1% TFA buffer, 25 min): t$_r$=12.121 min; high resolution MS (FAB) m/e 563.2186 (MH$^+$), C$_{34}$H$_{30}$N$_2$O$_6$ requires 563.2182.

Example 98

2-[2-(3-Carbanoylmethoxy-benzoyl)-phenylamino]-3-{4-[2-(5-methyl-2-phenyl-oxazol-4-yl)-ethoxy]-phenyl}-propionic acid The title compound (16 mg) was prepared from 73 mg (0.12 mmol) of Intermediate 137 and 16.0 mg (0.38 mmol) of lithium hydroxide monohydrate according to the method of Example 32 followed by purification via silica gel chromatography with EtOAc/hexane (1:9) as eluent: low resolution MS (ES) m/e 618 (M–H)$^+$; RP-HPLC (50–100% CH$_3$CN in water with 0.1% TFA buffer, 25 min): t$_r$=10.06 min; high resolution MS (FAB) m/e 620.2384 (MH$^+$), C$_{36}$H$_{33}$N$_3$O$_7$ requires 620.2397.

Example 99

2(S)-(2-benzoyl-phenylamino)-3-{4-[2-(5-methyl-2-pyridin-4-yl-oxazol-4-yl)-ethoxy]-phenyl}-propionic acid The title compound (191 mg) was prepared from 210 mg (0.37 mmol) of Intermediate 143 and 49.0 mg (1.12 mmol) of lithium hydroxide monohydrate according to the method of Example 32 followed by purification via silica gel chromatography with MeOH/dichloromethane (1:9) as eluent: low resolution MS (ES) m/e 548 (MH$^+$); high resolution MS (EI) m/e 548.2194 (MH$^+$), C$_{33}$H$_{29}$N$_3$O$_5$ requires 548.2185.

Example 100

2(S)-(2-benzoyl-phenylamino)-3-(4-{2-[5-methyl-2-(4-methyl-piperazin-1-yl)-thiazol-4-yl]-ethoxy}-phenyl)-propionic acid hydrochloride The title compound (429 mg) was prepared from 500 mg (0.84 mmol) of Example 42 and 110 mg (2.52 mmol) of lithium hydroxide monohydrate according to the method of Example 32 followed by purification via silica gel chromatography using MeOH/EtOAc (gradient of 2:3 to 3:2 to 4:1) and acidified with 0.75 mL (0.74 mmol) of 1 M HCl in diethyl ether. The solvent was removed in vacuo to give the title compound as a hydrochloride salt; TLC (MeOH/EtOAc (2:3)): R$_f$=0.17; low resolution MS (ES) m/e 585 (MH$^+$); high resolution MS (EI) m/e 585.2541 (MH$^+$), C$_{33}$H$_{36}$N$_4$O$_4$S requires 585.2536.

Example 101

2(S)-(2-benzoyl-phenylamino)-3-(4-{2-[5-methyl-2-(4-tert-butoxycarbonyl-piperazin-1-yl)-thiazol-4-yl]-ethoxy}-phenyl)-propionic acid The title compound (80 mg) was prepared from 140 mg (0.20 mmol) of Intermediate 147 and 26 mg (0.60 mmol) of lithium hydroxide monohydrate according to the method of Example 32 followed by purification via silica gel chromatography using MeOH/EtOAc (gradient of 3:7 to 1:1): low resolution MS (ES) m/e 669 (M–H)$^+$; high resolution MS (FAB) m/e 671.2915 (MH$^+$), C$_{37}$H$_{42}$N$_4$O$_6$S requires 671.2903.

Example 102

2(S)-(2-benzoyl-phenylamino)-3-{4-[2-(5-methyl-2-piperazin-4-yl-thiazol-4-yl)-ethoxy]-phenyl}-propionic acid To a stirred solution of 65 mg (0.10 mmol) of Example 101 in 1 mL of 1,4-dixoane was added 1.5 mL of 4 M HCl in 1,4-dioxane. After stirring at RT for 3 h, the solvent was removed in vacuo. The residue was purified by reverse phase HPLC using acetonitrile/water with 0.1% TFA buffer (gradient of 30–50% over 30 min) as eluent to give the title compound as a monotrifluoro acetate salt: low resolution MS (ES) m/e 571.2 (MH$^+$); high resolution MS (FAB) m/e 571.2382 (MH$^+$), $C_{32}H_{34}N_4O_4S$ requires 571.2379.

Example 103

2(S)-(2-benzoyl-phenylamino)-3-(4-{2-[5-methyl-2-(4-methylsulfonyl-piperazin-1-yl)-thiazol-4-yl]-ethoxy}-phenyl)-propionic acid The title compound (123 mg) was prepared from 140 mg (0.21 mmol) of Intermediate 149 and 26 mg (0.60 mmol) of lithium hydroxide monohydrate according to the method of Example 32 followed by purification via trituration with EtOAc/hexane (1:19): low resolution MS (ES) m/e 647 (M–H)$^+$; high resolution MS (FAB) m/e 649.2151 (MH$^+$), $C_{33}H_{36}N_4O_6S_2$ requires 649.2155.

Example 104

2(S)-(1-carboxy-2-{4-[2-(4-dimethylamino-phenyl)-ethoxy]-phenyl}-ethylamino)-benzoic acid methyl ester The title compound (30 mg) was prepared from 290 mg (0.61 mmol) of Intermediate 155 and 71 mg (1.83 mmol) of lithium hydroxide monohydrate according to the method of Example 32 followed by purification via silica gel chromatography using MeOH/EtOAc (gradient of 0:1 to 1:9) as eluent: low resolution MS (ES) m/e 461 (M–H)$^+$; high resolution MS (FAB) m/e 463.2228 (MH$^+$), $C_{27}H_{30}N_2O_5$ requires 463.2233.

Example 105

2(S)-[1-methoxycarbonyl-2-(4-{2-[5-methyl-2-(4-methyl-piperazin-1-yl)-thiazol-4-yl]-ethoxy}-phenyl)-ethylamino]-benzoic acid The title compound (150 mg) was prepared from 360 mg (0.65 mmol) of Intermediate 156 and 92 mg (2.19 mmol) of lithium hydroxide monohydrate according to the method of Example 32 followed by purification via silica gel chromatography using MeOH/EtOAc (gradient of 3:2 to 3:2 with 1% NH$_4$OH to 4:1 with 1% NH$_4$OH and 1% water) as eluent: $^1$H NMR (DMSO-d$_6$, 400 MHz) δ 8.04 (d, 1H, J=6.8), 7.72 (d, 1H, J=8.0), 7.26 (t, 1H, J=7.2), 7.04 (d, 2H, J=8.4), 6.72 )d, 2H, J=8.5), 6.59 (d, 1H, J=8.7), 6.47 (t, 1H, J=7.2), 4.06 (m, 3H), 3.74 (s, 3H), 3.26 (m, 4H), 3.03 (dd, 1H, J=5.1, 13.8), 2.87 (dd, 1H, J=6.5, 13.7), 2.79 (t, 2H, J=6.8), 2.34 (m, 4H), 2.19 (s, 3H), 2.17 (s, 3H); TLC (MeOH/EtOAc low resolution MS (ES) m/e 537 (M–H)$^+$; high resolution MS (FAB) m/e 539.2328 (MH$^+$), $C_{28}H_{34}N_4O_5S$ requires 539.2328.

Example 106

2(S)-(1-carboxy-2-{4-[2-(4-chloro-phenyl)-ethoxy]-phenyl}-ethylamino)-benzoic acid methyl ester The title compound (142 mg) was prepared from 230 mg (0.49 mmol) of Intermediate 157 and 70 mg (1.67 mmol) of lithium hydroxide monohydrate according to the method of Example 32 followed by purification via silica gel chromatography using MeOH/EtOAc (gradient of 0:1 to 1:19 to 1:9 with 1% NH$_4$OH) as eluent: low resolution MS (ES) m/e 452 (MH)$^+$; high resolution MS (FAB) m/e 454.1421 (MH$^+$), $C_{25}H_{24}NO_5Cl$ requires 454.1421.

Example 107

2(S)-(1-carboxy-2-{4-[2-(4-trifluoromethoxy-phenyl)-ethoxy]-phenyl}-ethylamino)-benzoic acid methyl ester The title compound (128 mg) was prepared from 280 mg (0.54 mmol) of Intermediate 159 and 72 mg (1.72 mmol) of lithium hydroxide monohydrate according to the method of Example 32 followed by purification via silica gel chromatography using MeOH/EtOAc (gradient of 0:1 to 1:19 with 1% NH$_4$OH) as eluent: low resolution MS (ES) m/e 502 (MH)$^+$; high resolution MS (FAB) m/e 504.1647 (MH$^+$), $C_{26}H_{24}NO_6F_3$ requires 504.1634; TLC (MeOH/EtOAc (1:19)): R$_f$=0.63.

Example 108

3-{4-[2-(Benzoxazol-2-yl-methylamino)-ethoxy]-phenyl}-3-(4-benzoyl-thienylamino)-propionic acid A solution of 100 mg (0.18 mmol) of Intermediate 160 in 5 mL of ethanol and 1 mL of water was heated to reflux with 30 mg of KOH for 45 minutes. The solution was concentrated to an oil, acidified with 0.1 N HCl to pH=5, and extracted with chloroform (2×20 mL). Concentration and purification by silica gel chromatography eluting with EtOAc, then 1% acetic acid in EtOAc gave the title compound (45 mg) as a yellow solid: low resolution MS (ESP$^+$) m/e 542 (MH$^+$); TLC (EtOAc with 1% AcOH): R$_f$=0.38.

Example 109

3-{4-[2-(Benzoxazol-2-yl-methylamino)-ethoxy]-phenyl}-2-(2-(4-biphenylcarbonyl)-phenylamino)-propionic acid To a solution of 0.9 g (1.44 mmol) Intermediate 162 in 5 mL water and 50 mL MeOH was added 0.6 g (14.4 mmol) LiOH. The mixture was refluxed for 0.5 h, concentrated, and partitioned between pH 7 phosphate buffer solution and EtOAc. The concentrated organics were purified by silica gel chromatography eluting with 0–5% MeOH in CH$_2$Cl$_2$ to yield the title compound as a yellow solid: $^1$H NMR (CDCl$_3$, 200 MHz) δ 9.00 (br s, 1H), 7.7–7.6 (m, 7H), 7.5–7.35 (m, 5H), 7.2–6.95 (m, 5H), 6.75 (m, 3H), 6.63 (t, 1H, J=7.5), 4.45 (br s, 1H), 3.27 (s, 3H), 3.2 (d, 2H, J=5.7; Low resolution MS (Cl) m/e 612 (MH$^+$).

Example 110

3-{4-[2-(Benzoxazol-2-yl-methylamino)-ethoxy]-phenyl}-2-(2-(4-methoxy-benzoyl)-phenylamino)-propionic acid The title compound was prepared from 0.29 g (0.5 mmol) Intermediate 164 and 31 mg LiOH (0.75 mmol) according to the procedure outlined in Example 32 followed by purification via trituration with hexanes: $^1$H NMR (DMSO-d6, 200 MHz) δ 8.35 (d, 2H, J=7.3), 7.55 (d, 2H, J=8.6), 7.39–7.25 (m, 5H), 7.15–6.9 (m, 5H), 6.8 (m, 3H), 6.6 (m, 1H), 4.3 (m, 1H), 4.15 (m, 2H), 3.8 (m, 5H), 3.2 (s, 3H), 3.0 (m, 2H); Low resolution MS (Cl) m/e 566 (MH$^+$).

Example 111

3-{4-[2-(Benzoxazol-2-yl-methylamino)-ethoxy]-phenyl}-2-(2-(4-methyl-benzoyl)-phenylamino)-propionic acid To a solution of 760 mg (1.35 mmol) of Intermediate 165 in 70 mL MeOH and 15 mL water was added 0.57 g (13.5 mmol) LiOH. The stirred solution was refluxed for 4 h, concentrated, taken up into water (15 mL) and CHCl$_3$ (15 mL) and the aqueous phase adjusted to pH=6–7 with 1.0 N HCl. Extraction with CHCl$_3$ followed by silica gel chromatography purification eluting first with EtOAc, then EtOAc with 0.5% AcOH provided 90 mg of the title compound: TLC (EtOAc with 0.5% AcOH): R$_f$=0.44; Low resolution MS (ESP$^+$) m/e 550 (MH$^+$).

Example 112

3-{4-[2-(Benzoxazol-2-yl-methylamino)-ethoxy]-phenyl}-2-(2-(2-methyl-benzoyl)-phenylamino)-propionic acid The title compound was prepared from Intermediate 166 (687 mg, 1.22 mmol) as described for the preparation of Example 111 to yield 500 mg of crude product. Purification by silica gel chromatography eluting first with 40–50% EtOAc in hexanes followed by 10% MeOH in CH$_2$Cl$_2$ gave 200 mg of the title compound. A pure fraction (21 mg) was obtained by preparative TLC (2000 microns, elution with EtOAc containing 0.5% AcOH): TLC (MeOH/CH$_2$Cl$_2$, 1/9): R$_f$=0.35; Low resolution MS (CI) m/e 550 (MH$^+$).

General Procedure for Preparation of Examples 113–128

A Whatman syringeless filter device PTFE "Autovial" 12 mL capacity with a 0.45 mm PTFE membrane with glass microfiber was charged with 100 mg (1.1 mmol) of Intermediate 118, followed by 4 mL of THF, the appropriate alcohol (5 mmol), DEAD (5 mmol),and either Ph$_3$P or TBP (5 mmol). Alternate conditions used TMAD (1,1'-azobis(N, N-dimethylformamide) (5 mmol) and 1:1 CH$_2$Cl$_2$:THF as a solvent. After rotating the autovials on an orbit shaker for ~1.5 h the resin was treated with a series of solvent washes of the resin in the following order: THF,MeOH,THF,DMF, CH2Cl2, then dried for 30 min. The resin was cleaved by treatment with 10% trifluoroacetic acid in CH$_2$Cl$_2$ for 1 hr. The filtrates were collected under vacuum in a Baker spe-24G Glass Column Processor unit, evaporated under N2, and dried under high vacuum for 24 h affording crude product. Compounds were then subjected to further purification by HPLC C$_{18}$ Waters Delta Prep 3000, Column: YMC-Pack ODS AA12S05-2520WT 250×20 mm I.D.S-5 mm, 120 Å, 0–100% B over ½ h, flow 18 mL/min, monitored at 220, B=0.1% trifluoroacetic acid in acetonitrile, A=0.1% trifluoroacetic acid in water. Analytical Column: YMC-Pack ODS AA1 2S05-2520WT 250×4.6 mm I.D. S-5 mm, 120 Å, 0–100% B at 1.5 mL/min. over 30 min, monitored at 220,B=0.1% trifluoroacetic acid in acetonitrile, A=0.1% trifluoroacetic acid in water.

Example 113

2-(2-Benzoyl-phenylamino)-3-{4-[2-(4-chloro-phenyl)-ethoxy]-phenyl}-propionic acid Reaction of Intermediate 118 with 2-(4-chlorophenyl) ethanol using the general procedure described above afforded a yellow solid: MS (ESP+) m/e 538 (MH$^+$); Anal. (C$_{30}$H$_{26}$NO$_4$Cl.TFA); HPLC: t$_r$=22.43 min.

Example 114

2-(2-Benzoyl-phenylamino)-3-{4-[2-(4-methyl-thiazol-5-yl)-ethoxy]-phenyl}-propionic acid Reaction of Intermediate 118 with 2-(4-methyl-thiazol-5-yl) ethanol using the general procedure described above afforded a yellow solid: MS (ESP+) m/e 487 (MH$^+$); Anal. (C$_{28}$H$_{26}$N$_2$O$_4$S .TFA); HPLC: t$_r$=17:43 min.

Example 115

2-(2-Benzoyl-phenylamino)-3-{4-2[-(4-chloro-phenylsulfanyl)ethoxy]-phenyl}-propionic acid Reaction of Intermediate 118 with 2-(4-chlorophenylsulfanyl) ethanol using the general procedure described above afforded a yellow solid: MS (ESP+) m/e 532 (MH$^+$); Anal. (C$_{30}$H$_{26}$ClNO$_4$S.TFA); HPLC: t$_r$=22.65 min.

Example 116

2-(2-Benzoyl-phenylamino)-3-[4-(4-isopropyl-benzyloxy)-phenyl]-propionic acid

Reaction of Intermediate 118 with 4-isopropyl benzyl alcohol using the general procedure described above afforded a yellow solid: MS (ESP+) m/e 516 (M+Na$^+$), 494 (MH$^+$); Anal. (C$_{32}$H$_{31}$NO$_4$.TFA); HPLC: t$_r$=23.36 min.

Example 117

2-(2-Benzoyl-phenylamino)-3-[4-(4-chloro-benzyloxy)-phenyl]-propionic acid

Reaction of Intermediate 118 with 4-chlorobenzyl alcohol using the general procedure described above afforded a yellow solid: MS (ESP+) m/e 486 (MH$^+$); Anal. (C$_{29}$H$_{24}$ClNO$_4$.TFA); HPLC: t$_r$=21.95 min.

Example 118

2-(2-Benzoyl-phenylamino)-3-{4-[3-(4-methoxy-phenyl)-propoxy]-phenyl}-propionic acid Reaction of Intermediate 118 with 3-(4-methoxyphenyl) propanol using the general procedure described above afforded a yellow solid: MS(ESP+)m/e 510 (MH$^+$); Anal. (C$_{32}$H$_{31}$NO$_5$.TFA); HPLC: t$_r$=23.48 min.

Example 119

2-(2-Benzoyl-phenylamino)-3-{4-[2-(4-dimethylamino-phenyl)-ethoxy]-phenyl}-propionic acid Reaction of Intermediate 118 with 2-(4-N,N-dimethylaminophenyl) ethanol using the general procedure described above afforded a yellow solid: MS(ESP+) m/e 509 (MH$^+$); Anal.(C$_{32}$H$_{32}$N$_2$O$_4$.TFA); HPLC: t$_r$=16.81 min.

Example 120

2-(2-Benzoyl-phenylamino)-3-{4-[2-(4-bromo-phenoxy)-ethoxy]-phenyl}-propionic acid Reaction of Intermediate 118 with 2-(4-bromophenoxy) ethanol using the general procedure described above afforded a yellow solid: MS (ESP+) m/e 560 (MH$^+$); Anal. (C$_{30}$H$_{26}$BrNO$_5$.TFA); HPLC: t$_r$=21.28 min.

Example 121

2-(2-Benzoyl-phenylamino)-3-{4-[2-(5-nitro-pyridin-2-yloxy)-ethoxy]-phenyl}-propionic acid Reaction of Intermediate 118 with 2-(5-nitropyridin-2-yloxy) ethanol using the general procedure described above afforded a yellow solid: MS(ESP+) m/e 528 (MH$^+$); Anal. (C$_{29}$H$_{25}$N$_3$O$_7$.TFA); HPLC: t$_r$=20.02 min.

Example 122

2-(2-Benzoyl-phenylamino)-3-(4-{2-[3-(5-methyl-pyridin-2-yl)-propoxy]-ethoxyl}-phenyl)-propionic acid Reaction of intermediate 118 with 2-[3-(6-methylpyridin-2-yl) propoxy] ethanol using the general procedure described above afforded a yellow solid: MS(ESP+) m/e 539 (MH$^+$); Anal.(C$_{33}$H$_{34}$N$_2$O$_5$.TFA); HPLC: t$_r$=16.35 min.

Example 123

2-(2-Benzoyl-phenylamino)-3-[4-(2-pyridin-3-yl-ethoxy]-phenyl]-propionic acid

Reaction of Intermediate 118 with 2-(2-pyridinyl) ethanol using the general procedure described above afforded a yellow solid: MS(ESP+) m/e 467 (MH$^+$);
Anal.(C$_{29}$H$_{26}$N$_2$O$_4$.TFA); HPLC: t$_r$=15.84 min.

Example 124

2-(2-Benzoyl-phenylamino)-3-{4-[2-(3-methyl-6-oxo-6H-pyridazin-1-yl)-ethoxy]-phenyl}-propionic acid Reaction of Intermediate 118 with 2-(3-methyl-6-oxo-6H-pyridazin-1-yl) ethanol using the general procedure described above afforded a yellow solid: MS(ESP+) m/e 498 (MH$^+$); Anal.(C$_{29}$H$_{27}$N$_3$O$_5$.TFA); HPLC: t$_r$=18.64 min.

Example 125

2-(2-Benzoyl-phenylamino)-3-{4-[2-(4-trifluoromethoxy-phenyl)-ethoxy]-phenyl}-propionic acid Reaction of Intermediate 118 with 2-(4-trifluoromethoxyphenyl) ethanol using the general procedure described above afforded a yellow solid: MS(ESP+) m/e 550 (MH$^+$); Anal.(C$_{31}$H$_{26}$NO$_5$F$_3$.TFA).

Example 126

2-(2-Benzoyl-phenylamino)-3-{4-[2-(3-cyano-phenoxy)-ethoxy]-phenyl}-propionic acid Reaction of Intermediate 118 with 2-(3-cyanophenoxy) ethanol using the general procedure described above afforded a yellow solid: MS(ESP+) m/e 507 (MH$^+$); Anal. (C$_{31}$H$_{26}$N$_2$O$_5$.TFA).

Example 127

2-(2-Benzoyl-phenylamino)-3-{4-[2-(6-methoxy-pyridin-2-ylsulfanyl)-ethoxy]-phenyl}-propionic acid Reaction of Intermediate 118 with 2-(6-methoxy-pyridin-2-ylsulfanyl) ethanol using the general procedure described above afforded a yellow solid: MS(ESP+) m/e 534 (MH$^+$); Anal.(C$_{30}$H$_{28}$N$_2$O$_5$S.TFA); HPLC: t$_r$=21.88 min.

Example 128

2-(2-Benzoyl-phenylamino)-3-{4-[1-(4-nitrophenyl)-pyrrolidin-2-ylmethoxy]-phenyl}-propionic acid Reaction of Intermediate 118 with (S)-(−)-1-(4-nitrophenyl)-2-pyrrolidineMeOH using the general procedure described above afforded a yellow solid: MS(ESP+), m/e 566 (MH$^+$); Anal.(C$_{33}$H$_{31}$N$_3$O$_6$.TFA); HPLC: t$_r$=22.07 min.

Alternative Intermediate 23

Intermediate 23 was prepared using the following alternative process. L-Tyrosine methyl ester (1.00 equiv., 0.96 wt.), 2-benzoyl-cyclohexanone (W. A. Denny et al., J. Med. Chem., 21(5), pp430–437 (1978)) (1.00 equiv., 1.00 wt.) and dimethoxyethane (5 volumes), were combined and heated to reflux overnight. 2–2.5 volumes of solvent were removed by distillation, and the suspension was allowed to cool to ambient temperature. The product was collected by vacuum filtration, washed with 0.5 volumes of cold dimethoxyethane and dried under house vacuum overnight. This product (1.00 wt., 1.00 equiv.) was combined with 10% palladium on carbon, (0.10 wt), para-nitrotoluene (0.75 equiv., 0.27 wt.), and 1-butanol (8.0–12.0 volumes) and heated to vigorous reflux for four to eighteen hours under a nitrogen atmosphere. The suspension was filtered hot, under nitrogen, through a celite plug, the pad was washed with hot 1-butanol (2–5 volumes) and the filtrate cooled to ambient temperature. After cooling, the crystals were collected by vacuum filtration, washed once with cold absolute ethanol, and air dried.

Alternative Intermediate 117

Intermediate 117, the acid analog of the methyl ester Intermediate 23, was prepared by the following alternative process. To a suspension of Intermediate 23 (1.00 equiv., 1.0 wt) in tetrahydrofuran (1.2–2.5 vol.) at 15–25° C. was added a solution of sodium hydroxide (2.2 equiv., 0.24 wt) in water (1.2–1.4 vol.) at a rate to keep the temperature less then 25° C. After addition was complete, the solution was warmed to 15–25° C. and stirred until no starting material remains by TLC. 2–3 M Hydrochloric Acid (2.2–2.6 equiv., 2.7–3.3 vol.) was added until a pH of <3 was reached, keeping the temperature below 25° C. Ethyl Acetate (6.0–7.0 vol.) was added, the mixture was vigorously stirred for 0.3–1.0 hour, then the layers separated and the aqueous layer discarded. The organic layer was extracted with brine (2.0–3.0 vol.) and the brine discarded. The organic layer was concentrated to 1.5–2.5 volumes and allowed to crystallize. Heptane (4.0–5.0 vol.) was added to complete the crystallization. The crystals were collected by filtration, washed with heptane (4.0–5.0 vol.) and dried.

Intermediate 167

The mesylate analog of the oxazole alcohol from Maybridge, was prepared using the following process. To a suspension of 2-(5-methyl-2-phenyloxazol-4-yl)ethanol, (commercially available from Maybridge), (1.0 eq, 1.0 wt) in toluene (10 vol) and triethylamine (1.1 eq, 0.75 vol) at 20–25° C. was added methanesulfonyl chloride (1.1 eq, 0.42 vol) at a rate which allowed the temperature to rise to 40° C. After the addition was complete the reaction was allowed to cool to 20–25° C. over 1 h. The organic phase was washed with water (3.5 vol) and brine (1.2 vol). The resulting solution was concentrated to 5 volumes, and stirred at 25° C. until crystallization commenced. Heptane (5 vol) was added to complete crystallization, and the mixture was stirred at 25° C. for 1 h. The solids were collected by filtration, washed with heptane (4.0 vol) and dried in a vacuum oven at 50° C.

Alternative Example 29

The compound of Example 29 was prepared by the following alternative method. To a slurry of the phenol, Intermediate 117, (1.0 eq, 1.0 wt), in dimethylsulfoxide (1.0 vol)/water (2.0 vol) was added solid NaOH (2.4 eq, 0.26 wt). The resulting solution was stirred at 50° C. and a solution of the mesylate, Intermediate 167 (1.28 eq, 1.0 wt), in dimethylsulfoxide (3.0 vol) was added dropwise at a rate to maintain a temperature of 48–52° C. This mixture was stirred at 48–52° C. for 22 hours, cooled to 25° C., and washed three times with methyl tert-butyl ether (6.0 vol). The aqueous phase was diluted first with ethanol (2.0 vol), followed by glacial acetic acid (2.0 vol), and then water (6.0 vol) was added dropwise to the solution with vigorous stirring. Seed crystals were added when the solution became turbid and cloudy. The resulting precipitate was filtered, washed with water (6.0 vol), then ethanol:water/50:50 (12.0 vol) and vacuum dried at 50° C. The resulting yellow solid was recrystallized from ethanol:water/95:5 (18.0 vol), and vacuum dried to constant weight at 50° C.

Second Alternative Example 29

The compound of Example 29 was prepared by the following second alternative method. To a mixture of phenol ester, Intermediate 23, (1 wt) 2-(5-methyl-2-phenyloxazol-4-yl)ethanol, (commercially available from Maybridge) (0.65 wt), and triphenylphosphine (0.88 wt) in toluene (3.5 vol) at 40° C. was added a solution of diisopropyl azodicarboxylate (0.66 vol) in toluene (0.5 vol) dropwise at such a rate to keep the temperature between 40 and 50° C. After the reaction was complete (HPLC) the resulting solution was concentrated under vacuum at 50° C. by removing toluene (2 vol), allowed to cool to room temperature, diluted with methyl tert-butyl ether (4 vol) and chilled to 0° C. After 1 hour at 0° C. the mixture was filtered to remove triphenylphosphine oxide and the filter pad was washed with cold (0° C.) methyl tert-butyl ether (2 vol). The resulting solution was washed with 2.5N NaOH (2.5 vol. 0° C.). 2.5 N NaOH (2.5 vol) was added and the mixture was stirred at room temperature until hydrolysis was complete (HPLC). Dimethyl sulfoxide (5 vol) was added and the phases separated. The aqueous phase was washed with methyl tert-butyl ether (3 vol), diluted first with ethanol (2.0 vol), followed by glacial acetic acid (2.0 vol), and then water (6.0 vol) was added dropwise to the solution with vigorous stirring. Seed crystals were added when the solution became turbid and cloudy. The resulting precipitate was filtered, then washed with ethanol:water/50:50 (6 vol). The resulting solids were slurried with hot ethanol:water/50:50 (6 vol) and filtered at 70° C. The resulting yellow solid was recrystallized from ethanol:water/95:5 (13.0 vol), and vacuum dried to constant weight at 50° C.

DEMONSTRATION OF EFFICACY OF COMPOUNDS

Protocols

1. PPARgamma Transient Cotransfection Assay: The pSG5-mPPARg and pSG5-hPPARg chimeric receptor expression plasmids and the $(UAS)_5$-tk-CAT reporter plasmid have been previously described (Kliewer, S. A., et. al. *Cell* 83, 813–819 (1995); J. M. Lehmann et. al., *J. Biol. Chem.* 12953–12956, 270 (1995)). Transient cotransfection assays using these plasmids were performed as previously described (Kliewer, S. A., et. al. *Cell* 83, 813–819 (1995); J. M. Lehmann et. al., *J. Biol. Chem.* 12953–12956, 270 (1995)).
2. hPPARgamma Ligand Binding Assay: The PPAR-gamma ligand binding domain (amino acids 195–475) was expressed with an N-terminal 10x-histidine tag in *E. coli* cells. The cells were lysed and receptor was purified by means of the epitope tag. The stock solution of protein was diluted to 200 nM in assay buffer (50 mM Tris, 50 mM KCl, pH 8 20 mM CHAPS, 2 mM EDTA 10 mM DTT (Fresh)) just before use.

Test compounds were prepared as 6 mM stock solutions in DMSO. Two sequential 10-fold dilutions were made into assay buffer to give compound and DMSO concentrations of 60 uM and 1%, respectively.12.5 uL of the diluted compound was added to a well in the left-most column of a microtiter plate containing 67.5 uL of assay buffer, the contents of the well were mixed, and 25 uL of this solution was transferred to the next well where it was mixed with 50 uL of assay buffer (3-fold dilution). This process was repeated to give a total of eleven (11) concentrations arrayed row-wise in the 96 well plate for each test compound. The right-most column of wells was used for controls. For each experiment, an appropriate amount of 3H-BRL 49,653 was blown to dryness in a glass vial, resuspended in assay buffer (50 mM Tris, 50 mM KCl, pH 8 20 mM CHAPS, 2 mM EDTA 10 mM DTT (Fresh)) to give a 400 nM concentration, vortexed, and sonicated for 10 seconds. Radioligand ([3H]-BRL 49,653) and receptor was added to each well of the plate containing test compound. Plates were incubated at room temperature for 2 hrs, and then cooled on ice for 30 minutes. 50 uL samples from each well of a single test plate were simultaneously loaded onto an equilibrated AGTC 96 well gel filtration block (Advanced Genetics Technology Corp.) using a Zymak Rapidplate automated pipettor. The block was placed on top of a clean microtiter plate and centrifuged @1,100×g for 4 min. 200 uL of scintillation fluid was added to each well, the plates were sealed and allowed to equilibrate for at least 4 hours before counting in a Wallac 1250 Microbeta counter.

Nonspecific binding as assessed by control wells containing an excess of [3H]-BRL 49,653 was subtracted from all wells and plots of compound concentration versus CPM bound were constructed. Ki's were determined from a nonlinear least squares fit of the data to a simple competitive binding model. For the purposes of data analysis, a Kd for [3H]-BRL 49,653 of 200 nM was utilized.

3. In vivo Evaluation: Experiments were performed on db/db mice (n=40–48), approximately 60 day old, divided into either vehicle or treatment groups. From each group 8–12 animals were placed in Nalgene metabolic cages, 2 per cage. The remaining animals are housed in standard rack cages; 3–4 per cage. Test compounds were dissolved in an appropriate vehicle. Animals were administered either the vehicle or the compound (dose=5 mg/kg) delivered at 5 ml/kg, b.i.d., via oral gavage for fourteen days. Daily measurements were made of mice housed in metabolic cages to determine consumption of food and water, urine output and urinary glucose excretion and changes in body weight. Animals housed in rack cages were weighed approximately every four days to monitor changes in body weight. An equal number of animals from each group were sampled on days 0, 4, 7 and 14. Mice were anesthetized with isolflurane, blood samples were obtained by cardiac puncture and analyzed to determine plasma levels of glucose, insulin, total cholesterol, triglycerides and non-esterified free fatty acids (NEFA's).

BIOLOGICAL DATA FOR EXAMPLES 1–128

| Example Number | PPARg Fold. Act. | PPARg $EC_{50}$ (nM) | PPARg $K_i$ (nM) | % lowering of plasma glucose |
|---|---|---|---|---|
| Example 1 | 26 | 60 | 55 | |
| Example 2 | 23 | 100 | 1000 | |
| Example 3 | 3 | | | |
| Example 4 | 20 | 3000 | 1000 | |
| Example 5 | 10 | 9000 | >3000 | |
| Example 6 | 4 | | | |
| Example 7 | 5 | | | |
| Example 8 | | 720 | 21 | |
| Example 9 | | 630 | 700 | |
| Example 10 | | 170 | 300 | |
| Example 11 | 23 | 10 | 110 | |
| Example 12 | | 5 | 20 | 58% |
| Example 13 | | 60 | 1300 | |
| Example 14 | 18 | 1 | 80 | |
| Example 15 | | 1 | 40 | |
| Example 16 | | 1 | 20 | 63% |
| Example 17 | | 1 | 80 | |
| Example 18 | | 5 | 10 | |
| Example 19 | | 65 | 185 | |
| Example 20 | | 120 | 180 | |
| Example 21 | | 150 | 530 | |
| Example 22 | | 20 | 65 | |
| Example 23 | | 1 | 50 | |
| Example 24 | | 1 | 30 | |
| Example 25 | | 1 | 70 | |
| Example 26 | | 670 | 1900 | |
| Example 27 | | 400 | 300 | |
| Example 28 | | 25 | | |
| Example 29 | | 0.2 | 20 | 70% |
| Example 30 | | 50 | 300 | |
| Example 31 | | 450 | 145 | |
| Example 32 | | 1 | 25 | |
| Example 33 | | 0.1 | 30 | |
| Example 34 | | 0.5 | 10 | |
| Example 35 | | 5 | 1 | |
| Example 36 | | 40 | 380 | |
| Example 37 | | 1 | 50 | |
| Example 38 | | 1 | 160 | |
| Example 39 | | 865 | 3000 | |
| Example 40 | | 5 | 70 | |
| Example 41 | | 5 | 70 | |
| Example 42 | | 5 | | |
| Example 43 | | 1000 | 1000 | |
| Example 44 | | 185 | 15 | |
| Example 45 | | 1 | 30 | |
| Example 46 | | 900 | 750 | |
| Example 47 | | 50 | 240 | |
| Example 48 | | 20 | 115 | |
| Example 49 | | 10 | 80 | |
| Example 50 | | 50 | 390 | |
| Example 51 | | 350 | 140 | |
| Example 52 | | 80 | 100 | |
| Example 53 | | 25 | 70 | |
| Example 54 | | 250 | 3000 | |
| Example 55 | | 460 | 1400 | |
| Example 56 | | 1 | 10 | |
| Example 57 | | 150 | 1245 | |
| Example 58 | | 1 | 30 | |
| Example 59 | | 95 | 100 | |
| Example 60 | | 1 | 15 | |
| Example 61 | | 15 | 10 | |
| Example 62 | | 20 | 20 | |
| Example 63 | | 20 | 30 | |
| Example 64 | | 10 | 50 | |
| Example 65 | | 140 | 40 | |
| Example 66 | | 230 | 20 | |
| Example 67 | | 0.2 | 10 | |
| Example 68 | | 1 | 10 | |
| Example 69 | | 100 | 290 | |
| Example 70 | | 200 | 250 | |
| Example 71 | | 150 | | |
| Example 72 | | 5 | 30 | |
| Example 73 | | 25 | 115 | |
| Example 74 | | 55 | 800 | |
| Example 75 | | 100 | 75 | |
| Example 76 | | 10 | 110 | |
| Example 77 | | 65 | 155 | |
| Example 78 | | 200 | 40 | |
| Example 79 | | 30 | 50 | |
| Example 80 | | 10 | 10 | |
| Example 81 | | 400 | 130 | |
| Example 82 | | 25 | 65 | |
| Example 83 | | 165 | 350 | |
| Example 84 | | 55 | | |
| Example 85 | | 20 | | |
| Example 86 | | 30 | 650 | |
| Example 87 | | 465 | 1160 | |
| Example 88 | | 0.5 | 50 | |
| Example 89 | | 60 | 3000 | |
| Example 90 | | | 3000 | |
| Example 91 | | 20 | | |
| Example 92 | | 400 | 20 | |
| Example 93 | | 55 | 100 | |
| Example 94 | | 10 | 40 | |
| Example 95 | | 700 | 380 | |
| Example 96 | | 300 | 280 | |
| Example 97 | | 20 | 5 | |
| Example 98 | | 375 | 10 | |
| Example 99 | | 1 | 70 | |
| Example 100 | | 1 | 40 | |
| Example 101 | | 1 | 70 | |
| Example 102 | | 80 | 20 | |
| Example 103 | | 180 | | |
| Example 104 | | 900 | 3000 | |
| Example 105 | | 35 | 140 | |
| Example 106 | | 300 | 140 | |
| Example 107 | | 190 | 40 | |
| Example 108 | | 20 | 80 | |
| Example 109 | | 200 | 700 | |
| Example 110 | | 65 | 50 | |
| Example 111 | | 10 | 70 | |
| Example 112 | | 10 | 130 | |
| Example 113 | | 80 | 150 | |
| Example 114 | | 250 | 140 | |
| Example 115 | | 165 | 200 | |
| Example 116 | | 165 | 470 | |
| Example 117 | | 1000 | 655 | |
| Example 118 | | 500 | 730 | |
| Example 119 | | 470 | 3000 | |
| Example 120 | | 350 | 65 | |
| Example 121 | | 320 | 100 | |
| Example 122 | | 500 | 625 | |
| Example 123 | | 620 | 280 | |
| Example 124 | | 810 | 130 | |
| Example 125 | | 200 | 160 | |
| Example 126 | | 800 | 370 | |
| Example 127 | | 460 | 160 | |
| Example 128 | | 20 | 70 | |

What is claimed is:

1. A compound having the formula (I):

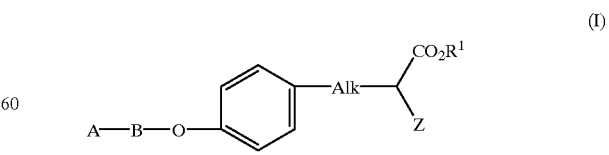

wherein

A is selected from the group consisting of:
(i) phenyl, wherein said phenyl is optionally substituted by one or more halogen atoms, $C_{1-6}$alkyl, $C_{1-3}$alkoxy, $C_{1-3}$fluoroalkoxy, nitrile, or —NR$^7$R$^8$ where R$^7$ and R$^8$ are independently hydrogen or $C_{1-3}$alkyl;
(ii) a 5- or 6-membered heterocyclic group containing at least one heteroatom selected from oxygen, nitrogen and sulfur; and
(iii) a fused bicyclic ring

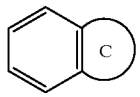

wherein ring C represents a heterocyclic group as defined in point (ii) above, which bicyclic ring is attached to group B via a ring atom of ring C;
B is selected from the group consisting of:
—MC$_{1-6}$alkylene or C$_{1-6}$alkyleneMC$_{1-6}$alkylene, wherein M is O, S, or —NR$^2$ wherein R$^2$ represents hydrogen or $C_{1-3}$alkyl; and
Het-C$_{1-6}$alkylene, wherein Het represents a 5- or 6-membered heterocyclic group containing at least one nitrogen heteroatom and optionally at least one further heteroatom selected from oxygen, nitrogen and sulfur and optionally substituted by $C_{13}$alkyl;
Alk represents $C_{1-3}$alkylene;
R$^1$ represents hydrogen or $C_{1-3}$alkyl;
Z is —NR$^3$R$^4$, wherein R$^3$ represents hydrogen or $C_{1-3}$alkyl, and R$^4$ represents —Y—(C=O)—T—R$^5$, or —Y—(CH(OH))—T—R$^5$, wherein:
(a) Y represents a phenyl optionally substituted by one or more $C_{1-3}$ alkyl groups and/or one or more halogen atoms;
(b) T represents a bond, $C_{1-3}$alkyleneoxy, —O— or —N(R$^6$)—, wherein R$^6$ represents hydrogen or $C_{1-3}$alkyl;
(c) RI represents $C_{1-6}$alkyl, $C_{4-6}$cycloalkyl or cycloalkenyl, phenyl (optionally substituted by one or more: halogen atoms, $C_{1-3}$alkyl, $C_{1-3}$alkoxy groups, $C_{0-3}$alkyleneNR$^9$R$^{10}$ where each R$^9$ and R$^{10}$ is independently hydrogen, $C_{1-3}$alkyl, —SO$_2$C$_{1-3}$alkyl, or —CO$_2$C$_{1-3}$alkyl, —SO$_2$NHC$_{1-3}$alkyl, C$_{0-3}$alkyleneCO$_2$H, C$_{0-3}$alkyleneCO$_2$C$_{1-3}$alkyl, or —OCH$_2$C(O)NH$_2$), a 5- or 6-membered heterocyclic group as defined in point (ii) above,
or a bicylic fused ring

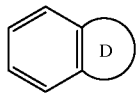

wherein ring D represents a 5- or 6-membered heterocyclic group containing at least one heteroatom selected from oxygen, nitrogen and sulfur and optionally substituted by (=O), which bicyclic ring is attached to T via a ring atom of ring D, or —C$_{1-6}$alkyleneMR$^{11}$ M is O, S, or —NR$^2$ wherein R$^2$ and R$^{11}$ are independently hydrogen or $C_{1-3}$alkyl;
or a tautomeric form thereof, and/or a pharmaceutically acceptable salt or solvate thereof.

2. The compound of claim 1 wherein each of said 5- or 6-membered heterocyclic groups is independently selected from the group consisting of substituted or unsubstituted imidazolidinyl, piperidyl, piperazinyl pyrrolidinyl, morpholinyl, pyridyl, pyridazinyl, pyrimidinyl, pyrazinyl, pyrrolyl, pyrazolyl, imidazolyl, pyranyl, furyl, thienyl, oxazolyl, isoxazolyl, oxadiazolyl, thiazolyl, thiadiazolyl, triazolyl, or tetrazolyl.

3. A compound according to claim 1 wherein A represents phenyl, pyridyl, piperazinyl or any of which is optionally substituted by one or more $C_{1-3}$alkyl.

4. A compound according to claim 3, wherein A represents phenyl, piperazinyl or pyridyl.

5. A compound according to claim 1, wherein B represents, N(CH$_3$) $C_{1-3}$alkylene or Het-C$_{1-6}$alkylene wherein Het represents a 5-membered heterocyclic group containing at least one nitrogen atom and optionally at least one further heteroatom selected from oxygen and sulphur, substituted or unsubstituted by $C_{1-3}$alkyl.

6. A compound according to claim 5 wherein B represents, oxazolyl-C$_{1-6}$-alkylene wherein said oxazolyl is optionally substituted by $C_{1-3}$alkyl, or thiazolyl which is optionally substituted by $C_{1-3}$alkyl.

7. A compound according to claim 1, wherein Alk represents methylene.

8. A compound according to claim 1, wherein R$^1$ represents hydrogen, methyl or ethyl.

9. A compound according to claim 8, wherein R$^1$ is hydrogen.

10. A compound according to claim 1, wherein Z represents NR$^3$R$^4$ wherein R$^3$ and R$^4$ are as defined in claim 1.

11. A compound according to claim 10 wherein R$^3$ is hydrogen.

12. A compound according to claim 11, wherein R$^4$ represents —Y(C=O)—T—R$^5$ wherein R$^5$ is as defined in claim 1.

13. The compound of claim 12 wherein T is a bond or —O—.

14. A compound according to claim 13 wherein R$^5$ represents $C_{1-3}$alkyl or phenyl (optionally substituted by one or more halogen atoms or one or more $C_{1-3}$alkyl groups).

15. The compound of claim 10 wherein Z is

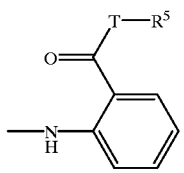

T is a bond or —O—, R$^5$ is $C_{1-6}$alkyl, or phenyl (optionally substituted by one or more: halogen atoms, $C_{1-3}$alkyl, $C_{1-3}$alkoxy groups, $C_{0-3}$alkyleneNR$^9$R$^{10}$ where each R$^9$ and R$^{10}$ is independently hydrogen, $C_{1-3}$alkyl, —SO$_2$C$_{1-3}$alkyl, or —CO$_2$C$_{1-3}$alkyl, —SO$_2$NHC$_{1-3}$alkyl, C$_{0-3}$alkyleneCO$_2$H, C$_{0-3}$alkyleneCO$_2$C$_{1-3}$alkyl, or —OCH$_2$C(O)NH$_2$).

16. A compound according to claim 11 wherein R$^4$ represents

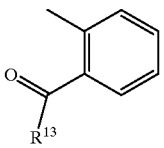

wherein R$^{13}$ is phenyl or OCH$_3$.

17. A compound according to claim 1 of formula 1(a)

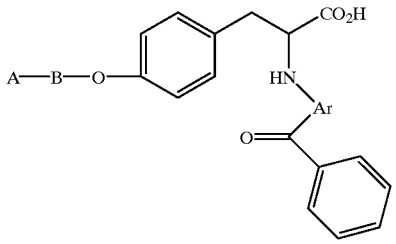

(1a)

wherein A and B are as described in claim 1 and Ar represents a phenyl or a 5 or 6 membered heteoaryl group containing at least the heteroatom selected from oxygen, nitrogen and sulphur and solvates thereof.

18. A compound selected from the group consisting of:

2-(1-carboxy-2-{4-{2-(5-methyl-2-phenyl-oxazol-4-yl )-ethoxy]-phenyl}-ethylamino)-benzoic acid methyl ester;

3-{4-[2-(benzoxazol-2-yl-methyl-amino)-ethoxy]-phenyl}-2(S)-(2-benzoyl-phenylamino)-propionic acid;

3-{4-[2-(Benzoxazol-2-yl-methyl-amino)-ethoxy]-phenyl}-2-(2-cyclohexanecarbonyl-phenylamino)-propionic acid;

3-{4-[2-Benzoxazol-2-yl-methyl-amino)-ethoxy]-phenyl}-2-(2-benzoyl-thiophen-3-ylamino)-propionic acid;

2(S)-[1-methoxycarbonyl-2-(4-{2-[5-methyl-2-(4-methyl-piperazin-1-yl)-thiazol-4-yl]-ethoxy}-phenyl)-ethylamino]-benzoic acid;

2(S)-(2-benzoyl-phenylamino)-3-{4-[2-(methyl-pyridin-2-yl-amino)-ethoxy]-phenyl}-propionic acid;

2(S)-(2-Benzoyl-phenylamino)-3-{4-[2-(5-methyl-2-phenyl-oxazol-4-yl)-ethoxy]-phenyl}-propionic acid;

and pharmaceutically acceptable salts and solvates thereof.

19. A pharmaceutical composition comprising a compound according to claim 1 or a pharmaceutically acceptable salt or solvate thereof together with a pharmaceutically acceptable carrier.

20. A method for treating or preventing a PPAR-gamma mediated disease or condition comprising administering a compound according to claim 1.

21. A method for lowering blood-glucose comprising administering a compound according to any of claim 1.

22. A method for treating or preventing hyperglycaemia, dyslipidemia, Type II diabetes, Type I diabetes, hypertriglyceridemia, syndrome X, insulin resistance, heart failure, diabetic dyslipidemia, hyperlipidemia, hypercholesteremia, hypertension, obesity, anorexia bulimia, anorexia nervosa, and cardiovascular disease, comprising administering a compound according to claim 1.

23. A method for the preparation of compounds claim 1 comprising the step of reacting a compound of Formula A—B—X with a compound of Formula (II)

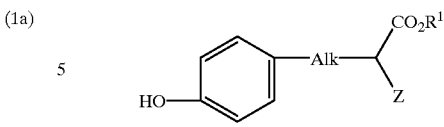

(II)

wherein A, B, alk, $R^1$, and Z are as defined in claim 1 and B comprises a $C_{1-6}$alkylene group and X is a leaving group or a hydroxyl group.

24. The method of claim 23 wherein X is a hydroxyl group, a halide, or an alkyl- or aryl-sulfonyloxy group, A is phenyl, pyridyl, or benzoxazolyl, B is said Het-$C_{1-6}$Alkylene, and Z is —NH—Y(C=O)—T—$R^5$ wherein Y is phenyl optionally substituted by one or more $C_{1-3}$alkyl groups and/or one or more halogen atoms, T is a bond or —O—, and $R^5$ is $C_{1-6}$alkyl, or phenyl (optionally substituted by one or more halogen atoms, $C_{1-3}$alkyl, $C_{1-3}$alkoxy groups, $C_{0-3}$alkyleneNR$^9$R$^{10}$ where each $R^9$ and $R^{10}$ is independently hydrogen, $C_{1-3}$alkyl, —SO$_2$C$_{1-3}$alkyl, or —CO$_2$C$_{1-3}$alkyl, —SO$_2$NHC$_{1-3}$alkyl, $C_{0-3}$alkyleneCO$_2$H, $C_{0-3}$alkyleneCO$_2$C$_{1-3}$alkyl, or —OCH$_2$C(O)NH$_2$).

25. The method of claim 23 wherein $R^1$ is hydrogen and X is a halide, or an alkyl- or aryl-sulfonyloxy group.

26. The method of claim 25 wherein said A—B—X and said compound of Formula (II) are:

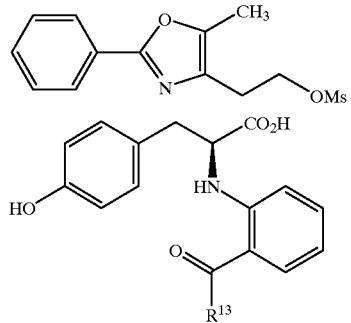

wherein OMs is a mesylate leaving group and $R^{13}$ is a phenyl or —OCH$_3$ group.

27. The method of claim 23 wherein $R^1$ is a $C_{1-3}$alkyl and X is a hydroxyl group.

28. The method of claim 27 wherein said reaction comprises a Mitsunobu reaction followed by hydrolysis of the depicted alkyl ester group to the corresponding acid without isolation of the ester.

29. The method of claim 28 wherein said Mitsunobu reaction is carried out in a reaction mixture comprising toluene.

30. The method of any of claim 27, wherein said A—B—X and said compound of Formula (II) are:

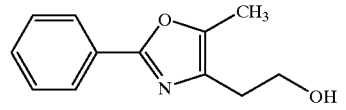

-continued

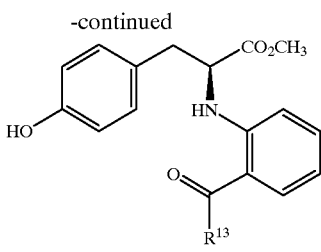

wherein R[13] is a phenyl or —OCH$_3$ group.

31. The method of claim 23, wherein in the compound of Formula (II), Z is

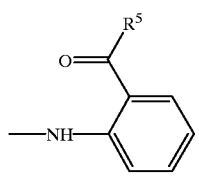

and wherein the compound of Formula (II) is prepared comprising the steps of first preparing a compound of Formula (II) wherein Z is

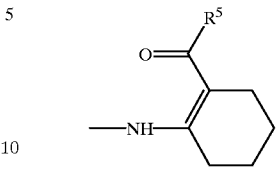

followed by the step of dehydrogenating with a dehydrogenation catalyst in the presence of a hydrogen acceptor.

32. The method of claim 31 wherein said hydrogen acceptor is an aromatic nitro compound.

33. A compound according to claim 15 wherein A represents phenyl, pyridyl, piperazinyl or benzoxazolyl, any of which is optionally substituted by one or more $C_{1-3}$alkyl, and wherein B represents $N(CH_3)(CH_2)_2$, oxazolyl-$C_{1-6}$-alkylene wherein said oxazolyl is optionally substituted by $C_{1-3}$alkyl, or thiazolyl which is optionally substituted by $C_{1-3}$alkyl.

* * * * *